United States Patent
Didiuk et al.

(10) Patent No.: US 10,294,225 B2
(45) Date of Patent: *May 21, 2019

(54) N1-PYRAZOLOSPIROKETONE ACETYL-COA CARBOXYLASE INHIBITORS

(71) Applicant: PFIZER INC., New York, NY (US)

(72) Inventors: Mary Didiuk, Madison, CT (US); Robert Lee Dow, Groton, CT (US); David Andrew Griffith, Sudbury, MA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/883,109

(22) Filed: Jan. 30, 2018

(65) Prior Publication Data

US 2018/0162858 A1 Jun. 14, 2018

Related U.S. Application Data

(63) Continuation of application No. 15/236,635, filed on Aug. 15, 2016, now Pat. No. 9,908,883, which is a continuation of application No. 14/851,572, filed on Sep. 11, 2015, now abandoned, which is a continuation of application No. 14/491,016, filed on Sep. 19, 2014, now Pat. No. 9,145,416, which is a continuation of application No. 13/876,211, filed as application No. PCT/IB2011/054119 on Sep. 20, 2011, now Pat. No. 8,859,577.

(60) Provisional application No. 61/388,102, filed on Sep. 30, 2010.

(51) Int. Cl.
| | |
|---|---|
| A61K 31/44 | (2006.01) |
| C07D 471/10 | (2006.01) |
| C07D 491/20 | (2006.01) |
| C07D 519/00 | (2006.01) |
| A61K 31/438 | (2006.01) |
| A61K 31/519 | (2006.01) |
| A61K 45/06 | (2006.01) |
| C07D 487/10 | (2006.01) |
| A61K 31/435 | (2006.01) |

(52) U.S. Cl.
CPC .......... *C07D 471/10* (2013.01); *A61K 31/435* (2013.01); *A61K 31/438* (2013.01); *A61K 31/519* (2013.01); *A61K 45/06* (2013.01); *C07D 487/10* (2013.01); *C07D 491/20* (2013.01); *C07D 519/00* (2013.01)

(58) Field of Classification Search
CPC ................. C07D 471/10; A61P 3/00
See application file for complete search history.

(56) References Cited

U.S. PATENT DOCUMENTS

| | | | |
|---|---|---|---|
| 8,288,405 B2 | 10/2012 | Bagley et al. | |
| 8,859,577 B2 * | 10/2014 | Didiuk ................. | C07D 471/10 514/278 |
| 9,145,416 B2 * | 9/2015 | Didiuk ................. | C07D 471/10 |
| 9,908,883 B2 * | 3/2018 | Didiuk ................. | C07D 471/10 |

| | | |
|---|---|---|
| 2008/0171761 A1 | 7/2008 | Tomoharu et al. |
| 2009/0253725 A1 | 10/2009 | Chang et al. |
| 2009/0270435 A1 | 10/2009 | Corbett et al. |
| 2010/0000982 A1 | 1/2010 | Anderson et al. |
| 2010/0009982 A1 | 1/2010 | Anderson et al. |
| 2011/0028390 A1 | 2/2011 | Corbett et al. |
| 2011/0111046 A1 | 5/2011 | Bagley et al. |
| 2016/0034775 A1 | 12/2016 | Didiuk et al. |

FOREIGN PATENT DOCUMENTS

| | | |
|---|---|---|
| EP | 1911753 | 11/2009 |
| EP | 2123652 | 11/2009 |
| JP | 2005-119987 | 5/2005 |
| WO | 2003/072197 | 9/2003 |
| WO | 2004/002986 | 1/2004 |
| WO | 2004/092179 | 10/2004 |
| WO | 2005/113069 | 12/2005 |
| WO | 2007/011809 | 1/2007 |
| WO | 2007/011811 | 1/2007 |
| WO | 2007/061676 | 5/2007 |
| WO | 2007/095603 | 8/2007 |
| WO | 2008/065508 | 6/2008 |
| WO | 2008/088689 | 7/2008 |
| WO | 2008/102749 | 8/2008 |
| WO | 2008/125945 | 10/2008 |
| WO | 2009/144554 | 12/2009 |
| WO | 2009/144555 | 12/2009 |
| WO | 2010/002010 | 1/2010 |
| WO | 2011/058473 | 5/2011 |
| WO | 2011/058474 | 5/2011 |
| WO | 2012/042433 | 4/2012 |

OTHER PUBLICATIONS

Database WPI Week 200537; Derwent Publications Ltd. No. 2005-359210 (XP002471702).

(Continued)

*Primary Examiner* — Rei Tsang Shiao
(74) *Attorney, Agent, or Firm* — Richard V. Zanzalari

(57) ABSTRACT

The invention provides a compound of Formula (I)

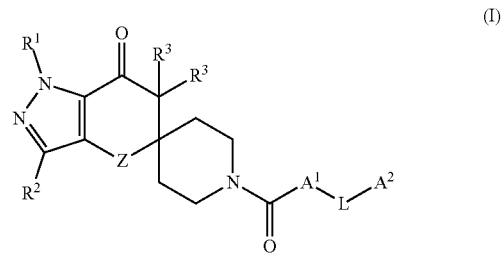

(I)

or a pharmaceutically acceptable salt of the compound, wherein $R^1$, $R^2$, $R^3$, Z, $A^1$, L and $A^2$ are as described herein; pharmaceutical compositions thereof; and the use thereof in treating diseases, conditions or disorders modulated by the inhibition of an acetyl-CoA carboxylase enzyme(s) in an animal.

8 Claims, 4 Drawing Sheets
Specification includes a Sequence Listing.

(56) References Cited

OTHER PUBLICATIONS

Abu-Elheiga, et al., "Acetyl-CoA carboxylase 2 mutant mice are protected against obesity and diabetes induced by high-fat/high-carbohydrate diets", PNAS, vol. 100(18), pp. 10207-10212 (2003).
Choi, et al., "Continuous fat oxidation in acetyl-CoA carboxylase 2 knockout mice increases total energy expenditure, reduces fat mass, and improves insulin sensitivity", PNAS, vol. 104(42), pp. 16480-16485 (2007).
Oh, et al., "Glucose and fat metabolism in adipose tissue of acetyl-CoA carboxylase 2 knockout mice", PNAS, vol. 102(5), pp. 1384-1389 (2005).
Savage, et al., "Reversal of diet-induced hepatic steatosis and hepatic insulin resistance by antisense oligonucleotide inhibitors of acetyl-CoA carboxylases 1 and 2", J. Clin. Invest., vol. 116(3), pp. 817-824 (2006).
Bagley, et al., "Synthesis of 7-oxo-dihydrospiro[indazole-5,4'-piperidine] Acetyl-CoA Carboxylase Inhibitors", The Journal of Organic Chemistry, vol. 77(3), pp. 1497-1506 (2012).

* cited by examiner

FIGURE 1

SEQ. ID NO. 1:

MAHHHHHHDEVDDEPSPLAQPLELNQHSRFIIGSVSEDNSEDEISNLVKLDLLEKEGSLSPA
SVGSDTLSDLGISSLQDGLALHIRSSMSGLHLVKQGRDRKKIDSQRDFTVASPAEFVTRFG
GNKVIEKVLIANNGIAAVKCMRSIRRWSYEMFRNERAIRFVVMVTPEDLKANAEYIKMADHY
VPVPGGPNNNNYANVELILDIAKRIPVQAVWAGWGHASENPKLPELLLKNGIAFMGPPSQA
MWALGDKIASSIVAQTAGIPTLPWSGSGLRVDWQENDFSKRILNVPQELYEKGYVKDVDDG
LQAAEEVGYPVMIKASEGGGGKGIRKVNNADDFPNLFRQVQAEVPGSPIFVMRLAKQSRHL
EVQILADQYGNAISLFGRDCSVQRRHQKIIEEAPATIATPAVFEHMEQCAVKLAKMVGYVSA
GTVEYLYSQDGSFYFLELNPRLQVEHPCTEMVADVNLPAAQLQIAMGIPLYRIKDIRMMYGV
SPWGDSPIDFEDSAHVPCPRGHVIAARITSENPDEGFKPSSGTVQELNFRSNKNVWGYFS
VAAAGGLHEFADSQFGHCFSWGENREEAISNMVVALKELSIRGDFRTTVEYLIKLLETESFQ
MNRIDTGWLDRLIAEKVQAERPDTMLGVVCGALHVADVSLRNSVSNFLHSLERGQVLPAHT
LLNTVDVELIYEGVKYVLKVTRQSPNSYVVIMNGSCVEVDVHRLSDGGLLLSYDGSSYTTY
MKEEVDRYRITIGNKTCVFEKENDPSVMRSPSAGKLIQYIVEDGGHVFAGQCYAEIEVMKM
VMTLTAVESGCIHYVKRPGAALDPGCVLAKMQLDNPSKVQQAELHTGSLPRIQSTALRGEK
LHRVFHYVLDNLVNVMNGYCLPDPFFSSKVKDWVERLMKTLRDPSLPLLELQDIMTSVSGR
IPPNVEKSIKKEMAQYASNITSVLCQFPSQQIANILDSHAATLNRKSEREVFFMNTQSIVQLV
QRYRSGIRGHMKAVVMDLLRQYLRVETQFQNGHYDKCVFALREENKSDMNTVLNYIFSHA
QVTKKNLLVTMLIDQLCGRDPTLTDELLNILTELTQLSKTTNAKVALRARQVLIASHLPSYELR
HNQVESIFLSAIDMYGHQFCIENLQKLILSETSIFDVLPNFFYHSNQVVRMAALEVYVRRAYIA
YELNSVQHRQLKDNTCVVEFQFMLPTSHPNRGNIPTLNRMSFSSNLNHYGMTHVASVSDV
LLDNSFTPPCQRMGGMVSFRTFEDFVRIFDEVMGCFSDSPPQSPTFPEAGHTSLYDEDKV
PRDEPIHILNVAIKTDCDIEDDRLAAMFREFTQQNKATLVDHGIRRLTFLVAQKDFRKQVNYE
VDRRFHREFPKFFTFRARDKFEEDRIYRHLEPALAFQLELNRMRNFDLTAIPCANHKMHLYL
GAAKVEVGTEVTDYRFFVRAIIRHSDLVTKEASFEYLQNEGERLLLEAMDELEVAFNNTNVR
TDCNHIFLNFVPTVIMDPSKIEESVRSMVMRYGSRLWKLRVLQAELKINIRLTPTGKAIPIRLF
LTNESGYYLDISLYKEVTDSRTAQIMFQAYGDKQGPLHGMLINTPYVTKDLLQSKRFQAQSL
GTTYIYDIPEMFRQSLIKLWESMSTQAFLPSPPLPSDMLTYTELVLDDQGQLVHMNRLPGG
NEIGMVAWKMTFKSPEYPEGRDIIVIGNDITYRIGSFGPQEDLLFLRASELARAEGIPRIYVSA
NSGARIGLAEEIRHMFHVAWVDPEDPYKGYRYLYLTPQDYKRVSALNSVHCEHVEDEGES
RYKITDIIGKEEGIGPENLRGSGMIAGESSLAYNEIITISLVTCRAIGIGAYLVRLGQRTIQVENS
HLILTGAGALNKVLGREVYTSNNQLGGIQIMHNNGVTHCTVCDDFEGVFTVLHWLSYMPKS
VHSSVPLLNSKDPIDRIIEFVPTKTPYDPRWMLAGRPHPTQKGQWLSGFFDYGSFSEIMQP
WAQTVVVGRARLGGIPVGVVAVETRTVELSIPADPANLDSEAKIIQQAGQVWFPDSAFKTY
QAIKDFNREGLPLMVFANWRGFSGGMKDMYDQVLKFGAYIVDGLRECCQPVLVYIPPQAE

FIGURE 1 (Continued)

LRGGSWVVIDSSINPRHMEMYADRESRGSVLEPEGTVEIKFRRKDLVKTMRRVDPVYIHLA
ERLGTPELSTAERKELENKLKEREEFLIPIYHQVAVQFADLHDTPGRMQEKGVISDILDWKT
SRTFFYWRLRRLLLEDLVKKKIHNANPELTDGQIQAMLRRWFVEVEGTVKAYVWDNNKDLA
EWLEKQLTEEDGVHSVIEENIKCISRDYVLKQIRSLVQANPEVAMDSIIHMTQHISPTQRAEVI
RILSTMDSPST

FIGURE 2

SEQ. ID NO. 2:

MVLLLCLSCLIFSCLTFSWLKIWGKMTDSKPITKSKSEANLIPSQEPFPASDNSGETPQRNG
EGHTLPKTPSQAEPASHKGPKDAGRRRNSLPPSHQKPPRNPLSSSDAAPSPELQANGTGT
QGLEATDTNGLSSSARPQGQQAGSPSKEDKKQANIKRQLMTNFILGSFDDYSSDEDSVAG
SSRESTRKGSRASLGALSLEAYLTTGEAETRVPTMRPSMSGLHLVKRGREHKKLDLHRDFT
VASPAEFVTRFGGDRVIEKVLIANNGIAAVKCMRSIRRWAYEMFRNERAIRFVVMVTPEDLK
ANAEYIKMADHYVPVPGGPNNNNYANVELIVDIAKRIPVQAVWAGWGHASENPKLPELLCK
NGVAFLGPPSEAMWALGDKIASTVVAQTLQVPTLPWSGSGLTVEWTEDDLQQGKRISVPE
DVYDKGCVKDVDEGLEAAERIGFPLMIKASEGGGGKGIRKAESAEDFPILFRQVQSEIPGSP
IFLMKLAQHARHLEVQILADQYGNAVSLFGRDCSIQRRHQKIVEEAPATIAPLAIFEFMEQCAI
RLAKTVGYVSAGTVEYLYSQDGSFHFLELNPRLQVEHPCTEMIADVNLPAAQLQIAMGVPL
HRLKDIRLLYGESPWGVTPISFETPSNPPLARGHVIAARITSENPDEGFKPSSGTVQELNFR
SSKNVWGYFSVAATGGLHEFADSQFGHCFSWGENREEAISNMVVALKELSIRGDFRTTVE
YLINLLETESFQNNDIDTGWLDYLIAEKVQAEKPDIMLGVVCGALNVADAMFRTCMTDFLHS
LERGQVLPADSLLNLVDVELIYGGVKYILKVARQSLTMFVLIMNGCHIEIDAHRLNDGGLLLS
YNGNSYTTYMKEEVDSYRITIGNKTCVFEKENDPTVLRSPSAGKLTQYTVEDGGHVEAGSS
YAEMEVMKMIMTLNVQERGRVKYIKRPGAVLEAGCVVARLELDDPSKVHPAEPFTGELPAQ
QTLPILGEKLHQVFHSVLENLTNVMSGFCLPEPVFSIKLKEWVQKLMMTLRHPSLPLLELQEI
MTSVAGRIPAPVEKSVRRVMAQYASNITSVLCQFPSQQIATILDCHAATLQRKADREVFFINT
QSIVQLVQRYRSGIRGYMKTVVLDLLRRYLRVEHHFQQAHYDKCVINLREQFKPDMSQVLD
CIFSHAQVAKKNQLVIMLIDELCGPDPSLSDELISILNELTQLSKSEHCKVALRARQILIASHLP
SYELRHNQVESIFLSAIDMYGHQFCPENLKKLILSETTIFDVLPTFFYHANKVVCMASLEVYV
RRGYIAYELNSLQHRQLPDGTCVVEFQFMLPSSHPNRMTVPISITNPDLLRHSTELFMDSGF
SPLCQRMGAMVAFRRFEDFTRNFDEVISCFANVPKDTPLFSEARTSLYSEDDCKSLREEPI
HILNVSIQCADHLEDEALVPILRTFVQSKKNILVDYGLRRITFLIAQEKEFPKFFTFRARDEFAE
DRIYRHLEPALAFQLELNRMRNFDLTAVPCANHKMHLYLGAAKVKEGVEVTDHRFFIRAIIR
HSDLITKEASFEYLQNEGERLLLEAMDELEVAFNNTSVRTDCNHIFLNFVPTVIMDPFKIEES
VRYMVMRYGSRLWKLRVLQAEVKINIRQTTTGSAVPIRLFITNESGYYLDISLYKEVTDSRSG
NIMFHSFGNKQGPQHGMLINTPYVTKDLLQAKRFQAQTLGTTYIYDFPEMFRQALFKLWGS
PDKYPKDILTYTELVLDSQGQLVEMNRLPGGNEVGMVAFKMRFKTQEYPEGRDVIVIGNDIT
FRIGSFGPGEDLLYLRASEMARAEGIPKIYVAANSGARIGMAEEIKHMFHVAWVDPEDPHK
GFKYLYLTPQDYTRISSLNSVHCKHIEEGGESRYMITDIIGKDDGLGVENLRGSGMIAGESSL
AYEEIVTISLVTCRAIGIGAYLVRLGQRVIQVENSHIILTGASALNKVLGREVYTSNNQLGGVQI
MHYNGVSHITVPDDFEGVYTILEWLSYMPKDNHSPVPIITPTDPIDREIEFLPSRAPYDPRW

FIGURE 2 (Continued)

MLAGRPHPTLKGTWQSGFFDHGSFKEIMAPWAQTVVTGRARLGGIPVGVIAVETRTVEVA
VPADPANLDSEAKIIQQAGQVWFPDSAYKTAQAIKDFNREKLPLMIFANWRGFSGGMKDMY
DQVLKFGAYIVDGLRQYKQPILIYIPPYAELRGGSWVVIDATINPLCIEMYADKESRGGVLEP
EGTVEIKFRKKDLIKSMRRIDPAYKKLMEQLGEPDLSDKDRKDLEGRLKAREDLLLPIYHQVA
VQFADFHDTPGRMLEKGVISDILEWKTARTFLYWRLRRLLEDQVKQEILQASGELSHVHIQ
SMLRRWFVETEGAVKAYLWDNNQVVVQWLEQHWQAGDGPRSTIRENITYLKHDSVLKTIR
GLVEENPEVAVDCVIYLSQHISPAERAQVVHLLSTMDSPAST

SEQUENCE LISTING

<160> NUMBER OF SEQ ID NOS: 2

<210> SEQ ID NO 1
<211> LENGTH: 2356
<212> TYPE: PRT
<213> ORGANISM: Homo sapiens

<400> SEQUENCE: 1

```
Met Ala His His His His His Asp Glu Val Asp Asp Glu Pro Ser
1               5                   10                  15

Pro Leu Ala Gln Pro Leu Glu Leu Asn Gln His Ser Arg Phe Ile Ile
            20                  25                  30

Gly Ser Val Ser Glu Asp Asn Ser Glu Asp Glu Ile Ser Asn Leu Val
                35                  40                  45

Lys Leu Asp Leu Leu Glu Lys Glu Gly Ser Leu Ser Pro Ala Ser Val
        50                  55                  60

Gly Ser Asp Thr Leu Ser Asp Leu Gly Ile Ser Ser Leu Gln Asp Gly
65                  70                  75                  80

Leu Ala Leu His Ile Arg Ser Ser Met Ser Gly Leu His Leu Val Lys
                85                  90                  95

Gln Gly Arg Asp Arg Lys Lys Ile Asp Ser Gln Arg Asp Phe Thr Val
            100                 105                 110

Ala Ser Pro Ala Glu Phe Val Thr Arg Phe Gly Gly Asn Lys Val Ile
        115                 120                 125

Glu Lys Val Leu Ile Ala Asn Asn Gly Ile Ala Ala Val Lys Cys Met
130                 135                 140

Arg Ser Ile Arg Arg Trp Ser Tyr Glu Met Phe Arg Asn Glu Arg Ala
145                 150                 155                 160

Ile Arg Phe Val Val Met Val Thr Pro Glu Asp Leu Lys Ala Asn Ala
                165                 170                 175

Glu Tyr Ile Lys Met Ala Asp His Tyr Val Pro Val Pro Gly Gly Pro
            180                 185                 190

Asn Asn Asn Asn Tyr Ala Asn Val Glu Leu Ile Leu Asp Ile Ala Lys
        195                 200                 205

Arg Ile Pro Val Gln Ala Val Trp Ala Gly Trp Gly His Ala Ser Glu
210                 215                 220

Asn Pro Lys Leu Pro Glu Leu Leu Lys Asn Gly Ile Ala Phe Met
225                 230                 235                 240

Gly Pro Pro Ser Gln Ala Met Trp Ala Leu Gly Asp Lys Ile Ala Ser
                245                 250                 255

Ser Ile Val Ala Gln Thr Ala Gly Ile Pro Thr Leu Pro Trp Ser Gly
            260                 265                 270

Ser Gly Leu Arg Val Asp Trp Gln Glu Asn Asp Phe Ser Lys Arg Ile
        275                 280                 285

Leu Asn Val Pro Gln Glu Leu Tyr Glu Lys Gly Tyr Val Lys Asp Val
290                 295                 300

Asp Asp Gly Leu Gln Ala Ala Glu Glu Val Gly Tyr Pro Val Met Ile
305                 310                 315                 320

Lys Ala Ser Glu Gly Gly Gly Gly Lys Gly Ile Arg Lys Val Asn Asn
                325                 330                 335

Ala Asp Asp Phe Pro Asn Leu Phe Arg Gln Val Gln Ala Glu Val Pro
            340                 345                 350

Gly Ser Pro Ile Phe Val Met Arg Leu Ala Lys Gln Ser Arg His Leu
        355                 360                 365

Glu Val Gln Ile Leu Ala Asp Gln Tyr Gly Asn Ala Ile Ser Leu Phe
370                 375                 380

Gly Arg Asp Cys Ser Val Gln Arg Arg His Gln Lys Ile Ile Glu Glu
385                 390                 395                 400

Ala Pro Ala Thr Ile Ala Thr Pro Ala Val Phe Glu His Met Glu Gln
                405                 410                 415
```

-continued

Cys Ala Val Lys Leu Ala Lys Met Val Gly Tyr Val Ser Ala Gly Thr
            420                 425                 430

Val Glu Tyr Leu Tyr Ser Gln Asp Gly Ser Phe Tyr Phe Leu Glu Leu
        435                 440                 445

Asn Pro Arg Leu Gln Val Glu His Pro Cys Thr Glu Met Val Ala Asp
    450                 455                 460

Val Asn Leu Pro Ala Ala Gln Leu Gln Ile Ala Met Gly Ile Pro Leu
465                 470                 475                 480

Tyr Arg Ile Lys Asp Ile Arg Met Met Tyr Gly Val Ser Pro Trp Gly
                485                 490                 495

Asp Ser Pro Ile Asp Phe Glu Asp Ser Ala His Val Pro Cys Pro Arg
            500                 505                 510

Gly His Val Ile Ala Ala Arg Ile Thr Ser Glu Asn Pro Asp Glu Gly
        515                 520                 525

Phe Lys Pro Ser Ser Gly Thr Val Gln Glu Leu Asn Phe Arg Ser Asn
    530                 535                 540

Lys Asn Val Trp Gly Tyr Phe Ser Val Ala Ala Gly Gly Leu His
545                 550                 555                 560

Glu Phe Ala Asp Ser Gln Phe Gly His Cys Phe Ser Trp Gly Glu Asn
                565                 570                 575

Arg Glu Glu Ala Ile Ser Asn Met Val Val Ala Leu Lys Glu Leu Ser
            580                 585                 590

Ile Arg Gly Asp Phe Arg Thr Val Glu Tyr Leu Ile Lys Leu Leu
        595                 600                 605

Glu Thr Glu Ser Phe Gln Met Asn Arg Ile Asp Thr Gly Trp Leu Asp
    610                 615                 620

Arg Leu Ile Ala Glu Lys Val Gln Ala Glu Arg Pro Asp Thr Met Leu
625                 630                 635                 640

Gly Val Val Cys Gly Ala Leu His Val Ala Asp Val Ser Leu Arg Asn
                645                 650                 655

Ser Val Ser Asn Phe Leu His Ser Leu Glu Arg Gly Gln Val Leu Pro
            660                 665                 670

Ala His Thr Leu Leu Asn Thr Val Asp Val Glu Leu Ile Tyr Glu Gly
        675                 680                 685

Val Lys Tyr Val Leu Lys Val Thr Arg Gln Ser Pro Asn Ser Tyr Val
    690                 695                 700

Val Ile Met Asn Gly Ser Cys Val Glu Val Asp Val His Arg Leu Ser
705                 710                 715                 720

Asp Gly Gly Leu Leu Leu Ser Tyr Asp Gly Ser Ser Tyr Thr Thr Tyr
                725                 730                 735

Met Lys Glu Glu Val Asp Arg Tyr Arg Ile Thr Ile Gly Asn Lys Thr
            740                 745                 750

Cys Val Phe Glu Lys Glu Asn Asp Pro Ser Val Met Arg Ser Pro Ser
        755                 760                 765

Ala Gly Lys Leu Ile Gln Tyr Ile Val Glu Asp Gly Gly His Val Phe
    770                 775                 780

Ala Gly Gln Cys Tyr Ala Glu Ile Glu Val Met Lys Met Val Met Thr
785                 790                 795                 800

Leu Thr Ala Val Glu Ser Gly Cys Ile His Tyr Val Lys Arg Pro Gly
                805                 810                 815

Ala Ala Leu Asp Pro Gly Cys Val Leu Ala Lys Met Gln Leu Asp Asn
            820                 825                 830

```
Pro Ser Lys Val Gln Gln Ala Glu Leu His Thr Gly Ser Leu Pro Arg
    835                 840                 845

Ile Gln Ser Thr Ala Leu Arg Gly Glu Lys Leu His Arg Val Phe His
    850                 855                 860

Tyr Val Leu Asp Asn Leu Val Asn Val Met Asn Gly Tyr Cys Leu Pro
865                 870                 875                 880

Asp Pro Phe Phe Ser Ser Lys Val Lys Asp Trp Val Glu Arg Leu Met
            885                 890                 895

Lys Thr Leu Arg Asp Pro Ser Leu Pro Leu Leu Glu Leu Gln Asp Ile
            900                 905                 910

Met Thr Ser Val Ser Gly Arg Ile Pro Pro Asn Val Glu Lys Ser Ile
            915                 920                 925

Lys Lys Glu Met Ala Gln Tyr Ala Ser Asn Ile Thr Ser Val Leu Cys
930                 935                 940

Gln Phe Pro Ser Gln Gln Ile Ala Asn Ile Leu Asp Ser His Ala Ala
945                 950                 955                 960

Thr Leu Asn Arg Lys Ser Glu Arg Glu Val Phe Phe Met Asn Thr Gln
            965                 970                 975

Ser Ile Val Gln Leu Val Gln Arg Tyr Arg Ser Gly Ile Arg Gly His
            980                 985                 990

Met Lys Ala Val Val Met Asp Leu Leu Arg Gln Tyr Leu Arg Val Glu
        995                 1000                1005

Thr Gln Phe Gln Asn Gly His Tyr Asp Lys Cys Val Phe Ala Leu
    1010                1015                1020

Arg Glu Glu Asn Lys Ser Asp Met Asn Thr Val Leu Asn Tyr Ile
    1025                1030                1035

Phe Ser His Ala Gln Val Thr Lys Lys Asn Leu Leu Val Thr Met
    1040                1045                1050

Leu Ile Asp Gln Leu Cys Gly Arg Asp Pro Thr Leu Thr Asp Glu
    1055                1060                1065

Leu Leu Asn Ile Leu Thr Glu Leu Thr Gln Leu Ser Lys Thr Thr
    1070                1075                1080

Asn Ala Lys Val Ala Leu Arg Ala Arg Gln Val Leu Ile Ala Ser
    1085                1090                1095

His Leu Pro Ser Tyr Glu Leu Arg His Asn Gln Val Glu Ser Ile
    1100                1105                1110

Phe Leu Ser Ala Ile Asp Met Tyr Gly His Gln Phe Cys Ile Glu
    1115                1120                1125

Asn Leu Gln Lys Leu Ile Leu Ser Glu Thr Ser Ile Phe Asp Val
    1130                1135                1140

Leu Pro Asn Phe Phe Tyr His Ser Asn Gln Val Val Arg Met Ala
    1145                1150                1155

Ala Leu Glu Val Tyr Val Arg Arg Ala Tyr Ile Ala Tyr Glu Leu
    1160                1165                1170

Asn Ser Val Gln His Arg Gln Leu Lys Asp Asn Thr Cys Val Val
    1175                1180                1185

Glu Phe Gln Phe Met Leu Pro Thr Ser His Pro Asn Arg Gly Asn
    1190                1195                1200

Ile Pro Thr Leu Asn Arg Met Ser Phe Ser Ser Asn Leu Asn His
    1205                1210                1215

Tyr Gly Met Thr His Val Ala Ser Val Ser Asp Val Leu Leu Asp
    1220                1225                1230
```

```
Asn Ser Phe Thr Pro Pro Cys Gln Arg Met Gly Gly Met Val Ser
1235                1240                1245

Phe Arg Thr Phe Glu Asp Phe Val Arg Ile Phe Asp Glu Val Met
1250                1255                1260

Gly Cys Phe Ser Asp Ser Pro Pro Gln Ser Pro Thr Phe Pro Glu
1265                1270                1275

Ala Gly His Thr Ser Leu Tyr Asp Glu Asp Lys Val Pro Arg Asp
1280                1285                1290

Glu Pro Ile His Ile Leu Asn Val Ala Ile Lys Thr Asp Cys Asp
1295                1300                1305

Ile Glu Asp Asp Arg Leu Ala Ala Met Phe Arg Glu Phe Thr Gln
1310                1315                1320

Gln Asn Lys Ala Thr Leu Val Asp His Gly Ile Arg Arg Leu Thr
1325                1330                1335

Phe Leu Val Ala Gln Lys Asp Phe Arg Lys Gln Val Asn Tyr Glu
1340                1345                1350

Val Asp Arg Arg Phe His Arg Glu Phe Pro Lys Phe Phe Thr Phe
1355                1360                1365

Arg Ala Arg Asp Lys Phe Glu Glu Asp Arg Ile Tyr Arg His Leu
1370                1375                1380

Glu Pro Ala Leu Ala Phe Gln Leu Glu Leu Asn Arg Met Arg Asn
1385                1390                1395

Phe Asp Leu Thr Ala Ile Pro Cys Ala Asn His Lys Met His Leu
1400                1405                1410

Tyr Leu Gly Ala Ala Lys Val Glu Val Gly Thr Glu Val Thr Asp
1415                1420                1425

Tyr Arg Phe Phe Val Arg Ala Ile Ile Arg His Ser Asp Leu Val
1430                1435                1440

Thr Lys Glu Ala Ser Phe Glu Tyr Leu Gln Asn Glu Gly Glu Arg
1445                1450                1455

Leu Leu Leu Glu Ala Met Asp Glu Leu Glu Val Ala Phe Asn Asn
1460                1465                1470

Thr Asn Val Arg Thr Asp Cys Asn His Ile Phe Leu Asn Phe Val
1475                1480                1485

Pro Thr Val Ile Met Asp Pro Ser Lys Ile Glu Glu Ser Val Arg
1490                1495                1500

Ser Met Val Met Arg Tyr Gly Ser Arg Leu Trp Lys Leu Arg Val
1505                1510                1515

Leu Gln Ala Glu Leu Lys Ile Asn Ile Arg Leu Thr Pro Thr Gly
1520                1525                1530

Lys Ala Ile Pro Ile Arg Leu Phe Leu Thr Asn Glu Ser Gly Tyr
1535                1540                1545

Tyr Leu Asp Ile Ser Leu Tyr Lys Glu Val Thr Asp Ser Arg Thr
1550                1555                1560

Ala Gln Ile Met Phe Gln Ala Tyr Gly Asp Lys Gln Gly Pro Leu
1565                1570                1575

His Gly Met Leu Ile Asn Thr Pro Tyr Val Thr Lys Asp Leu Leu
1580                1585                1590

Gln Ser Lys Arg Phe Gln Ala Gln Ser Leu Gly Thr Thr Tyr Ile
1595                1600                1605

Tyr Asp Ile Pro Glu Met Phe Arg Gln Ser Leu Ile Lys Leu Trp
1610                1615                1620
```

```
Glu  Ser  Met  Ser  Thr  Gln  Ala  Phe  Leu  Pro  Ser  Pro  Pro  Leu  Pro
     1625                1630                     1635

Ser  Asp  Met  Leu  Thr  Tyr  Thr  Glu  Leu  Val  Leu  Asp  Asp  Gln  Gly
     1640                1645                     1650

Gln  Leu  Val  His  Met  Asn  Arg  Leu  Pro  Gly  Gly  Asn  Glu  Ile  Gly
     1655                1660                     1665

Met  Val  Ala  Trp  Lys  Met  Thr  Phe  Lys  Ser  Pro  Glu  Tyr  Pro  Glu
     1670                1675                     1680

Gly  Arg  Asp  Ile  Ile  Val  Ile  Gly  Asn  Asp  Ile  Thr  Tyr  Arg  Ile
     1685                1690                     1695

Gly  Ser  Phe  Gly  Pro  Gln  Glu  Asp  Leu  Leu  Phe  Leu  Arg  Ala  Ser
     1700                1705                     1710

Glu  Leu  Ala  Arg  Ala  Glu  Gly  Ile  Pro  Arg  Ile  Tyr  Val  Ser  Ala
     1715                1720                     1725

Asn  Ser  Gly  Ala  Arg  Ile  Gly  Leu  Ala  Glu  Glu  Ile  Arg  His  Met
     1730                1735                     1740

Phe  His  Val  Ala  Trp  Val  Asp  Pro  Glu  Asp  Pro  Tyr  Lys  Gly  Tyr
     1745                1750                     1755

Arg  Tyr  Leu  Tyr  Leu  Thr  Pro  Gln  Asp  Tyr  Lys  Arg  Val  Ser  Ala
     1760                1765                     1770

Leu  Asn  Ser  Val  His  Cys  Glu  His  Val  Glu  Asp  Glu  Gly  Glu  Ser
     1775                1780                     1785

Arg  Tyr  Lys  Ile  Thr  Asp  Ile  Ile  Gly  Lys  Glu  Glu  Gly  Ile  Gly
     1790                1795                     1800

Pro  Glu  Asn  Leu  Arg  Gly  Ser  Gly  Met  Ile  Ala  Gly  Glu  Ser  Ser
     1805                1810                     1815

Leu  Ala  Tyr  Asn  Glu  Ile  Ile  Thr  Ile  Ser  Leu  Val  Thr  Cys  Arg
     1820                1825                     1830

Ala  Ile  Gly  Ile  Gly  Ala  Tyr  Leu  Val  Arg  Leu  Gly  Gln  Arg  Thr
     1835                1840                     1845

Ile  Gln  Val  Glu  Asn  Ser  His  Leu  Ile  Leu  Thr  Gly  Ala  Gly  Ala
     1850                1855                     1860

Leu  Asn  Lys  Val  Leu  Gly  Arg  Glu  Val  Tyr  Thr  Ser  Asn  Asn  Gln
     1865                1870                     1875

Leu  Gly  Gly  Ile  Gln  Ile  Met  His  Asn  Asn  Gly  Val  Thr  His  Cys
     1880                1885                     1890

Thr  Val  Cys  Asp  Asp  Phe  Glu  Gly  Val  Phe  Thr  Val  Leu  His  Trp
     1895                1900                     1905

Leu  Ser  Tyr  Met  Pro  Lys  Ser  Val  His  Ser  Ser  Val  Pro  Leu  Leu
     1910                1915                     1920

Asn  Ser  Lys  Asp  Pro  Ile  Asp  Arg  Ile  Ile  Glu  Phe  Val  Pro  Thr
     1925                1930                     1935

Lys  Thr  Pro  Tyr  Asp  Pro  Arg  Trp  Met  Leu  Ala  Gly  Arg  Pro  His
     1940                1945                     1950

Pro  Thr  Gln  Lys  Gly  Gln  Trp  Leu  Ser  Gly  Phe  Phe  Asp  Tyr  Gly
     1955                1960                     1965

Ser  Phe  Ser  Glu  Ile  Met  Gln  Pro  Trp  Ala  Gln  Thr  Val  Val  Val
     1970                1975                     1980

Gly  Arg  Ala  Arg  Leu  Gly  Gly  Ile  Pro  Val  Gly  Val  Val  Ala  Val
     1985                1990                     1995

Glu  Thr  Arg  Thr  Val  Glu  Leu  Ser  Ile  Pro  Ala  Asp  Pro  Ala  Asn
     2000                2005                     2010
```

```
Leu Asp Ser Glu Ala Lys Ile Ile Gln Gln Ala Gly Gln Val Trp
2015                2020                2025

Phe Pro Asp Ser Ala Phe Lys Thr Tyr Gln Ala Ile Lys Asp Phe
2030                2035                2040

Asn Arg Glu Gly Leu Pro Leu Met Val Phe Ala Asn Trp Arg Gly
2045                2050                2055

Phe Ser Gly Gly Met Lys Asp Met Tyr Asp Gln Val Leu Lys Phe
2060                2065                2070

Gly Ala Tyr Ile Val Asp Gly Leu Arg Glu Cys Cys Gln Pro Val
2075                2080                2085

Leu Val Tyr Ile Pro Pro Gln Ala Glu Leu Arg Gly Gly Ser Trp
2090                2095                2100

Val Val Ile Asp Ser Ser Ile Asn Pro Arg His Met Glu Met Tyr
2105                2110                2115

Ala Asp Arg Glu Ser Arg Gly Ser Val Leu Glu Pro Glu Gly Thr
2120                2125                2130

Val Glu Ile Lys Phe Arg Arg Lys Asp Leu Val Lys Thr Met Arg
2135                2140                2145

Arg Val Asp Pro Val Tyr Ile His Leu Ala Glu Arg Leu Gly Thr
2150                2155                2160

Pro Glu Leu Ser Thr Ala Glu Arg Lys Glu Leu Glu Asn Lys Leu
2165                2170                2175

Lys Glu Arg Glu Glu Phe Leu Ile Pro Ile Tyr His Gln Val Ala
2180                2185                2190

Val Gln Phe Ala Asp Leu His Asp Thr Pro Gly Arg Met Gln Glu
2195                2200                2205

Lys Gly Val Ile Ser Asp Ile Leu Asp Trp Lys Thr Ser Arg Thr
2210                2215                2220

Phe Phe Tyr Trp Arg Leu Arg Arg Leu Leu Leu Glu Asp Leu Val
2225                2230                2235

Lys Lys Lys Ile His Asn Ala Asn Pro Glu Leu Thr Asp Gly Gln
2240                2245                2250

Ile Gln Ala Met Leu Arg Arg Trp Phe Val Glu Val Glu Gly Thr
2255                2260                2265

Val Lys Ala Tyr Val Trp Asp Asn Asn Lys Asp Leu Ala Glu Trp
2270                2275                2280

Leu Glu Lys Gln Leu Thr Glu Glu Asp Gly Val His Ser Val Ile
2285                2290                2295

Glu Glu Asn Ile Lys Cys Ile Ser Arg Asp Tyr Val Leu Lys Gln
2300                2305                2310

Ile Arg Ser Leu Val Gln Ala Asn Pro Glu Val Ala Met Asp Ser
2315                2320                2325

Ile Ile His Met Thr Gln His Ile Ser Pro Thr Gln Arg Ala Glu
2330                2335                2340

Val Ile Arg Ile Leu Ser Thr Met Asp Ser Pro Ser Thr
2345                2350                2355

<210> SEQ ID NO 2
<211> LENGTH: 2458
<212> TYPE: PRT
<213> ORGANISM: Homo sapiens
```

```
<400> SEQUENCE: 2

Met Val Leu Leu Leu Cys Leu Ser Cys Leu Ile Phe Ser Cys Leu Thr
1               5                   10                  15

Phe Ser Trp Leu Lys Ile Trp Gly Lys Met Thr Asp Ser Lys Pro Ile
            20                  25                  30

Thr Lys Ser Lys Ser Glu Ala Asn Leu Ile Pro Ser Gln Glu Pro Phe
        35                  40                  45

Pro Ala Ser Asp Asn Ser Gly Glu Thr Pro Gln Arg Asn Gly Glu Gly
    50                  55                  60

His Thr Leu Pro Lys Thr Pro Ser Gln Ala Glu Pro Ala Ser His Lys
65                  70                  75                  80

Gly Pro Lys Asp Ala Gly Arg Arg Asn Ser Leu Pro Pro Ser His
                85                  90                  95

Gln Lys Pro Pro Arg Asn Pro Leu Ser Ser Ser Asp Ala Ala Pro Ser
                100                 105                 110

Pro Glu Leu Gln Ala Asn Gly Thr Gly Thr Gln Gly Leu Glu Ala Thr
            115                 120                 125

Asp Thr Asn Gly Leu Ser Ser Ser Ala Arg Pro Gln Gly Gln Gln Ala
    130                 135                 140

Gly Ser Pro Ser Lys Glu Asp Lys Lys Gln Ala Asn Ile Lys Arg Gln
145                 150                 155                 160

Leu Met Thr Asn Phe Ile Leu Gly Ser Phe Asp Asp Tyr Ser Ser Asp
                165                 170                 175

Glu Asp Ser Val Ala Gly Ser Ser Arg Glu Ser Thr Arg Lys Gly Ser
            180                 185                 190

Arg Ala Ser Leu Gly Ala Leu Ser Leu Glu Ala Tyr Leu Thr Thr Gly
        195                 200                 205

Glu Ala Glu Thr Arg Val Pro Thr Met Arg Pro Ser Met Ser Gly Leu
    210                 215                 220

His Leu Val Lys Arg Gly Arg Glu His Lys Lys Leu Asp Leu His Arg
225                 230                 235                 240

Asp Phe Thr Val Ala Ser Pro Ala Glu Phe Val Thr Arg Phe Gly Gly
                245                 250                 255

Asp Arg Val Ile Glu Lys Val Leu Ile Ala Asn Asn Gly Ile Ala Ala
            260                 265                 270

Val Lys Cys Met Arg Ser Ile Arg Arg Trp Ala Tyr Glu Met Phe Arg
        275                 280                 285

Asn Glu Arg Ala Ile Arg Phe Val Val Met Val Thr Pro Glu Asp Leu
    290                 295                 300

Lys Ala Asn Ala Glu Tyr Ile Lys Met Ala Asp His Tyr Val Pro Val
305                 310                 315                 320

Pro Gly Gly Pro Asn Asn Asn Asn Tyr Ala Asn Val Glu Leu Ile Val
                325                 330                 335

Asp Ile Ala Lys Arg Ile Pro Val Gln Ala Val Trp Ala Gly Trp Gly
            340                 345                 350

His Ala Ser Glu Asn Pro Lys Leu Pro Glu Leu Leu Cys Lys Asn Gly
        355                 360                 365

Val Ala Phe Leu Gly Pro Pro Ser Glu Ala Met Trp Ala Leu Gly Asp
    370                 375                 380

Lys Ile Ala Ser Thr Val Val Ala Gln Thr Leu Gln Val Pro Thr Leu
385                 390                 395                 400

Pro Trp Ser Gly Ser Gly Leu Thr Val Glu Trp Thr Glu Asp Asp Leu
                405                 410                 415
```

```
Gln Gln Gly Lys Arg Ile Ser Val Pro Glu Asp Val Tyr Asp Lys Gly
                420                 425                 430

Cys Val Lys Asp Val Asp Glu Gly Leu Glu Ala Ala Glu Arg Ile Gly
            435                 440                 445

Phe Pro Leu Met Ile Lys Ala Ser Glu Gly Gly Gly Lys Gly Ile
450                 455                 460

Arg Lys Ala Glu Ser Ala Glu Asp Phe Pro Ile Leu Phe Arg Gln Val
465                 470                 475                 480

Gln Ser Glu Ile Pro Gly Ser Pro Ile Phe Leu Met Lys Leu Ala Gln
                485                 490                 495

His Ala Arg His Leu Glu Val Gln Ile Leu Ala Asp Gln Tyr Gly Asn
            500                 505                 510

Ala Val Ser Leu Phe Gly Arg Asp Cys Ser Ile Gln Arg Arg His Gln
        515                 520                 525

Lys Ile Val Glu Glu Ala Pro Ala Thr Ile Ala Pro Leu Ala Ile Phe
530                 535                 540

Glu Phe Met Glu Gln Cys Ala Ile Arg Leu Ala Lys Thr Val Gly Tyr
545                 550                 555                 560

Val Ser Ala Gly Thr Val Glu Tyr Leu Tyr Ser Gln Asp Gly Ser Phe
                565                 570                 575

His Phe Leu Glu Leu Asn Pro Arg Leu Gln Val Glu His Pro Cys Thr
            580                 585                 590

Glu Met Ile Ala Asp Val Asn Leu Pro Ala Ala Gln Leu Gln Ile Ala
        595                 600                 605

Met Gly Val Pro Leu His Arg Leu Lys Asp Ile Arg Leu Leu Tyr Gly
610                 615                 620

Glu Ser Pro Trp Gly Val Thr Pro Ile Ser Phe Glu Thr Pro Ser Asn
625                 630                 635                 640

Pro Pro Leu Ala Arg Gly His Val Ile Ala Ala Arg Ile Thr Ser Glu
                645                 650                 655

Asn Pro Asp Glu Gly Phe Lys Pro Ser Ser Gly Thr Val Gln Glu Leu
            660                 665                 670

Asn Phe Arg Ser Ser Lys Asn Val Trp Gly Tyr Phe Ser Val Ala Ala
        675                 680                 685

Thr Gly Gly Leu His Glu Phe Ala Asp Ser Gln Phe Gly His Cys Phe
690                 695                 700

Ser Trp Gly Glu Asn Arg Glu Glu Ala Ile Ser Asn Met Val Val Ala
705                 710                 715                 720

Leu Lys Glu Leu Ser Ile Arg Gly Asp Phe Arg Thr Thr Val Glu Tyr
                725                 730                 735

Leu Ile Asn Leu Leu Glu Thr Glu Ser Phe Gln Asn Asn Asp Ile Asp
            740                 745                 750

Thr Gly Trp Leu Asp Tyr Leu Ile Ala Glu Lys Val Gln Ala Glu Lys
        755                 760                 765

Pro Asp Ile Met Leu Gly Val Val Cys Gly Ala Leu Asn Val Ala Asp
770                 775                 780

Ala Met Phe Arg Thr Cys Met Thr Asp Phe Leu His Ser Leu Glu Arg
785                 790                 795                 800

Gly Gln Val Leu Pro Ala Asp Ser Leu Leu Asn Leu Val Asp Val Glu
                805                 810                 815

Leu Ile Tyr Gly Gly Val Lys Tyr Ile Leu Lys Val Ala Arg Gln Ser
            820                 825                 830
```

```
Leu Thr Met Phe Val Leu Ile Met Asn Gly Cys His Ile Glu Ile Asp
            835                 840                 845

Ala His Arg Leu Asn Asp Gly Gly Leu Leu Ser Tyr Asn Gly Asn
        850                 855                 860

Ser Tyr Thr Thr Tyr Met Lys Glu Val Asp Ser Tyr Arg Ile Thr
865                 870                 875                 880

Ile Gly Asn Lys Thr Cys Val Phe Glu Lys Glu Asn Asp Pro Thr Val
                885                 890                 895

Leu Arg Ser Pro Ser Ala Gly Lys Leu Thr Gln Tyr Thr Val Glu Asp
            900                 905                 910

Gly Gly His Val Glu Ala Gly Ser Ser Tyr Ala Glu Met Glu Val Met
        915                 920                 925

Lys Met Ile Met Thr Leu Asn Val Gln Glu Arg Gly Arg Val Lys Tyr
        930                 935                 940

Ile Lys Arg Pro Gly Ala Val Leu Glu Ala Gly Cys Val Val Ala Arg
945                 950                 955                 960

Leu Glu Leu Asp Asp Pro Ser Lys Val His Pro Ala Glu Pro Phe Thr
                965                 970                 975

Gly Glu Leu Pro Ala Gln Gln Thr Leu Pro Ile Leu Gly Glu Lys Leu
            980                 985                 990

His Gln Val Phe His Ser Val Leu Glu Asn Leu Thr Asn Val Met Ser
            995                1000                1005

Gly Phe Cys Leu Pro Glu Pro Val Phe Ser Ile Lys Leu Lys Glu
        1010                1015                1020

Trp Val Gln Lys Leu Met Met Thr Leu Arg His Pro Ser Leu Pro
1025                1030                1035

Leu Leu Glu Leu Gln Glu Ile Met Thr Ser Val Ala Gly Arg Ile
        1040                1045                1050

Pro Ala Pro Val Glu Lys Ser Val Arg Arg Val Met Ala Gln Tyr
        1055                1060                1065

Ala Ser Asn Ile Thr Ser Val Leu Cys Gln Phe Pro Ser Gln Gln
        1070                1075                1080

Ile Ala Thr Ile Leu Asp Cys His Ala Ala Thr Leu Gln Arg Lys
        1085                1090                1095

Ala Asp Arg Glu Val Phe Phe Ile Asn Thr Gln Ser Ile Val Gln
1100                1105                1110

Leu Val Gln Arg Tyr Arg Ser Gly Ile Arg Gly Tyr Met Lys Thr
        1115                1120                1125

Val Val Leu Asp Leu Leu Arg Arg Tyr Leu Arg Val Glu His His
        1130                1135                1140

Phe Gln Gln Ala His Tyr Asp Lys Cys Val Ile Asn Leu Arg Glu
        1145                1150                1155

Gln Phe Lys Pro Asp Met Ser Gln Val Leu Asp Cys Ile Phe Ser
        1160                1165                1170

His Ala Gln Val Ala Lys Lys Asn Gln Leu Val Ile Met Leu Ile
        1175                1180                1185

Asp Glu Leu Cys Gly Pro Asp Pro Ser Leu Ser Asp Glu Leu Ile
        1190                1195                1200

Ser Ile Leu Asn Glu Leu Thr Gln Leu Ser Lys Ser Glu His Cys
        1205                1210                1215

Lys Val Ala Leu Arg Ala Arg Gln Ile Leu Ile Ala Ser His Leu
        1220                1225                1230
```

```
Pro  Ser  Tyr  Glu  Leu  Arg  His  Asn  Gln  Val  Glu  Ser  Ile  Phe  Leu
1235                     1240                     1245

Ser  Ala  Ile  Asp  Met  Tyr  Gly  His  Gln  Phe  Cys  Pro  Glu  Asn  Leu
1250                     1255                     1260

Lys  Lys  Leu  Ile  Leu  Ser  Glu  Thr  Thr  Ile  Phe  Asp  Val  Leu  Pro
1265                     1270                     1275

Thr  Phe  Phe  Tyr  His  Ala  Asn  Lys  Val  Val  Cys  Met  Ala  Ser  Leu
1280                     1285                     1290

Glu  Val  Tyr  Val  Arg  Arg  Gly  Tyr  Ile  Ala  Tyr  Glu  Leu  Asn  Ser
1295                     1300                     1305

Leu  Gln  His  Arg  Gln  Leu  Pro  Asp  Gly  Thr  Cys  Val  Val  Glu  Phe
1310                     1315                     1320

Gln  Phe  Met  Leu  Pro  Ser  Ser  His  Pro  Asn  Arg  Met  Thr  Val  Pro
1325                     1330                     1335

Ile  Ser  Ile  Thr  Asn  Pro  Asp  Leu  Leu  Arg  His  Ser  Thr  Glu  Leu
1340                     1345                     1350

Phe  Met  Asp  Ser  Gly  Phe  Ser  Pro  Leu  Cys  Gln  Arg  Met  Gly  Ala
1355                     1360                     1365

Met  Val  Ala  Phe  Arg  Arg  Phe  Glu  Asp  Phe  Thr  Arg  Asn  Phe  Asp
1370                     1375                     1380

Glu  Val  Ile  Ser  Cys  Phe  Ala  Asn  Val  Pro  Lys  Asp  Thr  Pro  Leu
1385                     1390                     1395

Phe  Ser  Glu  Ala  Arg  Thr  Ser  Leu  Tyr  Ser  Glu  Asp  Asp  Cys  Lys
1400                     1405                     1410

Ser  Leu  Arg  Glu  Glu  Pro  Ile  His  Ile  Leu  Asn  Val  Ser  Ile  Gln
1415                     1420                     1425

Cys  Ala  Asp  His  Leu  Glu  Asp  Glu  Ala  Leu  Val  Pro  Ile  Leu  Arg
1430                     1435                     1440

Thr  Phe  Val  Gln  Ser  Lys  Lys  Asn  Ile  Leu  Val  Asp  Tyr  Gly  Leu
1445                     1450                     1455

Arg  Arg  Ile  Thr  Phe  Leu  Ile  Ala  Gln  Glu  Lys  Glu  Phe  Pro  Lys
1460                     1465                     1470

Phe  Phe  Thr  Phe  Arg  Ala  Arg  Asp  Glu  Phe  Ala  Glu  Asp  Arg  Ile
1475                     1480                     1485

Tyr  Arg  His  Leu  Glu  Pro  Ala  Leu  Ala  Phe  Gln  Leu  Glu  Leu  Asn
1490                     1495                     1500

Arg  Met  Arg  Asn  Phe  Asp  Leu  Thr  Ala  Val  Pro  Cys  Ala  Asn  His
1505                     1510                     1515

Lys  Met  His  Leu  Tyr  Leu  Gly  Ala  Ala  Lys  Val  Lys  Glu  Gly  Val
1520                     1525                     1530

Glu  Val  Thr  Asp  His  Arg  Phe  Phe  Ile  Arg  Ala  Ile  Ile  Arg  His
1535                     1540                     1545

Ser  Asp  Leu  Ile  Thr  Lys  Glu  Ala  Ser  Phe  Glu  Tyr  Leu  Gln  Asn
1550                     1555                     1560

Glu  Gly  Glu  Arg  Leu  Leu  Leu  Glu  Ala  Met  Asp  Glu  Leu  Glu  Val
1565                     1570                     1575

Ala  Phe  Asn  Asn  Thr  Ser  Val  Arg  Thr  Asp  Cys  Asn  His  Ile  Phe
1580                     1585                     1590

Leu  Asn  Phe  Val  Pro  Thr  Val  Ile  Met  Asp  Pro  Phe  Lys  Ile  Glu
1595                     1600                     1605

Glu  Ser  Val  Arg  Tyr  Met  Val  Met  Arg  Tyr  Gly  Ser  Arg  Leu  Trp
1610                     1615                     1620
```

```
Lys Leu Arg Val Leu Gln Ala Glu Val Lys Ile Asn Ile Arg Gln
    1625                1630                1635

Thr Thr Thr Gly Ser Ala Val Pro Ile Arg Leu Phe Ile Thr Asn
    1640                1645                1650

Glu Ser Gly Tyr Tyr Leu Asp Ile Ser Leu Tyr Lys Glu Val Thr
    1655                1660                1665

Asp Ser Arg Ser Gly Asn Ile Met Phe His Ser Phe Gly Asn Lys
    1670                1675                1680

Gln Gly Pro Gln His Gly Met Leu Ile Asn Thr Pro Tyr Val Thr
    1685                1690                1695

Lys Asp Leu Leu Gln Ala Lys Arg Phe Gln Ala Gln Thr Leu Gly
    1700                1705                1710

Thr Thr Tyr Ile Tyr Asp Phe Pro Glu Met Phe Arg Gln Ala Leu
    1715                1720                1725

Phe Lys Leu Trp Gly Ser Pro Asp Lys Tyr Pro Lys Asp Ile Leu
    1730                1735                1740

Thr Tyr Thr Glu Leu Val Leu Asp Ser Gln Gly Gln Leu Val Glu
    1745                1750                1755

Met Asn Arg Leu Pro Gly Gly Asn Glu Val Gly Met Val Ala Phe
    1760                1765                1770

Lys Met Arg Phe Lys Thr Gln Glu Tyr Pro Glu Gly Arg Asp Val
    1775                1780                1785

Ile Val Ile Gly Asn Asp Ile Thr Phe Arg Ile Gly Ser Phe Gly
    1790                1795                1800

Pro Gly Glu Asp Leu Leu Tyr Leu Arg Ala Ser Glu Met Ala Arg
    1805                1810                1815

Ala Glu Gly Ile Pro Lys Ile Tyr Val Ala Ala Asn Ser Gly Ala
    1820                1825                1830

Arg Ile Gly Met Ala Glu Glu Ile Lys His Met Phe His Val Ala
    1835                1840                1845

Trp Val Asp Pro Glu Asp Pro His Lys Gly Phe Lys Tyr Leu Tyr
    1850                1855                1860

Leu Thr Pro Gln Asp Tyr Thr Arg Ile Ser Ser Leu Asn Ser Val
    1865                1870                1875

His Cys Lys His Ile Glu Glu Gly Gly Glu Ser Arg Tyr Met Ile
    1880                1885                1890

Thr Asp Ile Ile Gly Lys Asp Asp Gly Leu Gly Val Glu Asn Leu
    1895                1900                1905

Arg Gly Ser Gly Met Ile Ala Gly Glu Ser Ser Leu Ala Tyr Glu
    1910                1915                1920

Glu Ile Val Thr Ile Ser Leu Val Thr Cys Arg Ala Ile Gly Ile
    1925                1930                1935

Gly Ala Tyr Leu Val Arg Leu Gly Gln Arg Val Ile Gln Val Glu
    1940                1945                1950

Asn Ser His Ile Ile Leu Thr Gly Ala Ser Ala Leu Asn Lys Val
    1955                1960                1965

Leu Gly Arg Glu Val Tyr Thr Ser Asn Asn Gln Leu Gly Gly Val
    1970                1975                1980

Gln Ile Met His Tyr Asn Gly Val Ser His Ile Thr Val Pro Asp
    1985                1990                1995

Asp Phe Glu Gly Val Tyr Thr Ile Leu Glu Trp Leu Ser Tyr Met
    2000                2005                2010
```

-continued

```
Pro Lys Asp Asn His Ser Pro Val Pro Ile Ile Thr Pro Thr Asp
2015                2020                2025

Pro Ile Asp Arg Glu Ile Glu Phe Leu Pro Ser Arg Ala Pro Tyr
2030                2035                2040

Asp Pro Arg Trp Met Leu Ala Gly Arg Pro His Pro Thr Leu Lys
2045                2050                2055

Gly Thr Trp Gln Ser Gly Phe Phe Asp His Gly Ser Phe Lys Glu
2060                2065                2070

Ile Met Ala Pro Trp Ala Gln Thr Val Val Thr Gly Arg Ala Arg
2075                2080                2085

Leu Gly Gly Ile Pro Val Gly Val Ile Ala Val Glu Thr Arg Thr
2090                2095                2100

Val Glu Val Ala Val Pro Ala Asp Pro Ala Asn Leu Asp Ser Glu
2105                2110                2115

Ala Lys Ile Ile Gln Gln Ala Gly Gln Val Trp Phe Pro Asp Ser
2120                2125                2130

Ala Tyr Lys Thr Ala Gln Ala Ile Lys Asp Phe Asn Arg Glu Lys
2135                2140                2145

Leu Pro Leu Met Ile Phe Ala Asn Trp Arg Gly Phe Ser Gly Gly
2150                2155                2160

Met Lys Asp Met Tyr Asp Gln Val Leu Lys Phe Gly Ala Tyr Ile
2165                2170                2175

Val Asp Gly Leu Arg Gln Tyr Lys Gln Pro Ile Leu Ile Tyr Ile
2180                2185                2190

Pro Pro Tyr Ala Glu Leu Arg Gly Gly Ser Trp Val Val Ile Asp
2195                2200                2205

Ala Thr Ile Asn Pro Leu Cys Ile Glu Met Tyr Ala Asp Lys Glu
2210                2215                2220

Ser Arg Gly Gly Val Leu Glu Pro Glu Gly Thr Val Glu Ile Lys
2225                2230                2235

Phe Arg Lys Lys Asp Leu Ile Lys Ser Met Arg Arg Ile Asp Pro
2240                2245                2250

Ala Tyr Lys Lys Leu Met Glu Gln Leu Gly Glu Pro Asp Leu Ser
2255                2260                2265

Asp Lys Asp Arg Lys Asp Leu Glu Gly Arg Leu Lys Ala Arg Glu
2270                2275                2280

Asp Leu Leu Leu Pro Ile Tyr His Gln Val Ala Val Gln Phe Ala
2285                2290                2295

Asp Phe His Asp Thr Pro Gly Arg Met Leu Glu Lys Gly Val Ile
2300                2305                2310

Ser Asp Ile Leu Glu Trp Lys Thr Ala Arg Thr Phe Leu Tyr Trp
2315                2320                2325

Arg Leu Arg Arg Leu Leu Leu Glu Asp Gln Val Lys Gln Glu Ile
2330                2335                2340

Leu Gln Ala Ser Gly Glu Leu Ser His Val His Ile Gln Ser Met
2345                2350                2355

Leu Arg Arg Trp Phe Val Thr Glu Gly Ala Val Lys Ala Tyr
2360                2365                2370

Leu Trp Asp Asn Asn Gln Val Val Val Gln Trp Leu Glu Gln His
2375                2380                2385

Trp Gln Ala Gly Asp Gly Pro Arg Ser Thr Ile Arg Glu Asn Ile
2390                2395                2400
```

| | | | | | | | | | | | | |
|---|---|---|---|---|---|---|---|---|---|---|---|---|
| Thr | Tyr 2405 | Leu | Lys | His | Asp | Ser 2410 | Val | Leu | Lys | Thr | Ile 2415 | Arg | Gly | Leu |
| Val | Glu 2420 | Glu | Asn | Pro | Glu | Val 2425 | Ala | Val | Asp | Cys | Val 2430 | Ile | Tyr | Leu |
| Ser | Gln 2435 | His | Ile | Ser | Pro | Ala 2440 | Glu | Arg | Ala | Gln | Val 2445 | Val | His | Leu |
| Leu | Ser 2450 | Thr | Met | Asp | Ser | Pro 2455 | Ala | Ser | Thr | | | | | |

N1-PYRAZOLOSPIROKETONE ACETYL-COA CARBOXYLASE INHIBITORS

FIELD OF THE INVENTION

This invention relates to substituted pyrazolospiroketone compounds that act as inhibitors of an acetyl-CoA carboxylase(s) and their use in treating diseases, conditions or disorders modulated by the inhibition of acetyl-CoA carboxylase enzyme(s).

BACKGROUND OF THE INVENTION

Acetyl-CoA carboxylases (ACC) are a family of enzymes found in most species and are associated with fatty acid synthesis and metabolism through catalyzing the production of malonyl-CoA from acetyl-CoA. In mammals, two isoforms of the ACC enzyme have been identified. ACC1, which is expressed at high levels in lipogenic tissues, such as fat and the liver, controls the first committed step in the biosynthesis of long-chain fatty acids. If acetyl-CoA is not carboxylated to form malonyl-CoA, it is metabolized through the Krebs cycle. ACC2, a minor component of hepatic ACC but the predominant isoform in heart and skeletal muscle, catalyzes the production of malonyl-CoA at the cytosolic surface of mitochondria, and regulates how much fatty acid is utilized in β-oxidation by inhibiting carnitine palmitoyl transferase. Thus, by increasing fatty acid utilization and by preventing increases in de novo fatty acid synthesis, chronic administration of an ACC inhibitor (ACC-I) may also deplete liver and adipose tissue triglyceride (TG) stores in obese subjects consuming a high or low-fat diet, leading to selective loss of body fat.

Studies conducted by Abu-Etheiga, et al., suggest that ACC2 plays an essential role in controlling fatty acid oxidation and, as such it would provide a target in therapy against obesity and obesity-related diseases, such as type-2 diabetes. See, Abu-Etheiga, L., et al., "Acetyl-CoA carboxylase 2 mutant mice are protected against obesity and diabetes induced by high-fat/high-carbohydrate diets" *PNAS*, 100 (18) 10207-10212 (2003). See also, Choi, C. S., et al., "Continuous fat oxidation in acetyl-CoA carboxylase 2 knockout mice increases total energy expenditure, reduces fat mass, and improves insulin sensitivity" *PNAS*, 104(42) 16480-16485 (2007).

It is becoming increasingly clear that hepatic lipid accumulation causes hepatic insulin resistance and contributes to the pathogenesis of type 2 diabetes. Salvage, et al., demonstrated that ACC1 and ACC2 are both involved in regulating fat oxidation in hepatocytes while ACC1, the dominant isoform in rat liver, is the sole regulator of fatty acid synthesis. Furthermore, in their model, combined reduction of both isoforms is required to significantly lower hepatic malonyl-CoA levels, increase fat oxidation in the fed state, reduce lipid accumulation, and improve insulin action in vivo. Thus, showing that hepatic ACC1 and ACC2 inhibitors may be useful in the treatment of nonalcoholic fatty liver disease (NAFLD) and hepatic insulin resistance. See, Savage, D. B., et al., "Reversal of diet-induced hepatic steatosis and hepatic insulin resistance by antisense oligonucleotide inhibitors of acetyl-CoA carboxylases 1 and 2" *J Clin Invest* doi: 10.1172/JCI27300. See also, Oh, W., et al., "Glucose and fat metabolism in adipose tissue of acetyl-CoA carboxylase 2 knockout mice" *PNAS*, 102(5) 1384-1389 (2005).

Consequently, there is a need for medicaments containing ACC1 and/or ACC2 inhibitors to treat obesity and obesity-related diseases (such as, NAFLD and type-2 diabetes) by inhibiting fatty acid synthesis and by increasing fatty acid oxidation.

SUMMARY OF THE INVENTION

A first embodiment of the present invention is a compound having the structure of Formula (I)

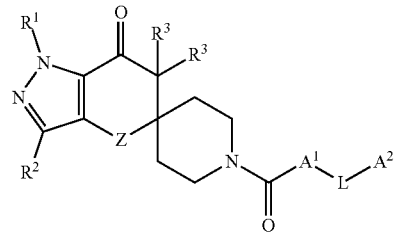

or a pharmaceutically acceptable salt thereof; wherein
$R^1$ is $(C_1-C_6)$alkyl, $(C_3-C_7)$cycloalkyl, tetrahydrofuranyl or oxetanyl; wherein said $(C_1-C_6)$alkyl is optionally substituted with 1 to 3 substituents independently selected from $(C_1-C_3)$alkoxy, hydroxy, fluoro, phenyl, tetrahydrofuranyl or oxetanyl;
$R^2$ is hydrogen, halo, $(C_1-C_3)$alkyl, or cyano;
$R^3$ are each independently hydrogen or $(C_1-C_3)$alkyl;
L is a direct bond or a $(C_1-C_6)$alkylene wherein one carbon of the $(C_1-C_6)$alkylene is optionally replaced by —C(O)—, —C(O)NH—, —NHC(O), O, S, NH or N($C_1$-$C_3$)alkyl;
Z is $CH_2$ or O;
$A^1$ and $A^2$ are each independently $(C_6-C_{10})$aryl, 5 to 12 membered heteroaryl or 8 to 12 membered fused heterocyclicaryl; wherein said $(C_6-C_{10})$aryl, 5 to 12 membered heteroaryl or 8 to 12 membered fused heterocyclicaryl are each optionally substituted with one to three substituents independently selected from $(C_1-C_3)$alkyl, $(C_1-C_3)$alkoxy, halo, amino, $(C_1-C_3)$alkylamino, di$(C_1-C_3)$alkylamino, hydroxy, cyano and amido wherein the alkyl portion of the $(C_1-C_3)$alkyl, $(C_1-C_3)$alkoxy, $(C_1-C_3)$alkylamino and di($C_1$-$C_3$)alkylamino are optionally substituted with one to five fluoro; and wherein one of $A^1$ or $A^2$ is substituted by $CO_2R^4$, $(C_1-C_6)CO_2R^4$, tetrazolyl or $(C_1-C_6)$tetrazolyl; and
$R^4$ is $(C_1-C_8)$alkyl, $(C_3-C_8)$cycloalkyl or $(C_1-C_6)$alkyl-$(C_3-C_8)$cycloalkyl; or a pharmaceutically acceptable salt thereof.

Another embodiment of the present invention is the compound of the immediately preceding embodiment wherein $R^1$ is $(C_1-C_6)$alkyl, $(C_3-C_7)$cycloalkyl, or tetrahydrofuranyl; $R^2$ is hydrogen or methyl; each $R^3$ is hydrogen; and L is a direct bond or O; or a pharmaceutically acceptable salt thereof.

Another embodiment of the present invention is the compound of the immediately preceding embodiment wherein $R^1$ is $(C_2-C_4)$alkyl; $A^1$ and $A^2$ are each independently phenyl, pyrazolyl, imidazolyl, triazolyl, pyridinyl, pyrimidinyl, indolyl, benzopyrazinyl, benzoimidazolyl, benzoimidazolonyl, pyrrolopyridinyl, pyrrolopyrimidinyl, pyrazolopyridinyl, pyrazolopyrimidinyl, indazolyl, indolinonyl, naphthyridinyl, quinolinyl, quinolinonyl, dihydroquinolinonyl, oxo-dihydroquinolinonyl, isoquinolinyl, isoquinolinonyl, dihydroisoquinonyl or oxo-dihydroisoquinonyl, each optionally substituted with one to three substituents independently selected from fluoro, chloro, methyl, methoxy, amino, methylamino, dimethylamino, amido or cyano; or a pharmaceutically acceptable salt thereof.

Yet another embodiment of the present invention is the compound of the immediately preceding embodiment wherein $R^1$ is isopropyl or t-butyl; $R^2$ is hydrogen and $R^4$ is hydrogen; or a pharmaceutically acceptable salt thereof. Still another embodiment of the present invention is the compound of the immediately preceding embodiment wherein $A^1$ is phenyl, pyridinyl, indazolyl, indolyl, benzoimidazolyl, pyrrolopyridinyl or pyrrolopyrimidinyl; each optionally substituted with one methyl, methoxy, methylamino or dimethylamino; or a pharmaceutically acceptable salt thereof. Another embodiment of the present invention is the compound of either of the two immediately preceding embodiments wherein $A^2$ is phenyl substituted with $CO_2H$ or tetrazolyl; and L is a direct bond; or a pharmaceutically acceptable salt thereof.

Another embodiment of the present invention is the compound of the immediately preceding embodiment wherein $A^1$ is phenyl, indolyl or benzoimidazolyl optionally substituted with methyl, or pyridinyl optionally substituted with methylamino or dimethylamino; or a pharmaceutically acceptable salt thereof.

Another embodiment of the present invention is a compound selected from: 4-((4-(1-Tert-butyl-7-oxo-1,4,6,7-tetrahydrospiro[indazole-5,4'-piperidine]-1'-ylcarbonyl)phenoxy)methyl)benzoic acid; 3-(4-(1-isopropyl-7-oxo-1,4,6,7-tetrahydrospiro [indazole-5,4'-piperidine]-1'-ylcarbonyl)-6-methoxypyridin-2-yl)benzoic acid; 3-(4-(1-isopropyl-7-oxo-1,4,6,7-tetrahydrospiro[indazole-5,4'-piperidine]-1'-ylcarbonyl)-6-oxo-1,6-dihydropyridin-2-yl)benzoic acid; 3-{5-[(1-tert-butyl-7-oxo-1,4,6,7-tetrahydro-1'H-spiro[indazole-5,4'-piperidin]-1'-yl)carbonyl]-6-(methylamino)pyridin-2-yl}benzoic acid; 3-{5-[(1-isopropyl-7-oxo-1,4,6,7-tetrahydro-1'H-spiro[indazole-5,4'-piperidin]-1'-yl)carbonyl]-6-(methylamino) pyridin-2-yl}benzoic acid; 4'-[(1-tert-butyl-7-oxo-1,4,6,7-tetrahydro-1'H-spiro[indazole-5,4'-piperidin]-1'-yl)carbonyl]biphenyl-3-carboxylic acid; 4'-[(1-isopropyl-7-oxo-1,4,6,7-tetrahydro-1'H-spiro[indazole-5,4'-piperidin]-1'-yl)carbonyl]biphenyl-3-carboxylic acid; 4-{5-[(1-isopropyl-7-oxo-1,4,6,7-tetrahydro-1'H-spiro[indazole-5,4'-piperidin]-1'-yl)carbonyl]-6-(methylamino)pyridin-2-yl}benzoic acid; 4-{4-[(1-isopropyl-7-oxo-1,4,6,7-tetrahydro-1'H-spiro[indazole-5,4'-piperidin]-1'-yl)carbonyl]-6-methoxypyridin-2-yl}benzoic acid; 3-{4-[(1-isopropyl-7-oxo-1,4,6,7-tetrahydro-1'H-spiro[indazole-5,4'-piperidin]-1'-yl)carbonyl]-6-methoxypyridin-2-yl}benzoic acid; 4-{4-[(1-tert-butyl-7-oxo-1,4,6,7-tetrahydro-1'H-spiro [indazole-5,4'-piperidin]-1'-yl)carbonyl]-6-methoxypyridin-2-yl}benzoic acid; 3-{4-[(1-tert-butyl-7-oxo-1,4,6,7-tetrahydro-1'H-spiro[indazole-5,4'-piperidin]-1'-yl)carbonyl]-6-methoxypyridin-2-yl}benzoic acid; 4-{5-[(1-tert-butyl-7-oxo-1,4,6,7-tetrahydro-1'H-spiro[indazole-5,4'-piperidin]-1'-yl)carbonyl]-6-(methylamino)pyridin-2-yl}benzoic acid; 4-{5-[(1-tert-butyl-7-oxo-1,4,6,7-tetrahydro-1'H-spiro[indazole-5,4'-piperidin]-1'-yl)carbonyl]-6-(ethylamino)pyridin-2-yl}benzoic acid; 4-{6-(ethylamino)-5-[(1-isopropyl-7-oxo-1,4,6,7-tetrahydro-1'H-spiro[indazole-5,4'-piperidin]-1'-yl)carbonyl]pyridin-2-yl}benzoic acid; 3-{2-[(1-isopropyl-7-oxo-1,4,6,7-tetrahydro-1'H-spiro[indazole-5,4'-piperidin]-1'-yl)carbonyl]-1H-indol-4-yl}benzoic acid; 4-{2-[(1-isopropyl-7-oxo-1,4,6,7-tetrahydro-1'H-spiro[indazole-5,4'-piperidin]-1'-yl)carbonyl]-1H-indol-4-yl}benzoic acid; 3-{2-[(1-tert-butyl-7-oxo-1,4,6,7-tetrahydro-1'H-spiro[indazole-5,4'-piperidin]-1'-yl)carbonyl]-1H-indol-4-yl}benzoic acid; 4-{2-[(1-tert-butyl-7-oxo-1,4,6,7-tetrahydro-1'H-spiro[indazole-5,4'-piperidin]-1'-yl)carbonyl]-1H-indol-4-yl}benzoic acid; 3-{5-[(1-tert-butyl-7-oxo-1,4,6,7-tetrahydro-1'H-spiro[indazole-5,4'-piperidin]-1'-yl)carbonyl]-6-(ethylamino)pyridin-2-yl}benzoic acid; 3-{6-(ethylamino)-5-[(1-isopropyl-7-oxo-1,4,6,7-tetrahydro-1'H-spiro[indazole-5,4'-piperidin]-1'-yl)carbonyl]pyridin-2-yl}benzoic acid; 3-[(1-tert-butyl-7-oxo-1,4,6,7-tetrahydro-1'H-spiro[indazole-5,4'-piperidin]-1'-yl)carbonyl]-5-(1,3-oxazol-2-yl)benzoic acid; 4-({4-[(1-tert-butyl-7-oxo-1,4,6,7-tetrahydro-1'H-spiro[indazole-5,4'-piperidin]-1'-yl)carbonyl]phenoxy}methyl)benzoic acid; 3-[(1-isopropyl-7-oxo-1,4,6,7-tetrahydro-1'H-spiro[indazole-5,4'-piperidin]-1'-yl)carbonyl]-5-(1,3-oxazol-2-yl)benzoic acid; 3-{6-(isopropylamino)-5-[(1-isopropyl-7-oxo-1,4,6,7-tetrahydro-1'H-spiro[indazole-5,4'-piperidin]-1'-yl)carbonyl]pyridin-2-yl}benzoic acid; 4-{5-[(1-tert-butyl-7-oxo-1,4,6,7-tetrahydro-1'H-spiro[indazole-5,4'-piperidin]-1'-yl)carbonyl]-6-(isopropylamino)pyridin-2-yl}benzoic acid; 4-{6-(isopropylamino)-5-[(1-isopropyl-7-oxo-1,4,6,7-tetrahydro-1'H-spiro[indazole-5,4'-piperidin]-1'-yl)carbonyl]pyridin-2-yl}benzoic acid; 4-{6-[(1-isopropyl-7-oxo-1,4,6,7-tetrahydro-1'H-spiro[indazole-5,4'-piperidin]-1'-yl)carbonyl]-1H-indazol-4-yl}benzoic acid; 3-{4-[(1-isopropyl-7-oxo-1,4,6,7-tetrahydro-1'H-spiro[indazole-5,4'-piperidin]-1'-yl)carbonyl]-6-oxo-1,6-dihydropyridin-2-yl}benzoic acid; 4-{4-[(1-isopropyl-7-oxo-1,4,6,7-tetrahydro-1'H-spiro[indazole-5,4'-piperidin]-1'-yl)carbonyl]-6-oxo-1,6-dihydropyridin-2-yl}benzoic acid; 3-{2-[(1-isopropyl-7-oxo-1,4,6,7-tetrahydro-1'H-spiro[indazole-5,4'-piperidin]-1'-yl)carbonyl]-1H-pyrrolo[2,3-b]pyridin-4-yl}benzoic acid; 4-{2-[(1-isopropyl-7-oxo-1,4,6,7-tetrahydro-1'H-spiro[indazole-5,4'-piperidin]-1'-yl)carbonyl]-1H-pyrrolo[2,3-b]pyridin-4-yl}benzoic acid; 4-{2-[(1-isopropyl-7-oxo-1,4,6,7-tetrahydro-1'H-spiro[indazole-5,4'-piperidin]-1'-yl)carbonyl]-1H-pyrrolo[3,2-c]pyridin-4-yl}benzoic acid; (5-{2-[(1-isopropyl-7-oxo-1,4,6,7-tetrahydro-1'H-spiro[indazole-5,4'-piperidin]-1'-yl)carbonyl]-1H-indol-4-yl}-2-methoxyphenyl)acetic acid; 3-{6-(dimethylamino)-4-[(1-isopropyl-7-oxo-1,4,6,7-tetrahydro-1'H-spiro[indazole-5,4'-piperidin]-1'-yl)carbonyl]pyridin-2-yl}benzoic acid; 4-{6-(dimethylamino)-4-[(1-isopropyl-7-oxo-1,4,6,7-tetrahydro-1'H-spiro[indazole-5,4'-piperidin]-1'-yl)carbonyl]pyridin-2-yl}benzoic acid; 4-{6-[(1-isopropyl-7-oxo-1,4,6,7-tetrahydro-1'H-spiro[indazole-5,4'-piperidin]-1'-yl)carbonyl]-7H-pyrrolo[2,3-d]pyrimidin-4-yl}benzoic acid; 3-{2-[(1-isopropyl-7-oxo-1,4,6,7-tetrahydro-1'H-spiro[indazole-5,4'-piperidin]-1'-yl)carbonyl]-1H-pyrrolo[3,2-c]pyridin-4-yl}benzoic acid; 3-{6-[(1-isopropyl-7-oxo-1,4,6,7-tetrahydro-1'H-spiro[indazole-5,4'-piperidin]-1'-yl)carbonyl]-7H-pyrrolo[2,3-d]pyrimidin-4-yl}benzoic acid; 4-{6-[(1-isopropyl-7-oxo-1,4,6,7-tetrahydro-1'H-spiro[indazole-5,4'-piperidin]-1'-yl)carbonyl]-1H-indol-4-yl}benzoic acid; 4-{2-[(1-isopropyl-7-oxo-1,4,6,7-tetrahydro-1'H-spiro[indazole-5,4'-piperidin]-1'-yl)carbonyl]-1H-pyrrolo[2,3-c]pyridin-4-yl}benzoic acid; 3-{6-[(1-isopropyl-7-oxo-1,4,6,7-tetrahydro-1'H-spiro[indazole-5,4'-piperidin]-1'-yl)carbonyl]-1H-indol-4-yl}benzoic acid; 3-{2-[(1-isopropyl-7-oxo-1,4,6,7-tetrahydro-1'H-spiro[indazole-5,4'-piperidin]-1'-yl)carbonyl]-1H-pyrrolo[2,3-c]pyridin-4-yl}benzoic acid; 3-{2-[(1-isopropyl-7-oxo-1,4,6,7-tetrahydro-1'H-spiro[indazole-5,4'-piperidin]-1'-yl)carbonyl]-1H-indol-6-yl}benzoic acid; 4-{5-[(1-isopropyl-7-oxo-1,4,6,7-tetrahydro-1'H-spiro[indazole-5,4'-piperidin]-1'-yl)carbonyl]-6-[(2,2,2-trifluoroethyl)amino]pyridin-2-yl}benzoic acid; 3-{5-[(1-isopropyl-7-oxo-1,4,6,7-tetrahydro-1'H-spiro[indazole-5,4'-piperidin]-1'-yl)carbonyl]-6-(methylamino)pyridin-3-yl}benzoic acid; 4-{5-

[(1-isopropyl-7-oxo-1,4,6,7-tetrahydro-1'H-spiro[indazole-5,4'-piperidin]-1'-yl)carbonyl]-6-(methylamino)pyridin-3-yl}benzoic acid; 3-{2-[(1-isopropyl-7-oxo-1,4,6,7-tetrahydro-1'H-spiro[indazole-5,4'-piperidin]-1'-yl)carbonyl]-1H-benzimidazol-4-yl}benzoic acid; 4-{2-[(1-isopropyl-7-oxo-1,4,6,7-tetrahydro-1'H-spiro[indazole-5,4'-piperidin]-1'-yl)carbonyl]-1H-benzimidazol-5-yl}benzoic acid; 3-{2-[(1-isopropyl-7-oxo-1,4,6,7-tetrahydro-1'H-spiro[indazole-5,4'-piperidin]-1'-yl)carbonyl]-1H-benzimidazol-5-yl}benzoic acid; 3-(6-(1-isopropyl-7-oxo-1,4,6,7-tetrahydrospiro[indazole-5,4'-piperidine]-1'-ylcarbonyl)-2-methyl-1H-benzo[d]imidazol-4-yl)benzoic acid; 4-(6-(1-isopropyl-7-oxo-1,4,6,7-tetrahydrospiro[indazole-5,4'-piperidine]-1'-ylcarbonyl)-2-methyl-1H-benzo[d]imidazol-4-yl)benzoic acid; 1-isopropyl-1'-{[3'-(1H-tetrazol-5-yl)biphenyl-4-yl]carbonyl}-1,4-dihydrospiro[indazole-5,4'-piperidin]-7(6H)-one; and 1-tert-butyl-1'-{[3'-(1H-tetrazol-5-yl)biphenyl-4-yl]carbonyl}-1,4-dihydrospiro[indazole-5,4'-piperidin]-7(6H)-one; or a pharmaceutically acceptable salt thereof.

Yet another embodiment of the present invention is the compound of the immediately preceding embodiment selected from 3-{2-[(1-isopropyl-7-oxo-1,4,6,7-tetrahydro-1'H-spiro[indazole-5,4'-piperidin]-1'-yl)carbonyl]-1H-benzimidazol-4-yl}benzoic acid; 4-{6-(dimethylamino)-4-[(1-isopropyl-7-oxo-1,4,6,7-tetrahydro-1'H-spiro[indazole-5,4'-piperidin]-1'-yl)carbonyl]pyridin-2-yl}benzoic acid; 3-{2-[(1-isopropyl-7-oxo-1,4,6,7-tetrahydro-1'H-spiro[indazole-5,4'-piperidin]-1'-yl)carbonyl]-1H-indol-4-yl}benzoic acid; 3-{2-[(1-isopropyl-7-oxo-1,4,6,7-tetrahydro-1'H-spiro[indazole-5,4'-piperidin]-1'-yl)carbonyl]-1H-pyrrolo[2,3-b]pyridin-4-yl}benzoic acid; 4-{2-[(1-isopropyl-7-oxo-1,4,6,7-tetrahydro-1'H-spiro[indazole-5,4'-piperidin]-1'-yl)carbonyl]-1H-benzimidazol-5-yl}benzoic acid; 3-{2-[(1-isopropyl-7-oxo-1,4,6,7-tetrahydro-1'H-spiro[indazole-5,4'-piperidin]-1'-yl)carbonyl]-1H-benzimidazol-5-yl}benzoic acid; 3-(6-(1-isopropyl-7-oxo-1,4,6,7-tetrahydrospiro[indazole-5,4'-piperidine]-1'-ylcarbonyl)-2-methyl-1H-benzo[d]imidazol-4-yl)benzoic acid; and 4-(6-(1-isopropyl-7-oxo-1,4,6,7-tetrahydrospiro[indazole-5,4'-piperidine]-1'-ylcarbonyl)-2-methyl-1H-benzo[d]imidazol-4-yl)benzoic acid; or a pharmaceutically acceptable salt thereof.

Another aspect of the present invention is a pharmaceutical composition comprising an amount of a compound of formula (I) as described in any of the embodiments; or a pharmaceutically acceptable salt thereof and a pharmaceutically acceptable excipient, diluent, or carrier. Preferably, the composition comprises a therapeutically effective amount of a compound of the present invention or a pharmaceutically acceptable salt thereof. The composition may also contain at least one additional pharmaceutical agent. Preferred agents include anti-diabetic agents and/or anti-obesity agents (described herein below).

In yet another aspect of the present invention is a method for treating a disease, condition, or disorder mediated by the inhibition of acetyl-CoA carboxylase enzyme(s) in a mammal that includes the step of administering to a mammal, preferably a human, in need of such treatment a therapeutically effective amount of a compound of the present invention or a pharmaceutically acceptable salt thereof, or a pharmaceutical composition thereof.

Diseases, disorders, or conditions mediated by inhibitors of acetyl-CoA carboxylases include Type II diabetes and diabetes-related diseases, such as nonalcoholic fatty liver disease (NAFLD), hepatic insulin resistance, hyperglycemia, metabolic syndrome, impaired glucose tolerance, diabetic neuropathy, diabetic nephropathy, diabetic retinopathy, obesity, dyslipidemia, hypertension, hyperinsulinemia, and insulin resistance syndrome. Preferred diseases, disorders, or conditions include Type II diabetes, nonalcoholic fatty liver disease (NAFLD), hepatic insulin resistance, hyperglycemia, impaired glucose tolerance, obesity, and insulin resistance syndrome. More preferred are Type II diabetes, nonalcoholic fatty liver disease (NAFLD), hepatic insulin resistance, hyperglycemia, and obesity. Most preferred is Type II diabetes.

A preferred embodiment is a method for treating, (e.g. delaying the progression or onset) of Type 2 diabetes and diabetes-related disorders in animals comprising the step of administering to an animal in need of such treatment a therapeutically effective amount of a compound of the present invention or a pharmaceutically acceptable salt thereof or a composition thereof.

Another preferred embodiment is a method for treating obesity and obesity-related disorders in animals comprising the step of administering to an animal in need of such treatment a therapeutically effective amount of a compound of the present invention or a pharmaceutically acceptable salt thereof or a composition thereof.

Yet another preferred embodiment is a method for treating nonalcoholic fatty liver disease (NAFLD) or hepatic insulin resistance in animals comprising the step of administering to an animal in need of such treatment a therapeutically effective amount of a compound of the present invention or a pharmaceutically acceptable salt thereof or a composition thereof.

Compounds of the present invention may be administered in combination with other pharmaceutical agents (in particular, anti-obesity and anti-diabetic agents described herein below). The combination therapy may be administered as (a) a single pharmaceutical composition which comprises a compound of the present invention or a pharmaceutically acceptable salt thereof, at least one additional pharmaceutical agent described herein and a pharmaceutically acceptable excipient, diluent, or carrier; or (b) two separate pharmaceutical compositions comprising (i) a first composition comprising a compound of the present invention or a pharmaceutically acceptable salt thereof and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

BRIEF DESCRIPTION OF THE DRAWINGS

FIG. 1 provides a sequence of recombinant human ACC1 (SEQ. ID NO. 1) that can be employed in the Transcreener in vitro assay.

FIG. 2 provides a sequence of recombinant human ACC2 (SEQ. ID NO. 2) that can be employed in the Transcreener in vitro assay.

DETAILED DESCRIPTION OF THE INVENTION

Definitions

The phrase "therapeutically effective amount" means an amount of a compound of the present invention or a pharmaceutically acceptable salt thereof that: (i) treats or prevents the particular disease, condition, or disorder, (ii) attenuates, ameliorates, or eliminates one or more symptoms of the particular disease, condition, or disorder, or (iii)

prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated" or "modulating", or "modulate(s)", as used herein, unless otherwise indicated, refers to the inhibition of the Acetyl-CoA carboxylases (ACC) enzyme(s) with compounds of the present invention.

The terms "mediated" or "mediating" or "mediate(s)", as used herein, unless otherwise indicated, refers to the (i) treatment or prevention the particular disease, condition, or disorder, (ii) attenuation, amelioration, or elimination of one or more symptoms of the particular disease, condition, or disorder, or (iii) prevention or delay of the onset of one or more symptoms of the particular disease, condition, or disorder described herein, by inhibiting the Acetyl-CoA carboxylases (ACC) enzyme(s).

The term "compounds of the present invention" (unless specifically identified otherwise) refer to compounds of Formula (I) and any pharmaceutically acceptable salts of the compounds, as well as, all stereoisomers (including diastereoisomers and enantiomers), tautomers, conformational isomers, and isotopically labeled compounds. Hydrates and solvates of the compounds of the present invention are considered compositions of the present invention, wherein the compound is in association with water or solvent, respectively.

The terms "$(C_1-C_6)$alkyl" and "$(C_1-C_3)$alkyl" are alkyl groups of the specified number of carbons, from one to six or one to three carbons, respectively, which can be either straight chain or branched. For example, the term "$(C_1-C_3)$ alkyl" has from one to three carbons and consists of methyl, ethyl, n-propyl and isopropyl.

The term "$(C_3-C_7)$cycloalkyl" means a cycloalkyl group with three to seven carbon atoms and consists of cyclopropyl, cyclobutyl, cyclopentyl, cyclohexyl and cycloheptyl. The term "halo" means fluoro, chloro, bromo or iodo. The term "$(C_6-C_{10})$aryl" means an aromatic carbocyclic group consisting of six to ten carbon atoms such as phenyl or naphthyl.

The term "5 to 12 membered heteroaryl" means a five to twelve membered aromatic group which contains at least one heteroatom selected from nitrogen, oxygen and sulfur. As used herein the point of attachment of the "5 to 12 membered heteroaryl" group is on a carbon atom of that group. The "5 to 12 membered heteroaryl" group can be either monocyclic or bicyclic. Preferred embodiments of monocyclic heteroaryls include, but are not limited to, pyrazolyl, imidazolyl, triazolyl, pyridinyl, and pyrimidinyl. Preferred embodiments of bicyclic heteroaryls include, but are not limited to, radicals of the following ring systems:

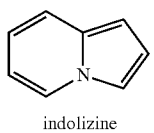
indolizine

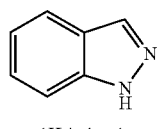
1H-indazole

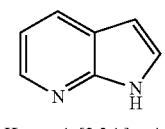
1H-pyrrolo[2,3-b]pyridine

-continued

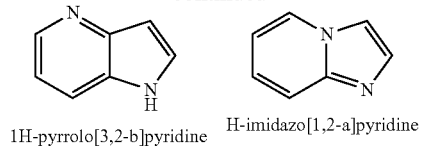
1H-pyrrolo[3,2-b]pyridine   H-imidazo[1,2-a]pyridine

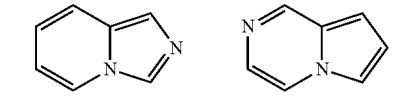
H-imidazo[1,5-a]pyridine   H-pyrrolo[1,2-a]pyrazine

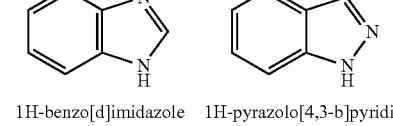
1H-benzo[d]imidazole   1H-pyrazolo[4,3-b]pyridine

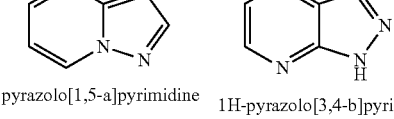
pyrazolo[1,5-a]pyrimidine   1H-pyrazolo[3,4-b]pyridine

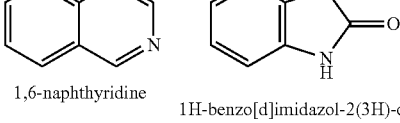
1,6-naphthyridine   1H-benzo[d]imidazol-2(3H)-one

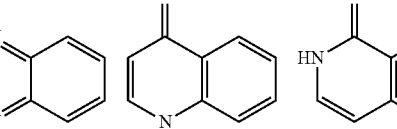
quinoxaline   quinolin-4(1H)-one   isoquinolin-1(2H)-one

The term "8 to 12 membered fused heterocyclicaryl" means an 8 to 12 membered ring system in which a non-aromatic heterocyclic ring is fused to an aryl ring. As used herein the point of attachment of the "8 to 12 membered fused heterocyclicaryl" group is on a carbon atom of that group. A preferred embodiment includes radicals of ring systems such as:

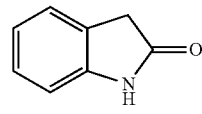
indolin-2-one

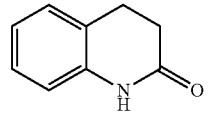
3,4-dihydroquinolin-2(1H)-one

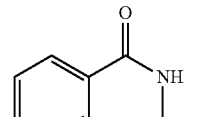
3,4-dihydroisoquinolin-1(2H)-one

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the *Beilstein* online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). Similarly, a "hydroxy-protecting group" refers to a substituent of a hydroxy group that blocks or protects the hydroxy functionality. Suitable hydroxyl-protecting groups (O-Pg) include for example, allyl, acetyl, silyl, benzyl, para-methoxybenzyl, trityl, and the like. The need for such protection is readily determined by one skilled in the art. For a general description of protecting groups and their use, see T. W. Greene, *Protective Groups in Organic Synthesis*, John Wiley & Sons, New York, 1991.

The following reaction schemes, Reaction Scheme I through Reaction Scheme provide representative procedures that are used to prepare compounds of formula (I). It is to be understood that these reaction schemes are to be construed in a non-limiting manner and that reasonable variations of the depicted methods can be used to prepare compounds of formula (I).

Reaction Scheme I

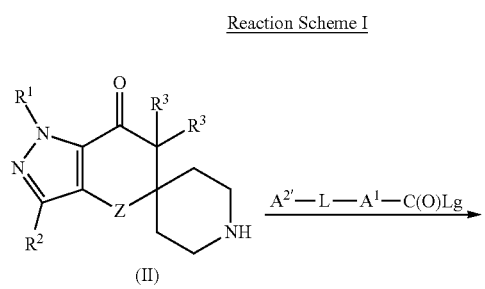

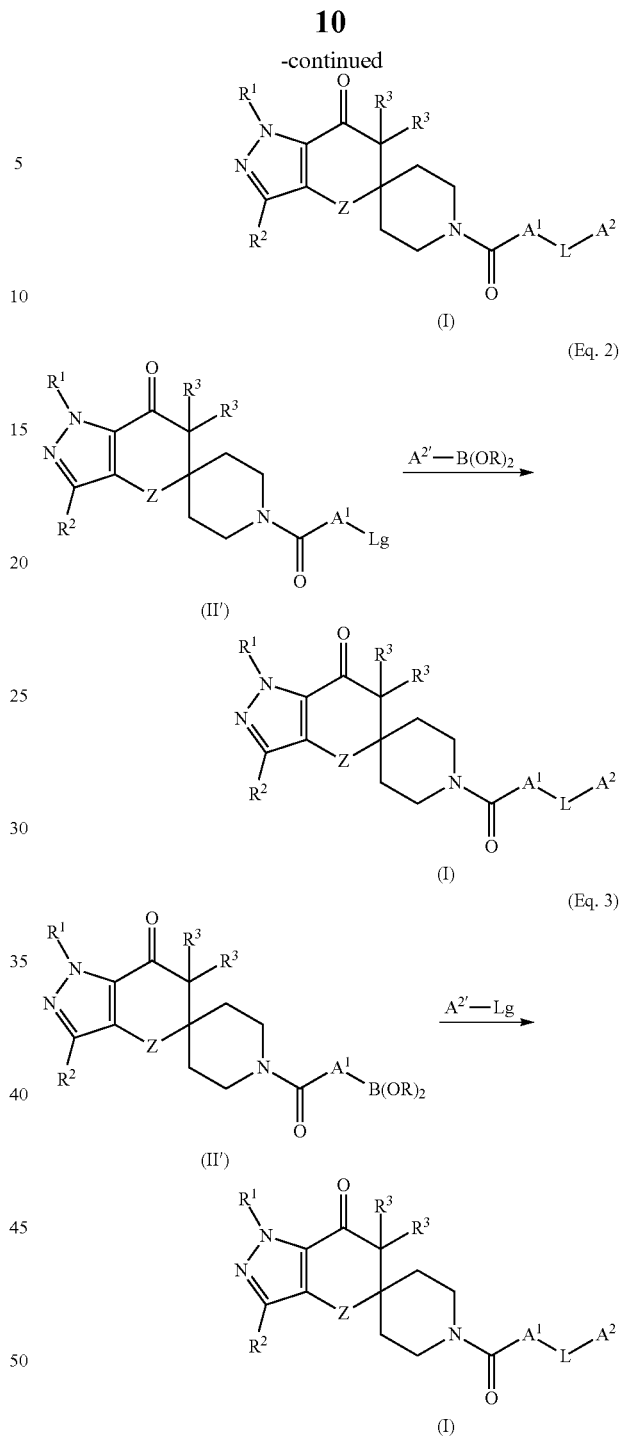

Reaction Scheme I provides three synthetic routes from penultimate intermediates to compounds of formula (I). In Equation 1 the compound of Formula (II) is reacted with $A^{2'}$-L-$A^1$-C(O)Lg, wherein Lg is an appropriate leaving group such as hydroxy or halide, to provide the compound of Formula (I). For example, the compound (I) may be formed using a standard peptide coupling reaction with the desired carboxylic acid ($A^{2'}$-L-$A^1$-$CO_2$H, wherein $A^{2'}$ represents wither $A^2$ itself or a protected version of $A^2$ which can be deprotected to provide $A^2$). For example, the spiropiperidine intermediate (II) and carboxylic acid ($A^{2'}$-L-$A^1$-$CO_2$H) may be coupled by forming an activated carboxylic acid ester, such as by contacting the carboxylic acid ($A^{2'}$-

L-A$^1$-CO$_2$H) with a peptide coupling reagent, such as O-(7-azabenzotriazol-1-yl)-N,N,N',N'-tetramethyluronium hexafluorophosphate (HATU) or 1-Ethyl-3-(3-dimethylaminopropyl)carbodiimide hydrochloride (EDC.HCl), in the presence or absence of an activating agent, such as hydroxybenzotriazole (HOBt) and in the presence of a suitable base, such as N,N-diisopropylethylamine (DIEA), triethylamine or N-methylmorpholine (NMM), in a suitable solvent such as THF and/or DMF or dichloromethane and then contacting the activated carboxylic acid ester with the spiropiperidine derivative (IIa) to form a compound of Formula (I). The reaction can typically carried out at 0° C. to 90° C. for a period of 1 to 24 hours.

Alternatively, compounds of Formula (I) can be formed by first converting the carboxylic acid (A$^{2'}$-L-A$^1$-CO$_2$H) to an acid chloride (A$^{2'}$-L-A$^1$-COCl), such as by reacting with thionyl chloride, and then reacting the acid chloride with the spiropiperidiene derivative (IIa) in the presence of an appropriate base such as triethylamine in an appropriate solvent such as dichloromethane to form a compound of Formula (I). Still another alternative method entails treating the carboxylic acid (A$^{2'}$-L-A$^1$-CO$_2$H) with 2-chloro-4,6-dimethoxytriazine in the presence of a suitable base, such as N-methylmorpholine in a suitable solvent such as THF and/or DMF. To the activated ester is added a solution of the spiropiperidine derivative (IIa) and base, such as N-methylmorpholine, in a suitable solvent, such as THF and/or DMF which the provides the compound of formula (I).

The second and third reactions depicted in Reaction Scheme I depict the preparation of the compound of Formula (I) using a Suzuki-type coupling reaction. The Suzuki-type coupling reactions can be carried out according to methods known to those skilled in the art such as those described in Miyaura, N.; Suzuki, A. Chem. Rev. 1995, 95, 2457-2483. In Equation 2 of Scheme I the compound of Formula (II') in which Lg represents an appropriate leaving group such as triflate, chloro, bromo or iodo is reacted with an appropriately substituted boronate, A$^{2'}$-B(OR)$_2$. The reaction is typically carried out in the presence of a palladium catalyst and a base in an appropriate solvent. The boronate can be either in the form of a boronic acid or a boronic ester. In Equation 3 of Scheme I the boronate compound of Formula (II") is reacted with an appropriately substituted compound A$^{2'}$-Lg in which Lg represents an appropriate leaving group such as triflate, chloro, bromo or iodo. It is to be appreciated that these reactions can be carried out where the A$^1$ and A$^2$ moieties in the compounds of formulae (II') and (II") may contain a protected carboxylic acid group which can subsequently be deprotected to provide an acid group in the compound of formula (I).

Reaction Scheme IA

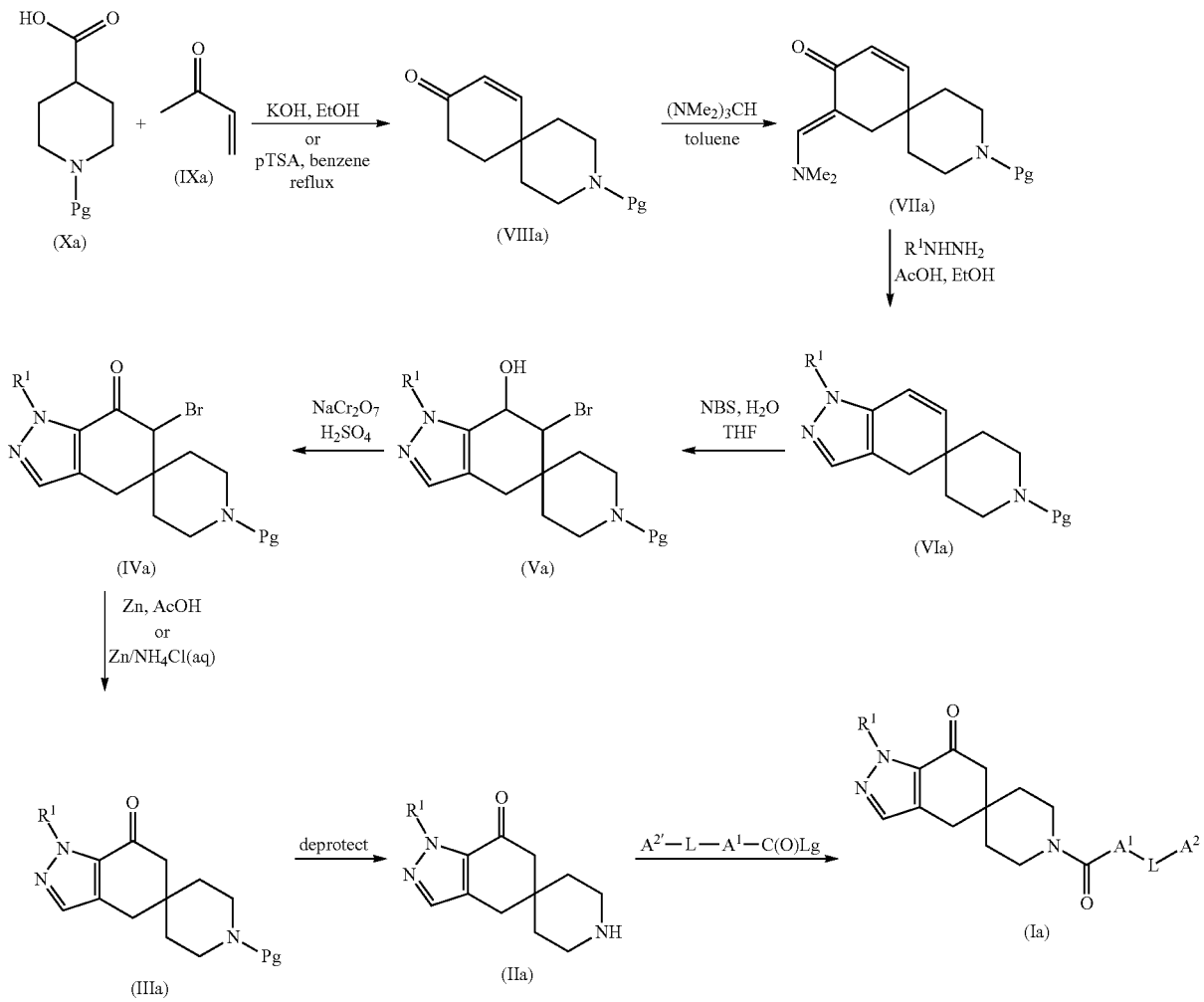

Reaction Scheme IA outlines the general procedures one could use to provide compounds of the present invention having Formula (Ia) which are compounds of Formula (I) in which $R^2$ and each $R^3$ are each hydrogen and Z is $CH_2$. The protected spiropiperidine derivative (VIIIa) may be formed by treating the appropriately protected piperidine aldehyde (Xa) with methyl vinyl ketone (IXa). The group Pg represents an appropriate amine protecting group and is preferably N-tert-butoxycarbonyl (BOC) or carbobenzyloxy (Cbz). This reaction can be carried out in the presence of ethanolic potassium hydroxide according to a procedure analogous to that described by Roy, S. et al., *Chem. Eur. J.* 2006, 12, 3777-3788 at 3786. Alternatively, the reaction can be carried out in the presence of para-toluenesulfonic acid (pTSA) in refluxing benzene to provide the desired product (VIIIa). The spiropiperidine derivative (VIIIa) can then be reacted with tris-(N,N-dimethylamino) methane in refluxing toluene to provide the eneamine functionalized spiropiperidine derivative (VIIa). Compound (VIIa) is then reacted with an appropriate hydrazine derivative $R^1NHNH^2$ in the presence of acetic acid in refluxing ethanol to provide the desired cyclized compound of formula (VIa) (see Murali Dhar, T. G. et al. *Bioorg. Med. Chem. Lett.* 2007, 17, 5019-5024 at 5020. The compound of formula (VIa) can then be treated with N-bromosuccinimide (NBS) in the presence of water in THF to provide the corresponding bromo hydroxy derivative of formula (Va). The bromo hydroxy derivative (Va) is then oxidized with Jones reagent in a method analogous to that provided in Wolinsky, J. et al., *J. Org. Chem.* 1978, 43(5), 875-881 at 876, 879 to provide the □-bromo keto derivative of formula (IVa). The compound of formula (IVa) can then be debrominated using conventional methods such as treatment with zinc and acetic acid or alternatively, zinc in the presence of aqueous ammonium chloride to provide the compound of formula (IIIa).

The compound of formula (IIIa) can then be deprotected to provide the free spiropiperidine derivative of formula (IIa) using standard methods which depend on which protecting group Pg has been employed. For example, when Pg represents tert-butyloxycarbonyl (BOC) standard strong acid deprotection conditions such as 4N hydrochloric acid in dioxane or trifluoroacetic acid in an appropriate solvent such as dichloromethane can be used to remove the BOC group. When Pg represents carbobenzyloxy (Cbz), hydrogenation over palladium on carbon in ethanol or treatment with ammonium formate in the presence of palladium on carbon in ethanol can be employed to carry out the deprotection.

The spiropiperidine derivative of Formula (IIa) can then be acylated by employing standard methods to provide the compound of Formula (Ia). For example, the compound (la) may then be formed using a standard peptide coupling reaction with the desired carboxylic acid $(A^{2'}\text{-}L\text{-}A^1\text{-}CO_2H$, wherein $A^{2'}$ represents either $A^2$ itself or a protected version of $A^2$ which can be deprotected to provide $A^2$). For example, The spiropiperidine intermediate (IIa) and carboxylic acid $(A^{2'}\text{-}L\text{-}A^1\text{-}CO_2H)$ may be coupled by forming an activated carboxylic acid ester, such as by contacting the carboxylic acid $(A^{2'}\text{-}L\text{-}A^1\text{-}CO_2H)$ with a peptide coupling reagent, such as O-(7-azabenzotriazol-1-yl)-N,N,N',N'-tetramethyluronium hexafluorophosphate (HATU) or 1-Ethyl-3-(3-dimethylaminopropyl) carbodiimide hydrochloride (EDC.HCl), in the presence or absence of an activating agent, such as hydroxybenzotriazole (HOBt) and in the presence of a suitable base, such as N,N-diisopropylethylamine (DIEA), triethylamine or N-methylmorpholine (NMM), in a suitable solvent such as THF and/or DMF or dichloromethane and then contacting the activated carboxylic acid ester with the spiropiperidine derivative (IIa) to form a compound of Formula (Ia).

Alternatively, compounds of Formula (Ia) can be formed by first converting the carboxylic acid $(A^{2'}\text{-}L\text{-}A^1\text{-}CO_2H)$ to an acid chloride $(A^{2'}\text{-}L\text{-}A^1\text{-}COCl)$, such as by reacting with thionyl chloride, and then reacting the acid chloride with the spiropiperidiene derivative (IIa) in the presence of an appropriate base such as triethylamine in an appropriate solvent such as dichloromethane to form a compound of Formula (Ia). Still another alternative method entails treating the carboxylic acid $(A^{2'}\text{-}L\text{-}A^1\text{-}CO_2H)$ with 2-chloro-4,6-dimethoxytriazine in the presence of a suitable base, such as N-methylmorpholine in a suitable solvent such as THF and/or DMF. To the activated ester is added a solution of the spiropiperidine derivative (IIa) and base, such as N-methylmorpholine, in a suitable solvent, such as THF and/or DMF which the provides the compound of formula (Ia).

Reaction Scheme II

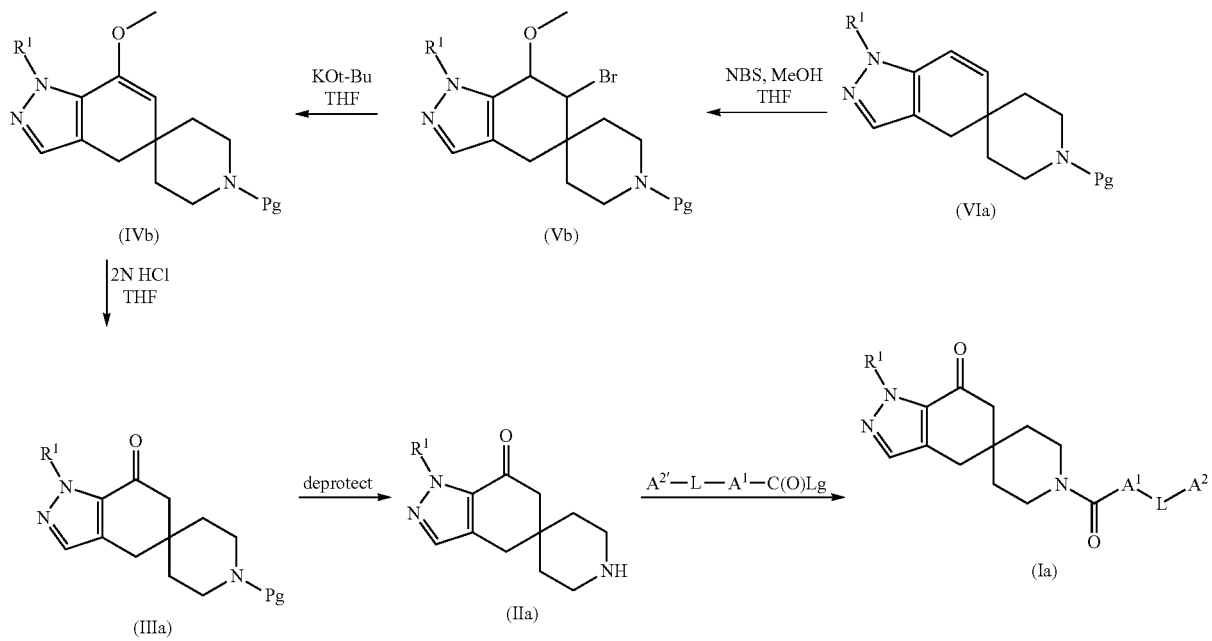

Reaction Scheme II provides an alternative synthesis of compounds of formula (Ia) starting from the intermediate of formula (VIa). The compound of formula (VIa) is treated with N-bromosuccinimide (NBS) in the presence of methanol in THF (Nishimura, T. et al. *Org. Lett.* 2008, 10(18), 4057-4060 at 4059) to provide the methoxy bromo spiropiperidine derivative of formula (Vb). Base induced elimination of compound (Vb) by treatment with a strong base such as potassium tert-butoxide in THF provides the compound of formula (IVb) which is then treated with a strong acid such as 2N hydrochloric acid in THF to provide the compound of formula (IIIa). Compound (IIIa) can then be deprotected and acylated as described previously in Reaction Scheme I to provide compounds of formula (Ia).

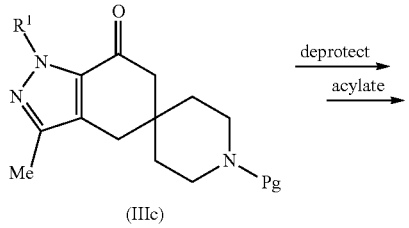

Reaction Scheme III

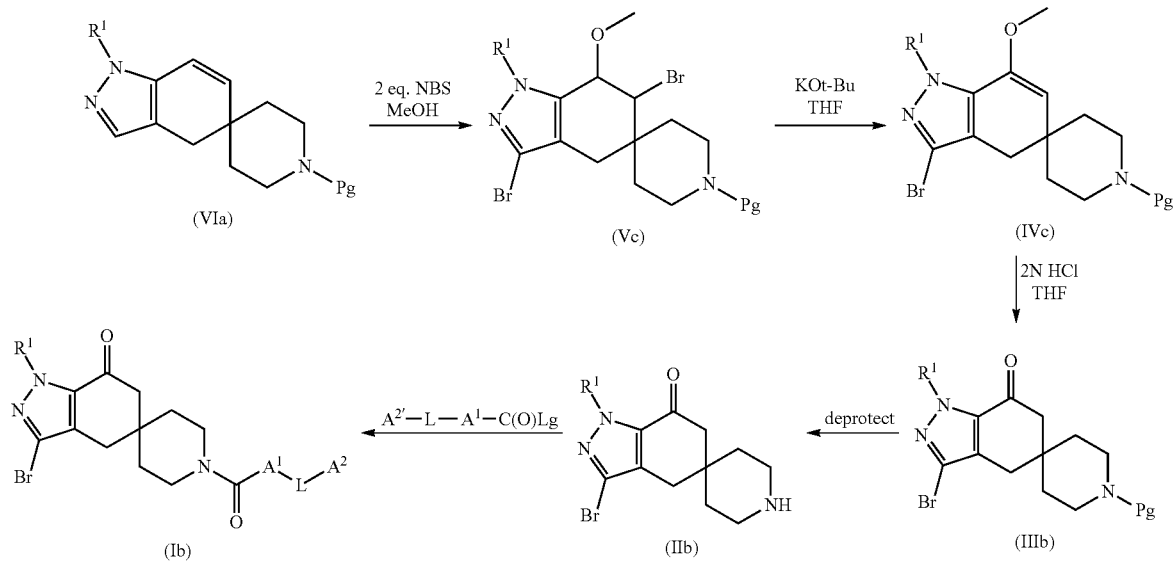

Reaction Scheme III provides a synthesis of compounds of formula (Ib) which are compounds of formula (I) in which $R^2$ is bromo and each $R^3$ is hydrogen. The compound of formula (VIa) is reacted with approximately two equivalents of N-bromosuccinimide in the presence of methanol to provide the dibromo methoxy spiropiperidine derivative of formula (Vc). Compound (Vc) is then subjected to elimination conditions by treatment with a strong base such as potassium tert-butoxide in an appropriate solvent to provide the compound of formula (IVc). Treatment of the compound of formula (IVc) with strong acid such as 2N hydrochloric acid provides the compound of formula (IIIb). Deprotection of compound (IIIb) to provide compound (IIb) followed by acylation to provide the compound of formula (Ib) can be carried out as described previously for Reaction Scheme I.

Reaction Scheme IV

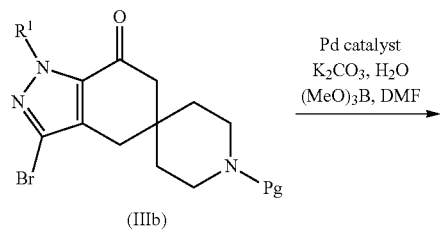

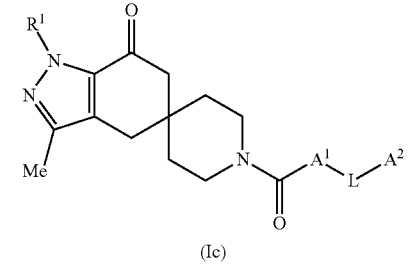

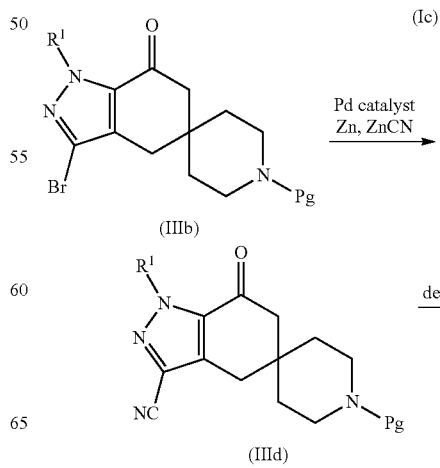

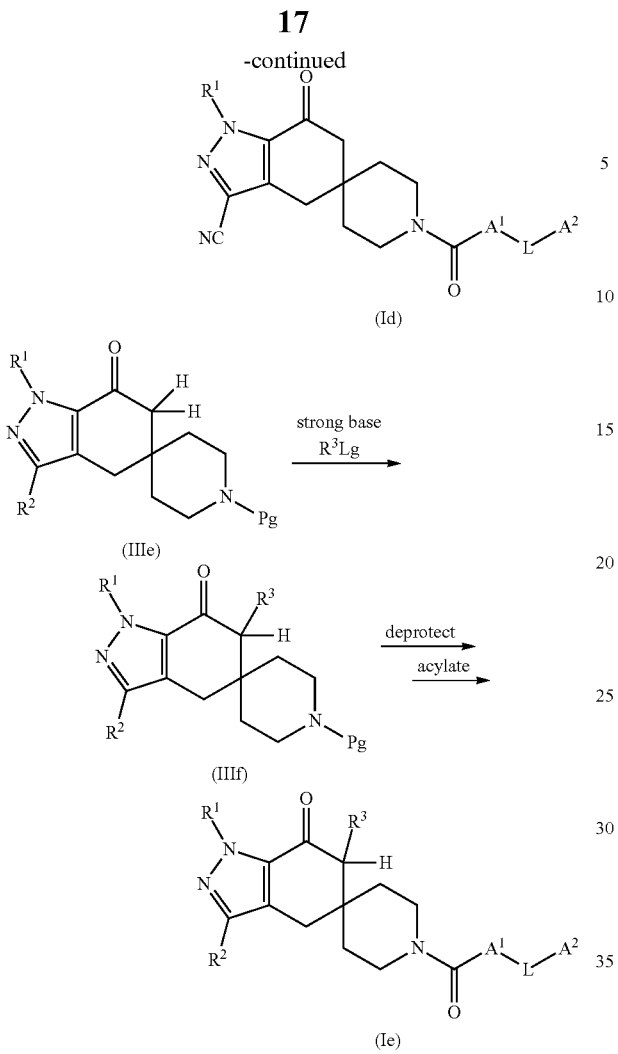

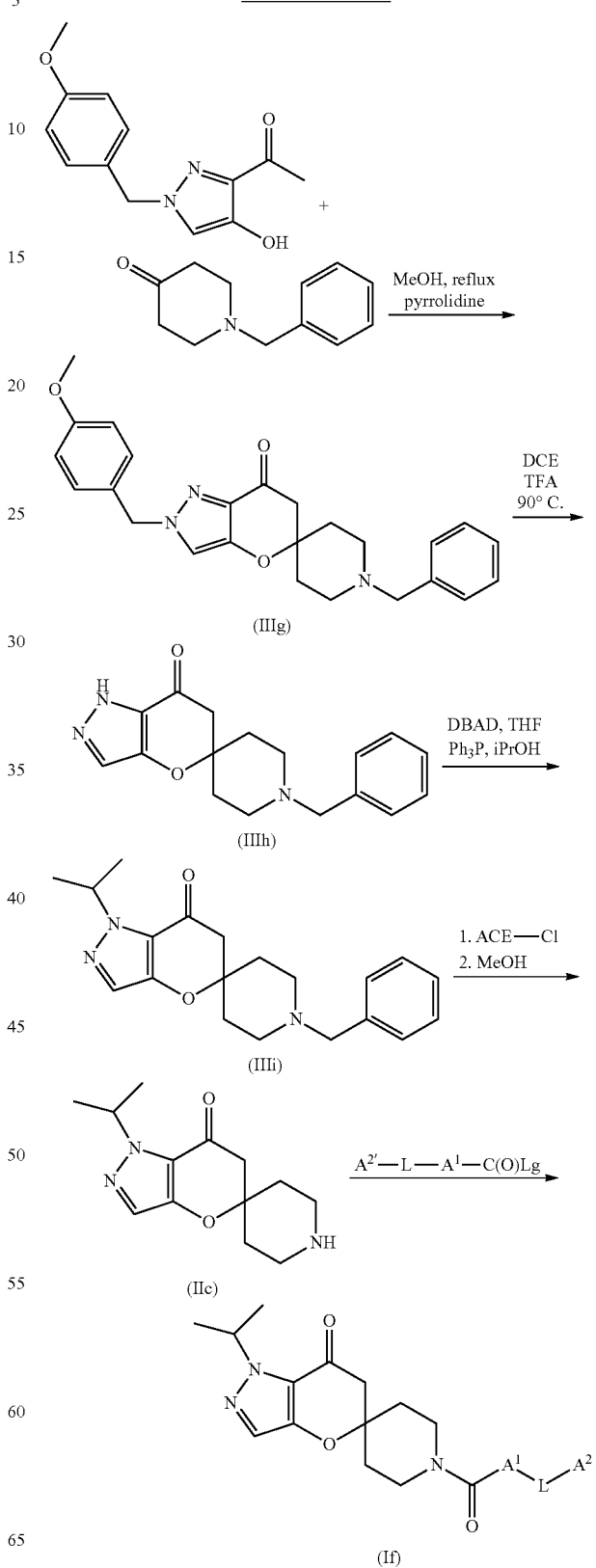

same or different. The compound of formula (IIIf) can then be deprotected and acylated as previously described to provide the compound of formula (Ie).

Reaction Scheme VI

Reaction Scheme IV depicts the preparation of certain other compounds within formula (I) from certain of the intermediates previously depicted. The first reaction in Scheme IV shows introduction of a methyl group at the $R^2$ position by reacting the bromo spiropiperidine derivative of formula (IIIb) with trimethoxyborate in the presence of an appropriate palladium catalyst, such as palladium tetrakis triphenylphosphine in the presence of potassium carbonate and water to provide (IIIc). Other alkyl groups can be introduced at the $R^2$ position in an analogous manner. The compound of formula (IIIc) can then be deprotected and acylated as previously described. The second reaction in Reaction Scheme IV depicts introduction of a cyano group at the $R^2$ position. The bromo spiropiperidine compound (IIIb) is reacted with zinc cyanide in the presence of zinc and an appropriate palladium catalyst to provide (IIId) which can then be deprotected and acylated to provide a compound of formula (Id). The third reaction in Scheme IV depicts introduction of an appropriate group at the $R^3$ position of the compound (IIIe). The compound (IIIe) is deprotonated with a strong base, such as lithium hexamethyldisilazide (LHMDS) under appropriate anhydrous conditions in an appropriate solvent, preferably at low temperature. The enolate thus formed is then reacted with an appropriate electrophile $R^3Lg$ wherein Lg represents an appropriate leaving group (such as a halide when $R^3Lg$ is an alkyl halide) to provide (IIIf) wherein $R^3$ is an appropriate group such as an alkyl group. The deprotonation of (IIIf) and reaction with another $R^3Lg$ can then be carried out again if desired to prepare a di-$R^3$ (IIIf) compound wherein the $R^3$ groups may be the Reaction Scheme VI provides the synthesis of compounds within Formula (I) wherein $R^1$ is isopropyl, $R^2$ is hydrogen, each $R^3$ is hydrogen and Z is oxygen. 1-(1-(4-methoxybenzyl)-4-hydroxy-1H-pyrazol-3-yl)ethanone is reacted with 1-benzyl piperidin-4-one in refluxing methanol in the presence of pyrrolidine to provide the diprotected spiro-compound (IIIg). The para-methoxybenzyl group of (IIIg) is then removed upon treatment with trifluoroacetic acid in dichloroethane at an elevated temperature, such as 90° C., to provide the benzyl protected N-1 (H) pyrazole derivative (IIh). This benzyl protected N-1(H) pyrazole derivative compound is then subjected to Mitsonubo coupling conditions using isopropanol in the presence of Di-t-butylazodicarboxylate (DBAD) and triphenylphosphine in tetrahydrofuran to provide the corresponding benzyl protected N-1-isopropyl compound (IIIi). The benzyl protected N-1-isopropyl compound can then be debenzylated upon treatment with α-chloroethyl chloroformate (ACE-Cl) and methanol to provide the corresponding free spiropiperidine derivative (IIc). The free spiropiperidine derivative (IIc) can then be acylated as previously described to provide the compounds of Formula (If).

Reaction Scheme VII

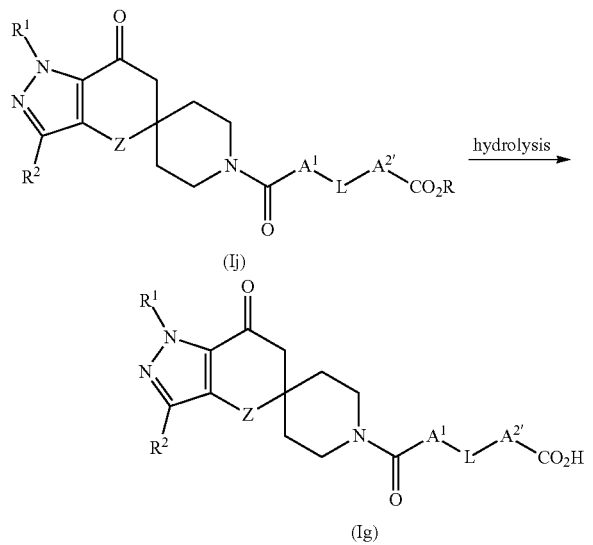

(Ij)

(Ig)

Reaction Scheme VII depicts the hydrolysis of a protected acid intermediate of Formula (Ij) to provide the acid bearing compound of Formula (Ig). For example, the compound of Formula (Ij) where R represents an appropriate acid protecting group such as t-butyl or para-methoxybenzyl can be treated with a strong acid such as trifluoroacetic acid or hydrochloric acid in an appropriate solvent such as dichloromethane to provide the compound of Formula (Ig). In this Reaction Scheme the acid group is shown as appended onto $A^{2'}$ and the acid taken together with $A^{2'}$ represent the group $A^2$ in the compound of Formula (I). It is to be appreciated that the acid group may also be part of $A^1$ in a like manner.

Reaction Scheme VIII

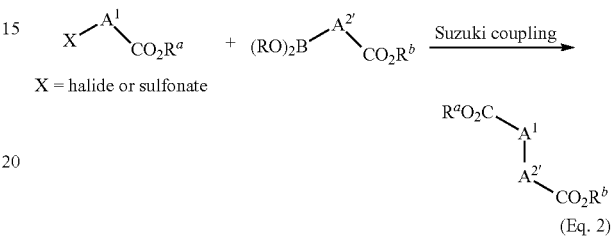

Reaction Scheme VIII provides methods useful for preparing certain intermediates useful in the preparation of compounds of Formula (I). Equation 1 of Reaction Scheme VIII provides a Suzuki-type coupling between an appropriate acid derivative $X\text{-}A^1\text{-}CO_2R^a$ with an appropriate boronate $(RO)_2B\text{-}A^{2'}\text{-}CO_2R^b$ wherein $R^a$ and $R^b$ are differentially protected or one of $R^a$ and $R^b$ is hydrogen, X is a halide or sulfonate such as triflate and R is hydrogen or an alkyl such as methyl. Equation 2 of Reaction Scheme VIII provides another Suzuki-type coupling between $X\text{-}A^1\text{-}CO_2R^a$ with an appropriate boronate $(RO)_2B\text{-}A^{2'}$-tetrazolyl. The Suzuki-type coupling can be carried out as described previously in Reaction Scheme I. The final intermediate compound of Equation 1 and 2 wherein $R^a$ is hydrogen can then be used in acylation type reactions with a compound of Formula (II) as described in Equation 1 of Reaction Scheme I.

Reaction Scheme IX

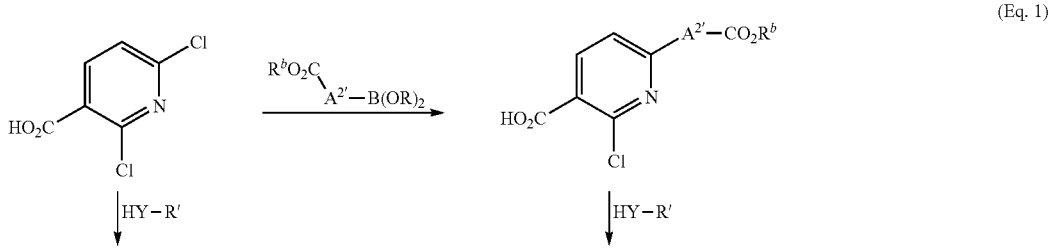

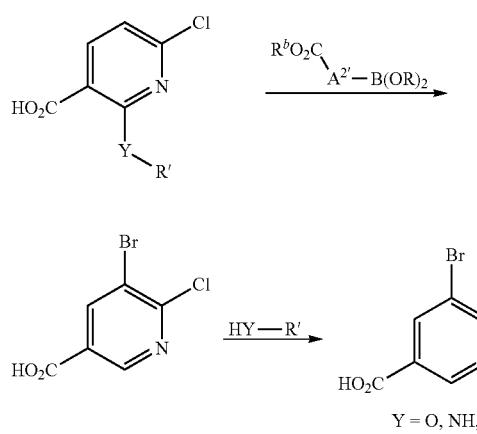
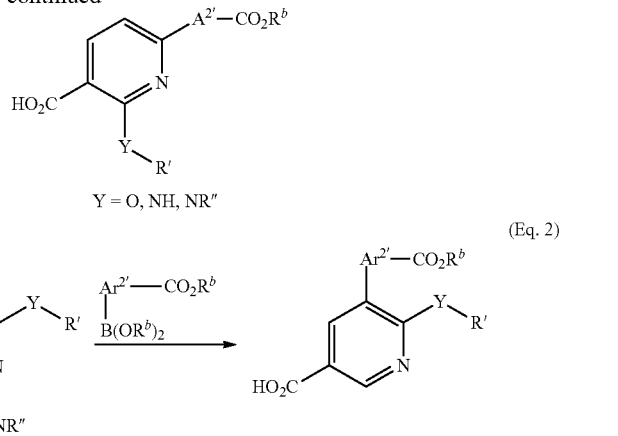

(Eq. 2)

Y = O, NH, NR″

Reaction Scheme IX provides another method useful for preparing certain intermediates useful for preparing compounds of Formula (I). Equation 1 of Reaction Scheme IX depicts the reaction of 2,6-dichloronicotinic acid with an appropriately substituted boronate (where R is hydrogen or alkyl such as methyl and $R^b$ is typically an acid protecting group such as t-butyl) under Suzuki-type coupling conditions to provide the 2-chloro-6-substituted nicotinic acid. The 2-chloro-6-substituted nicotinic acid can then be reacted with an appropriate nucleophile HY-R' (wherein R' is typically alkyl optionally substituted with halo, R″ is typically alkyl such as methyl, ethyl, propyl or isopropyl) to provide the disubstituted nicotinic acid derivative. Alternatively, the reaction can be carried out by first reacting it with the nucleophile HY-R' followed by the Suzuki-type coupling with the boronate as described above. The disubstituted nicotinic acid derivative can then be employed in acylation reactions with compounds of Formula (II) followed by deprotection as necessary as described in Reaction Scheme I to provide compounds of Formula (I) wherein $A^1$ is the substituted pyridine moiety as shown. Equation 2 of Reaction Scheme IX depicts reacting 5-bromo-6-chloronicotinic acid with an appropriate nucleophile HY-R' to provide the 5-bromo-6-substituted nicotinic acid derivative which is then reacted with an appropriate boronate under Suzuli-type coupling conditions to provide the 5,6-disubstituted nicotinic acid derivative. The 5,6-disubstituted nicotinic acid derivative can then be employed in acylation reactions with compounds of Formula (II) followed by deprotection as necessary as previously described in Reaction Scheme I to provide compounds of Formula (I) wherein $A^1$ is the substituted pyridine moiety as shown.

The compounds of the present invention may be isolated and used per se or in the form of their pharmaceutically acceptable salts. In accordance with the present invention, compounds with multiple basic nitrogen atoms can form salts with varying number of equivalents ("eq.") of acid. It will be understood by practitioners that all such salts are within the scope of the present invention.

Pharmaceutically acceptable salts, as used herein in relation to compounds of the present invention, include pharmaceutically acceptable inorganic and organic salts of said compound. These salts can be prepared in situ during the final isolation and purification of a compound, or by separately reacting the compound thereof, with a suitable organic or inorganic acid and isolating the salt thus formed. Representative salts include, but are not limited to, the hydrobromide, hydrochloride, hydroiodide, sulfate, bisulfate, nitrate, acetate, trifluoroacetate, oxalate, besylate, palmitate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate and laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylammonium, dimethylammonium, trimethylammonium, triethylammonium, ethylammonium, and the like. For additional examples see, for example, Berge, et al., J. Pharm. Sci., 66, 1-19 (1977).

Certain compounds of the present invention may exist in more than one crystal form. Polymorphs of compounds of Formula (I) and salts thereof (including solvates and hydrates) form part of this invention and may be prepared by crystallization of a compound of the present invention under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of the present invention followed by gradual or fast cooling. The presence of polymorphs may be determined by solid probe nuclear magnetic resonance (NMR) spectroscopy, infrared (IR) spectroscopy, differential scanning calorimetry, powder X-ray diffraction or such other techniques.

This invention also includes isotopically-labeled compounds, which are identical to those described by Formula (1), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur and fluorine, such as $^2H$, $^3H$, $^{13}C$, $^{14}C$, $^{15}N$, $^{18}O$, $^{17}O$, $^{35}S$, $^{36}Cl$, $^{125}I$, $^{129}I$, and $^{18}F$ respectively. Certain isotopically-labeled compounds of the present invention, for example those into which radioactive isotopes such as $^3H$ and $^{14}C$ are incorporated, are useful in drug and/or substrate tissue distribution assays. Tritiated (i.e., $^3H$), and carbon-14 (i.e., $^{14}C$), isotopes are particularly preferred for their ease of preparation and detectability.

Further, substitution with heavier isotopes such as deuterium (i.e., $^2$H), can afford certain therapeutic advantages resulting from greater metabolic stability, for example increased in vivo half-life or reduced dosage requirements and, hence, may be preferred in some circumstances. Isotopically labeled compounds of the present invention can generally be prepared by carrying out the procedures disclosed in the schemes and/or in the Examples below, by substituting a readily available isotopically labeled reagent for a non-isotopically labeled reagent.

The compounds of the present invention may contain stereogenic centers. These compounds may exist as mixtures of enantiomers or as pure enantiomers. Wherein a compound includes a stereogenic center, the compounds may be resolved into the pure enantiomers by methods known to those skilled in the art, for example by formation of diastereoisomeric salts which may be separated, for example, by crystallization; formation of stereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation.

Certain compounds of the present invention may exist in different stable conformational forms which may be separable. Torsional asymmetry due to restricted rotation about an asymmetric single bond, for example because of steric hindrance or ring strain, may permit separation of different conformers. The compounds of the present invention further include each conformational isomer of compounds of Formula (1) and mixtures thereof.

Compounds of the present invention are useful for treating diseases, conditions and/or disorders modulated by the inhibition of the acetyl-CoA carboxylases enzyme(s) (in particular, ACC1 and ACC2); therefore, another embodiment of the present invention is a pharmaceutical composition comprising a therapeutically effective amount of a compound of the present invention and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The dissolution rate of poorly water-soluble compounds may be enhanced by the use of a spray-dried dispersion, such as those described by Takeuchi, H., et al. in "Enhancement of the dissolution rate of a poorly water-soluble drug (tolbutamide) by a spray-drying solvent depostion method and disintegrants" *J. Pharm. Pharmacol.*, 39, 769-773 (1987); and EP0901786 B1 (US2002/009494), incorporated herein by reference. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of the present invention. The term "solvate" refers to a molecular complex of a compound represented by Formula (I) (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by the inhibition of the acetyl-CoA carboxylases enzyme(s) in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the inhibition of acetyl-CoA carboxylases enzyme(s).

One aspect of the present invention is the treatment of obesity, and obesity-related disorders (e.g., overweight, weight gain, or weight maintenance).

Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of the present invention is for the treatment or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, and diabetic complications (such as atherosclerosis, coronary heart disease, stroke, peripheral vascular disease, nephropathy, hypertension, neuropathy, and retinopathy).

In yet another aspect of the present invention is the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology*, 7(2), (2005); and Alberti, K. G., et al., "The Metabolic Syndrome—A New Worldwide Definition," *Lancet*, 366, 1059-62 (2005). Preferably, administration of the compounds of the present invention provides a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant ($p<0.05$) reduction in glucose serum levels.

In yet another aspect of the invention is the treatment of nonalcoholic fatty liver disease (NAFLD) and heptic insulin resistance.

For a normal adult human having a body weight of about 100 kg, a dosage in the range of from about 0.001 mg to about 10 mg per kilogram body weight is typically sufficient, preferably from about 0.01 mg/kg to about 5.0 mg/kg, more preferably from about 0.01 mg/kg to about 1 mg/kg. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of the present invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable anti-obesity agents include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $β_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine. Preferably, compounds of the present invention and combination therapies are administered in conjunction with exercise and a sensible diet.

Suitable anti-diabetic agents include a sodium-glucose co-transporter (SGLT) inhibitor, a phosphodiesterase (PDE)-10 inhibitor, a diacylglycerol acyltransferase (DGAT) 1 or 2 inhibitor, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, cam iglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) agonist (e.g., Byetta™, exendin-3 and exendin-4), a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 inhibitor (e.g., reservatrol), a dipeptidyl peptidease IV (DPP-IV) inhibitor (e.g., sitagliptin, vildagliptin, alogliptin and saxagliptin), an insulin secreatagogue, a fatty acid oxidation inhibitor, an A2 antagonist, a c-jun amino-terminal kinase (JNK) inhibitor, insulin, an insulin mimetic, a glycogen phosphorylase inhibitor, a VPAC2 receptor agonist and a glucokinase activator. Preferred anti-diabetic agents are metformin, a glucagon-like peptide 1 (GLP-1) agonist (e.g, Byetta™) and DPP-IV inhibitors (e.g., sitagliptin, vildagliptin, alogliptin and saxagliptin).

All of the above recited U.S. patents and publications are incorporated herein by reference.

The Examples set forth herein below are for illustrative purposes only. The compositions, methods, and various parameters reflected herein are intended only to exemplify various aspects and embodiments of the invention, and are not intended to limit the scope of the claimed invention in any way.

EXAMPLES

The compounds and intermediates described below were generally named according to the IUPAC (International Union for Pure and Applied Chemistry) recommendations on Nomenclature of Organic Chemistry and the CAS Index rules. Unless noted otherwise, all reactants were obtained commercially. All of the references cited herein below are incorporated by reference.

Flash chromatography was performed according to the method described by Still et al., J. Org. Chem., 1978, 43, 2923.

All Biotage® purifications, discussed herein, were performed using either a 40M or 40S Biotage® column containing KP-SIL silica (40-63 µM, 60 Angstroms) (Bioatge AB; Uppsala, Sweden).

All Combiflash® purifications, discussed herein, were performed using a CombiFlash® Companion system (Teledyne Isco; Lincoln, Nebr.) utilizing packed RediSep® silica columns Mass Spectra were recorded on a Waters (Waters Corp.; Milford, Mass.) Micromass Platform II spectrometer. Unless otherwise specified, mass spectra were recorded on a Waters (Milford, Mass.) Micromass Platform II spectrometer.

Proton NMR chemical shifts are given in parts per million downfield from tetramethylsilane and were recorded on a Varian Unity 400 or 500 MHz (megaHertz) spectrometer (Varian Inc.; Palo Alto, Calif.). NMR chemical shifts are given in parts per million downfield from tetramethylsilane (for proton) or fluorotrichloromethane (for fluorine).

The preparations described below were used in the synthesis of compounds exemplified in the following examples.

Preparation of Intermediates and Starting Materials

Intermediate 1

5-(4-(Tert-butoxycarbonyl)phenyl)-6-ethoxynicotinic acid, shown below, was prepared as follows.

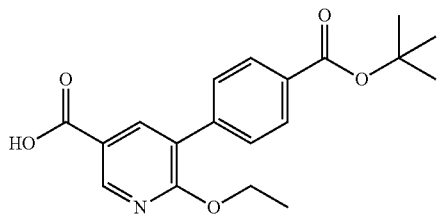 [SMILES: CCOc1ncc(C(=O)O)cc1-c1ccc(C(=O)OC(C)(C)C)cc1]

Step 1. 5-Bromo-6-ethoxynicotinic acid, shown below, was prepared as follows.

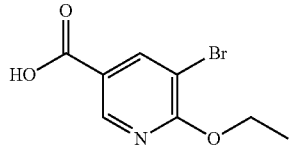

A slurry of 5-bromo-6-chloronicotinic acid (240 mg, 1.0 mmol) and sodium ethoxide (138 mg, 2.0 mmol) in anhydrous ethanol (2 mL) was heated under microwave conditions at 100° C. for 15 min; an additional portion of sodium ethoxide (79 mg, 1.0 mmol) was added and heating was continued for 1 hr. After cooling the reaction mixture was adjusted to a pH of 4 with 1 N aqueous hydrochloric acid, the resulting solids collected and dried in vacuo to afford 5-bromo-6-ethoxynicotinic acid (140 mg). 1H NMR (400 MHz, DMSO-d6) d ppm 1.33 (t, J=7.02 Hz, 3H) 4.43 (q, J=7.09 Hz, 2H) 8.32 (d, J=2.15 Hz, 1H) 8.64 (d, J=1.95 Hz, 1H) 13.28 (br. s., 1H); m/z=248.2 (M+1).

Step 2. The title compound, shown above, was prepared as follows: A slurry of 5-bromo-6-ethoxynicotinic acid (60 mg, 0.24 mmol), 4-tert-butoxycarbonylphenylboronic acid (70 mg, 0.32 mmol), 2 N aqueous sodium carbonate (0.37 mL, 0.73 mmol) and palladium 1,1'-bis(diphenylphosphino) ferrocene dichloride (9 mg, 0.05 mmol) in p-dioxane (2 mL) were heated at 100° C. for 2 hr. An additional portion of 4-tert-butylcarboxylphenylboronic acid (70 mg, 0.32 mmol) and palladium 1,1'-bis(diphenylphosphino)ferrocene dichloride (9 mg, 0.05 mmol) were added and heating was continued for 1.5 hr. The reaction mixture was cooled, diluted into water, pH adjusted to ~5 using 1 N aqueous hydrochloric acid. This mixture was extracted with ethyl acetate (3×), the combined organic layers washed with brine, dried over magnesium sulfate and concentrated in vacuo to afford the title compound (100 mg), which was utilized without further purification; m/z=344.2 (M+1).

Intermediate 2

2-(4-(Tert-butoxycarbonyl)phenyl)-6-(dimethylamino) isonicotinic acid, shown below, was prepared as follows.

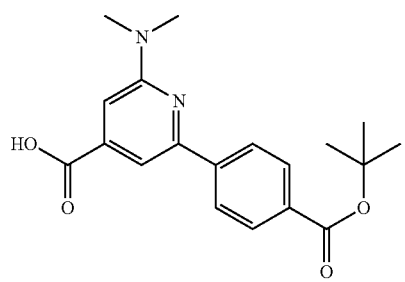 [SMILES: CN(C)c1cc(C(=O)O)cc(-c2ccc(C(=O)OC(C)(C)C)cc2)n1]

Step 1. 2-Chloro-6-(dimethylamino)isonicotinic acid, hydrochloride salt, shown below, was prepared as follows.

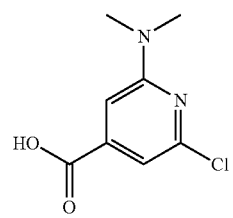

2,6-Dichloroisonicotinic acid (2.00 g, 10.42 mmol) was placed in a pressure tube and a solution of dimethylamine in tetrahydrofuran (26 mL, 2 M, 52 mmol) added. The vessel was sealed and heated for 22 h at 80° C. The mixture was cooled to room temperature, transferred to a round-bottom flask and concentrated to dryness. The resulting white semi-solid was taken up in 30 mL of 0.1 N sodium hydroxide solution. 1 N HCl was added dropwise with stirring to adjust the pH of the solution to ca. 3.5, at which point a pale yellow solid formed. This was collected by filtration and dried under vacuum at 45° C. overnight to provide 2-chloro-6-(dimethylamino)isonicotinic acid inner salt (916 mg, 44%). Further acidification of the aqueous solution to pH 1 resulted in the formation of a bright yellow solid, which was also collected and dried under vacuum to give 2-chloro-6-(dimethylamino) isonicotinic acid hydrochloride (1.15 g, 46%). m/z: 201+[M+H]; 199−[M−H]. For the HCl salt: $^1$H NMR (400 MHz, DMSO-d$_6$) δ ppm 13.64 (br. s., 1H), 6.96 (d, J=1.0 Hz, 1H), 6.89 (d, J=0.8 Hz, 1H), 3.06 (s, 6H), 2.53 (t, J=5.1 Hz, 1H).

For the inner salt: $^1$H NMR (400 MHz, DMSO-d$_6$) δ ppm 6.95 (s, 1H), 6.88 (s, 1H), 3.04 (s, 6H).

Step 2. 2-(4-(tert-butoxycarbonyl)phenyl)-6-(dimethylamino)isonicotinic acid, shown below, was prepared as follows.

2-Chloro-6-(dimethylamino)isonicotinic acid (450 mg, 2.24 mmol), 4-(tert-butoxycarbonyl)benzene boronic acid (648 mg, 2.92 mmol), 1,4-dioxane (7.5 mL) and sodium carbonate (713 mg, 6.73 mmol) dissolved in water (3.36 mL) were placed in a flask and the mixture bubbled with nitrogen while stirring for 10 min. Palladium(II) acetate (20 mg, 0.09 mmol) and 2-dicyclohexylphosphino-2',6'-dimethoxybiphenyl (75 mg, 0.18 mmol) were then added together and the vessel flushed with nitrogen, sealed, and heated at 90° C. for 5 h. The mixture was then cooled to room temperature, diluted with ethyl acetate (50 mL), acidified to pH 2 with 1.5 N HCl and filtered through a pad of celite. The layers were separated and the aqueous portion extracted with ethyl acetate (2×50 mL). The combined organic portions were treated with anhydrous sodium sulfate and decolorizing charcoal and stirred for 30 min before filtering. The solution was concentrated to dryness and the residue purified by trituration with a mixture of methyl tert-butyl ether (5 mL) and heptane (100 mL). The solids were collected by filtration and dried to give 2-(4-(tert-butoxycarbonyl)phenyl)-6-(dimethylamino)isonicotinic acid (502 mg, 65%) as a pale yellow powder. m/z: 343+[M+H]; 341−[M−H]; $^1$H NMR (400 MHz, CDCl$_3$) δ ppm 8.12-8.21 (m, 2H), 8.04-8.11 (m, 2H), 7.67 (s, 1H), 7.16 (s, 1H), 3.23 (s, 6H), 1.64 (s, 9H).

Intermediate 3

2-(4-(Tert-butoxycarbonyl)phenyl)-6-ethoxyisonicotinic acid, shown below, was prepared as follows.

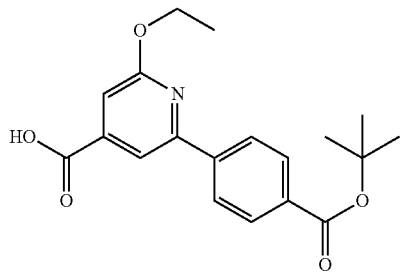 [SMILES: CCOc1cc(C(=O)O)cc(-c2ccc(C(=O)OC(C)(C)C)cc2)n1]

Sodium (65 mg, 3 mmol) was added to absolute ethanol (3 mL) under argon at RT. After completed dissolution of the sodium, the freshly prepared ethoxide solution was added to 2,6-dichloronicotinic acid 1 (0.5 g, 2.6 mmol). This mixture was heated in a microwave at 150° C. for 3 hrs. The mixture was concentrated to dryness to provide crude 2-chloro-6-ethoxyisonicotinic acid (0.5 g), which was used without purification. m/z: 202+[M+H]

The crude 2-chloro-6-ethoxyisonicotinic acid (0.5 g, ca. 2.6 mmol), 4-(tert-butoxycarbonyl) benzene boronic acid (0.5 g, 2.2 mmol), potassium carbonate (0.5 g, 3.6 mmol) and water (0.1 mL) in 1,2-dimethoxyethane (10 mL) were stirred and degassed for 10 min. Tetrakis(triphenylphosphine)palladium (0.1 g, 0.08 mmol) was then added. The sealed tube was then heated over night at 90° C. After cooling the reaction was passed through a plug a celite and partitioned between dichloromethane and water. The organic solution was concentrated and the crude residue purified by chromatography (silica gel, 10% methanol in dichloromethane) to afford the title compound (97 mg, 20%). $^1$H NMR (400 MHz, CDCl$_3$) δ ppm 8.11 (2H, d), 8.08 (2H, d), 7.96 (1H, s), 7.34 (1H, s), 4.54 (2H, qd), 1.61 (9H, s), 1.46 (3H, t); m/z: 344+[M+H].

Intermediate 4

2-((2-Tert-butoxy-2-oxoethyl)(methyl)amino)-6-methoxyisonicotinic acid, shown below, was prepared as follows.

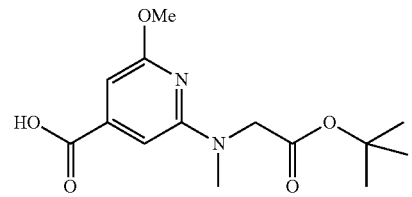 [SMILES: COc1cc(C(=O)O)cc(N(C)CC(=O)OC(C)(C)C)n1]

A slurry of 2-chloro-6-methoxyisonicotinic acid (100 mg, 0.53 mmol), sarcosine tert-butyl ester (116 mg, (0.64 mmol), chloro(di-2-norborylphosphino)(2-dimethylaminomethylferrocen-1yl)palladium (II) (9.8 mg, 0.02 mmol) and sodium tert-butoxide (128 mg, 1.3 mmol) in p-dioxane (3 mL) were stirred at 110° C. for 18 hr. The reaction mixture was cooled and the solvent removed in vacuo. The residue was diluted with water, pH adjusted to 4 with 1N aqueous hydrochloric acid and extrated with ethyl acetate (3×10 mL). The combined organic layer was dried over magnesium sulfate, filtered, concentrated in vacuo and the residue flash chromatographed (0-10% methanol/dichloromethane) to afford the title compound (60 mg) as a yellow solid. m/z=297.5 (M+1).

Intermediate 5

2-(4-(Tert-butoxycarbonyl)phenyl)-6-methoxyisonicotinic acid, shown below, was prepared as follows.

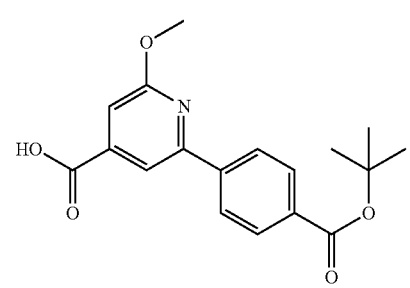 [SMILES: COc1cc(C(=O)O)cc(-c2ccc(C(=O)OC(C)(C)C)cc2)n1]

2-Chloro-6-methoxyisonicotinic acid (15.0 g, 80.0 mmol), tert-butyl 4-(4,4,5,5-tetramethyl-1,3,2-dioxaborolan-2-yl)benzoate (29.2 g, 96.0 mmol), 1,4-dioxane (500 mL) and sodium carbonate (25.4 g, 240 mmol) dissolved in water (160 mL) were combined in a 1 L, 3 necked flask equipped with an internal thermometer, condenser and nitrogen inlet. The solution was degassed by bubbling with nitrogen for 15 min while stirring. Tetrakis(triphenylphosphine)palladium (3.70 g, 3.20 mmol) was then added and the mixture heated to reflux for 17 h. The mixture was then cooled to room temperature and concentrated under vacuum to give a thick brown suspension, which was portioned between ethyl acetate (400 mL) and water (150 mL). The aqueous layer was separated and extracted with further ethyl acetate (2×100 mL). The organic portions were combined and washed with 1 N HCl and water, and the black solids removed by filtration through a pad of celite. The aqueous layer was discarded and the organic solution dried over anhydrous magnesium sulfate and filtered. The solution was then treated with decolorlizing charcoal and heated to 70° C. for 20 min. The solution was then filtered through celite while hot and the solvent removed under vacuum to afford a yellow powder. This material was purified by addition of methyl tert-butyl ether (55 mL) followed by the slow addition of 1.85 L heptane with stirring. The mixture was stirred for 2 days and then filtered to give 2-(4-(tert-butoxycarbonyl)phenyl)-6-methoxyisonicotinic acid (22.01 g, 84%) as a pale yellow powder. $^1$H NMR (400 MHz, CHLOROFORM-d) δ ppm 1.61 (s, 9H) 4.08 (s, 3H) 7.34 (d, J=0.98 Hz, 1H) 7.97 (d, J=1.17 Hz, 1H) 8.09 (s, 2H) 8.13 (s, 2H); m/z: 330.2+[M+H].

Intermediate 6

6-(4-(Tert-butoxycarbonyl)phenyl)-2-(methylamino) nicotinic acid, shown below, was prepared as follows.

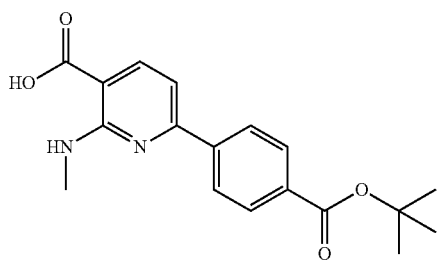 [SMILES: CNc1nc(-c2ccc(C(=O)OC(C)(C)C)cc2)ccc1C(=O)O]

Step 1. 6-Chloro-2-(methylamino)nicotinic acid, shown below, was prepared as follows.

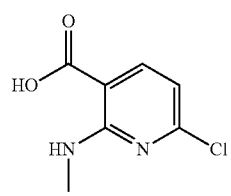

To a steel autoclave was added 2,6-dichloronicotinic acid (tech.) (30 g, 156.2 mmoles), tetrahydrofuran (30 mL) and monomethylamine (68.2 mL. 33 wt % in ethanol, 500 mmol). The reaction vessel was heated at 100° C. for 4 h. The reaction mixture was cooled and the solution transferred from the autoclave to a 500 mL flask and concentrated under vacuum to give a green solid. The solid was dissolved in 300 mL MeOH and 1.2 L EtOAc, poured into a separatory funnel and washed with 1N HCl (2×300 mL) and brine. The organic solution was then concentrated to dryness to yield 6-chloro-2-(methylamino)nicotinic acid (29 g, 96%) as an off-white solid.

1H NMR (400 MHz, DMSO-d6) δ ppm 13.14 (br. s., 1H), 8.17 (d, J=2.7 Hz, 1H), 8.00 (d, J=8.0 Hz, 1H), 7.57 (br. s., 1H), 6.58 (d, J=8.0 Hz, 1H), 2.89 (d, J=4.1 Hz, 3H).

m/z: 187+[M+H]; 185−[M−H]

Step 2. To a 2 L 3-neck flask was added 6-chloro-2-(methylamino)nicotinic acid (22.9 g, 122.6 mmol), tert-butyl 4-(4,4,5,5-tetramethyl-1,3,2-dioxaborolan-2-yl)benzoate (31.2 g, 102.6 mmol), 1,4-dioxane (1.02 L) and sodium carbonate (32.6 g, 307.7 mmol) dissolved in water (300 mL). The mixture was bubbled with dry nitrogen while stirring for 20 min. Tetrakis(triphenylphosphine)palladium (5.93 g, 5.13 mmol) was then added and the mixture heated to reflux (89° C.) for 2 h. The reaction mixture was cooled to room temperature, water (250 mL) added, and the mixture stirred for 10 min. The mixture was extracted with 1.5 L of ethyl acetate and the organic layer separated and washed with 10% aqueous sodium carbonate (250 mL), 1 N HCl (2×250 mL) and brine. The solution was then concentrated to a minimum stirring volume, methanol (650 mL) added and the mixture heated at reflux to dissolve the solids. 300 mL MeOH was removed by distillation and 100 mL water added. The mixture was then cooled to room temperature and the product collected by filtration, washed with 150 mL of 2:1 methanol/water, and dried in the vacuum oven to afford the title compound (24 g, 71%) as a yellow solid. 1H NMR (400 MHz, CHLOROFORM-d) δ ppm 8.27 (d, J=8.2 Hz, 1H), 8.13-8.21 (m, 2H), 8.03-8.13 (m, 2H), 7.82 (br. s., 1H), 7.11 (d, J=8.0 Hz, 1H), 3.21 (s, 3H), 1.63 (s, 9H); m/z: 329+[M+H]; 327−[M−H].

Intermediate 7

6-(3-(Tert-butoxycarbonyl)phenyl)-2-(ethylamino)nicotinic acid, shown below, was prepared as follows.

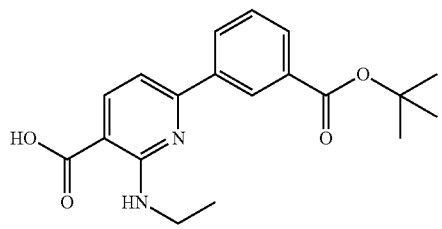 [SMILES: CCNc1nc(-c2cccc(C(=O)OC(C)(C)C)c2)ccc1C(=O)O]

Step 1. 6-(3-(tert-butoxycarbonyl)phenyl)-2-chloronicotinic acid, shown below, was prepared as follows.

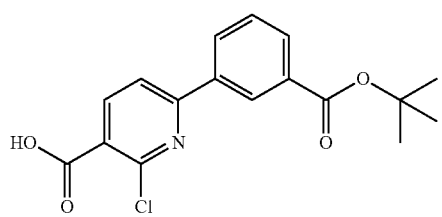 [SMILES: CC(C)(C)OC(=O)c1cccc(-c2ccc(C(=O)O)c(Cl)n2)c1]

2,6-Dichloronicotinic acid (1.20 g, 6.25 mmol), 3-(tert-butoxycarbonyl)benzene boronic acid (2.08 g, 9.10 mmol), potassium carbonate (2.60 g, 18.8 mmol), tetrakis(triphenylphosphine)palladium (0.72 g, 0.62 mmol), degassed 1,2-dimethoxyethane (30 mL) and water (0.5 mL) were combined under an argon atmosphere and the mixture heated at 90° C. overnight. The reaction mixture was then cooled to room temperature, diluted with water (100 mL) and extracted with ethyl acetate (2×150 mL). The aqueous layer was acidified to pH 3-4 using 2N HCl solution and extracted with ethyl acetate (2×200 mL). The combined organic portions were dried over anhydrous sodium sulfate and concentrated. The residue was purified by column chromatography (silica gel, 20% methanol/dichloromethane) and the product containing fractions concentrated to give a solid, which was triturated with 2:1 heptane/ethyl acetate to give pure 6-(3-(tert-butoxycarbonyl)phenyl)-2-chloronicotinic acid (1.4 g, 67%) as an off-white foam. $^1$H NMR (400 MHz, CD$_3$OD) δ ppm 8.64 (s, 1H), 8.34 (d, 1H), 8.29 (d, 1H), 8.04 (d, 1H), 7.95 (d, 1H), 7.59 (t, 1H), 1.60 (s, 9H); m/z 334 [M+H].

Step 2. 6-(3-(Tert-butoxycarbonyl)phenyl)-2-chloronicotinic acid (500 mg, 1.50 mmol) was dissolved in a 2 M solution of ethylamine in tetrahydrofuran (7.0 mL, 14.0 mmol) and the mixture heated using a microwave at 140° C. for 4 h. The solution was then concentrated to dryness and the crude mixture purified by column chromatography (silica gel, 10% methanol/dichloromethane). The solid obtained was triturated with ethyl acetate/heptane (1:4) and filtered to afford the title compound (330 mg, 64% yield) as a yellow solid. $^1$H NMR (400 MHz, CDCl$_3$) δ ppm 8.70 (s, 1H), 8.27 (dd, 2H), 8.06 (d, 1H), 7.85 (br.s, 1H), 7.52 (t, 1H), 7.09 (d, 1H), 3.71 (q, 1H), 1.62 (s, 9H), 1.27 (t, 3H); m/z 343 [M+H].

Intermediate 8

4-(3-(Tert-butoxycarbonyl)phenyl)-1H-pyrrolo[2,3-b]pyridine-2-carboxylic acid, shown below, was prepared as follows:

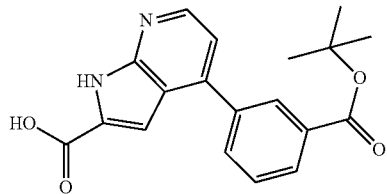 [SMILES: CC(C)(C)OC(=O)c1cccc(-c2ccnc3[nH]c(C(=O)O)cc23)c1]

Step 1. Methyl 4-(3-(tert-butoxycarbonyl)phenyl)-1H-pyrrolo[2,3-b]pyridine-2-carboxylate, shown below, was prepared as follows:

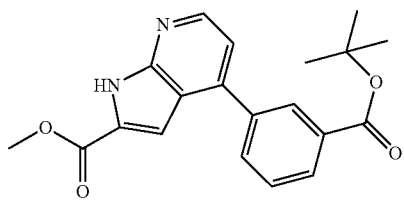 [SMILES: COC(=O)c1cc2c(-c3cccc(C(=O)OC(C)(C)C)c3)ccnc2[nH]1]

A stirred slurry of methyl 4-chloro-7-azaindole-2-carboxylate (100 mg, 0.48 mmol), tert-butyl 3-(hydroxy(methyl)boryl)benzoate (137 mg, 0.62 mmol), potassium phosphate (309 mg, 1.42 mmol), tetrakis(triphenylphosphine) palladium (28 mg, 0.02 mmol) in p-dioxane (3 mL)/water (1 mL) were heated at 100° C. for 15 hr. The reaction mixture was cooled, concentrated in vacuo and flash chromatographed (0-100% ethyl acetate:heptanes) to afford methyl 4-(3-(tert-butoxycarbonyl)phenyl)-1H-pyrrolo[2,3-b]pyridine-2-carboxylate as a white powder (148 mg). 1H NMR (400 MHz, CHLOROFORM-d) d ppm 1.62 (s, 9H) 3.99 (s, 3H) 7.28 (d, J=5.23 Hz, 1H) 7.36 (d, J=2.62 Hz, 1H) 7.59 (t, 1H) 7.90 (d, 1H) 8.09 (d, 1H) 8.35 (t, 1H) 8.64 (d, J=4.70 Hz, 1H); m/z (M+1)=353.2.

Step 2. To a stirred solution of methyl 4-(3-(tert-butoxycarbonyl)phenyl)-1H-pyrrolo[2,3-b]pyridine-2-carboxylate (145 mg, 0.41 mmol) in methanol (2 mL)/tetrahydrofuran (2 mL) was added 1N aqueous lithium hydroxide (0.82 mL, 0.82 mmol). After 18 hr, the reaction mixture was concentrated in vacuo, diluted into water, pH adjusted to ~5 with 1N aqueous hydrochloric acid, the yellow solids collected by filtration and dried in vacuo to afford the title compound (122 mg). m/z=339.5 (M+1); $^1$H NMR (400 MHz, DMSO-d$_6$) δ ppm 12.56 (s, 1H) 8.47 (d, J=4.88 Hz, 1H) 8.24 (t, J=1.66 Hz, 1H) 8.01 (tt, J=8.36, 1.29 Hz, 2H) 7.69 (t, J=7.80 Hz, 1H) 7.31 (d, J=4.88 Hz, 1H) 7.15 (d, J=2.15 Hz, 1H) 1.52-1.59 (m, 9H).

Intermediate 9

1-isopropyl-4,6-dihydrospiro[indazole-5,4'-piperidin]-7 (1H)-one, shown below, was prepared as follows.

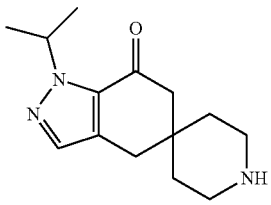 [SMILES: CC(C)n1ncc2c1C(=O)CC1(CCNCC1)C2]

Step 1. tert-butyl 9-oxo-3-azaspiro[5.5]undec-7-ene-3-carboxylate, shown below, was prepared as follows.

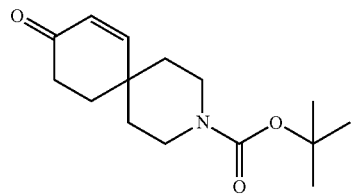 [SMILES: CC(C)(C)OC(=O)N1CCC2(C=CC(=O)CC2)CC1]

Methyl vinyl ketone (146 mL) was added to a solution of tert-butyl 4-formylpiperidine-1-carboxylate (375 g) in tetrahydrofuran (18 L). The reaction mixture was cooled to −5° C. and a solution of potassium hydroxide in ethanol (3N, 0.243 L) was added dropwise over 10 minutes. The reaction mixture was allowed to warm to room temperature and stirred for 16 hours. Cyclohexane (10 L) was added and the solution was washed with saturated sodium chloride (3×10 L). The organic layer was concentrated to an oil. This oil was dissolved in 2 L of 80:20 cyclohexane/ethyl acetate and filtered through Celite® to remove insoluble material. The filtrate was purified via flash column chromatography (70:30 hexane/ethyl acetate) to afford the product as an oil. The oil was triturated in hexanes to afford the desired product as a white solid (131 g, 28%).

Step 2. (E)-tert-butyl 10-((dimethylamino)methylene)-9-oxo-3-azaspiro[5.5]undec-7-ene-3-carboxylate, shown below, was prepared as follows.

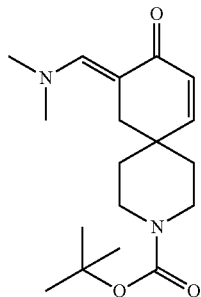 [SMILES: CN(C)/C=C1\CC2(C=CC1=O)CCN(C(=O)OC(C)(C)C)CC2]

tert-Butyl 9-oxo-3-azaspiro[5.5]undec-7-ene-3-carboxylate (101 g) and tris(dimethylaminomethane) (133 mL) were dissolved in toluene (800 mL) and heated to reflux for 17 hours. The reaction mixture was concentrated to a minimum stirring volume and ethyl acetate (600 mL) was added. This mixture was heated to reflux and heptane (1.2 L) was added over 20 minutes. The hot solution was cooled to room temperature over 3 hours. The solids were filtered through a course glass frit and washed with heptane (300 mL). The resulting solid was dried in a vacuum oven at 40° C. for 3 hours to afford the desired product as a yellow solid (107 g). ¹H NMR (400 MHz, CDCl₃) δ ppm 7.48 (s, 1H), 6.57 (d, J=9.97 Hz, 1H), 5.99 (d, J=10.16 Hz, 1H), 3.32-3.51 (m, 4H), 3.06 (s, 6H), 2.72 (s, 2H), 1.57-1.66 (m, 2H), 1.41-1.53 (m, 11H).

Step 3. tert-Butyl 1-isopropyl-1,4-dihydrospiro[indazole-5,4'-piperidine]-1'-carboxylate, shown below, was prepared as follows.

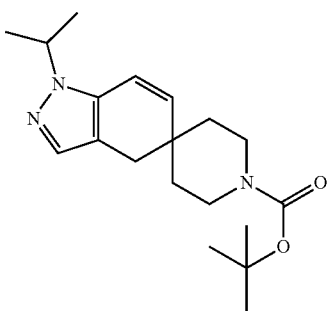 [SMILES: CC(C)n1ncc2c1C=CC1(CCN(C(=O)OC(C)(C)C)CC1)C2]

(E)-tert-Butyl 10-((dimethylamino)methylene)-9-oxo-3-azaspiro[5.5]undec-7-ene-3-carboxylate (107 g) was taken up in toluene (700 mL) and isopropyl hydrazine (44.4 g) was added. The reaction was stirred at reflux for 4 hours. The reaction was cooled to room temperature and ethyl acetate was added (500 mL). The reaction solution was washed with citric acid (2×300 mL, 10% aqueous), and water (400 mL). The organic layer concentrated in vacuo to afford tert-butyl 1-isopropyl-1,4-dihydrospiro[indazole-5,4'-piperidine]-1'-carboxylate as a yellow solid (109 g). ¹H NMR (400 MHz, CDCl₃) δ ppm 7.25 (s, 1H) 6.42 (dd, J=10.05, 0.49 Hz, 1H) 5.84 (d, J=9.95 Hz, 1H) 4.42-4.52 (m, 1H) 3.36-3.53 (m, 4H) 2.62 (s, 2H) 1.56-1.68 (m, 2H) 1.45-1.55 (m, 17H).

Step 4. tert-butyl 1-isopropyl-7-oxo-1,4,6,7-tetrahydrospiro[indazole-5,4'-piperidine]-1'-carboxylate, shown below, was prepared as follows.

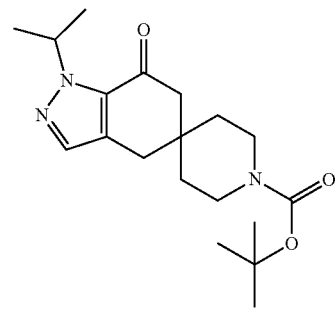 [SMILES: CC(C)n1ncc2c1C(=O)CC1(CCN(C(=O)OC(C)(C)C)CC1)C2]

To a solution of tert-butyl 1-isopropyl-1,4-dihydrospiro[indazole-5,4'-piperidine]-1'-carboxylate (109 g) in methanol (1 L) was added N-bromo succinimide (61.4 g). The reaction was stirred for 1 hour. The reaction was quenched with sodium thiosulfate (10 g in 300 mL water) and then distilled to a final volume of 500 mL. The solution was cooled to ambient temperature and 2-methyl tetrahydrofuran (1 L) and water (100 mL) were added. The organic layer was removed and the aqueous layer was extracted with 2-methyl tetrahydrofuran. The organic layers were combined, washed with aqueous sodium hydroxide (1 N, 250 mL), water and saturated, aqueous sodium chloride. The organic layer was dried over sodium sulfate, filtered and concentrated to an orange oil. The oil was dissolved in tetrahydrofuran (500 mL) and potassium tert-butoxide (76.8 g) in tetrahydrofuran (500 mL) was added. The solution was heated to 60° C. and stirred for 1 hour. Aqueous hydrochloric acid (1 N, 1 L) was added and the solution was stirred for 30 minutes. The phases were separated and the aqueous layer was extracted with ethyl acetate (700 mL). The organic layers were combined, washed with water (400 mL) and saturated, aqueous sodium chloride (100 mL). The organic layer was dried over sodium sulfate, filtered and concentrated in vacuo to give a residue. The residue was dried in a vacuum oven at 40° C. for 16 hours to afford the title compound as an orange wax (117 g). ¹H NMR (400 MHz, CDCl₃) δ ppm 7.35 (s, 1H), 5.32-5.42 (m, 1H), 3.29-3.51 (m, 4H), 2.73 (s, 2H), 2.51 (s, 2H), 1.47-1.57 (m, 4H), 1.42-1.46 (m, 15H); +ESI MS (M+H)=348.5.

Step 5. 1-isopropyl-4,6-dihydrospiro[indazole-5,4'-piperidin]-7(1H)-one, shown below, was prepared as follows.

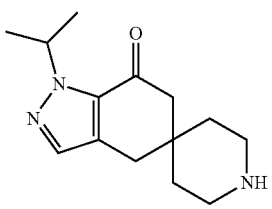 [SMILES: CC(C)n1ncc2c1C(=O)CC1(CCNCC1)C2]

tert-Butyl 9-oxo-3-azaspiro[5.5]undec-7-ene-3-carboxylate (250 g), and tris(dimethylaminomethane) (325 mL) were dissolved in toluene (1.9 L) and heated at reflux for 4 hours. The mixture was distilled and concentrated to a minimum stirring volume (110° C.) and then toluene (1.9 L) was added. The reaction was redistilled to a minimum stirring volume and cooled to room temperature. Toluene (1.8 L) and isopropyl hydrazine hydrochloride (135 g) were added and the solution was heated to reflux for 5 hours. The reaction was cooled to room temperature and was then washed with citric acid (10% aqueous, 2×150 mL) and water (200 mL), and then the organic layer was distilled to a minimum stirring volume. Methanol (2 L) was added and distilled to a minimum stirring volume. This was repeated with methanol (2 L). The solution was redissolved in methanol (2.5 L) and N-bromosuccinimide (176 g) was added in one portion. The solution was stirred at 23° C. for 2 hours. Aqueous sodium thiosulfate solution (5 wt %, 0.5 L) was added and the mixture was stirred for 15 minutes. The reaction mixture was concentrated via distillation (45° C., 210 mm Hg) to ~0.5 L and then 2-methyl tetrahydrofuran (2.5 L) was added. After stirring for 15 minutes the aqueous layer was discarded. The organic layer was concentrated to ~0.2 L and tetrahydrofuran (0.5 L) was added. To the mixture was added a potassium tert-butoxide solution in tetrahydrofuran (1.9 L, 1 M solution). The solution was heated to 60° C. and stirred for 1 hour. After cooling to room temperature, aqueous hydrochloric acid (1 N, 2.2 L) was added over 20 minutes. The mixture was stirred at room temperature for 20 minutes, and then the layers were allowed to separate. The aqueous layer was removed and back extracted with ethyl acetate (1.75 L). The combined organic layers were washed with water (1 L) and the organic layer concentrated via distillation (4 L solvent removed). Ethyl acetate (1.8 L) was added and the solution was concentrated to a minimum stirring volume. Ethyl acetate (3 L) and methanol (0.8 L) were added and the solution was cooled to 0° C. Acetyl chloride (401 mL) was added dropwise over 20 minutes and the solution was stirred at 0° C. for 4 hours. The precipitate was collected by filtration under nitrogen. The filtrate was washed with ethyl acetate (0.5 L) and dried in a vacuum oven at 40° C. to afford 1-isopropyl-4,6-dihydrospiro[indazole-5,4'-piperidin]-7 (1H)-one as an off-white solid (241 g). $^1$H NMR (400 MHz, CD$_3$OD) δ ppm 7.43 (s, 1H), 5.32-5.42 (m, 1H), 3.15-3.25 (m, 4H), 2.89 (s, 2H), 2.64 (s, 2H), 1.69-1.90 (m, 4H), 1.37-1.45 (m, 6H); +ESI (M+H)=248.4

Intermediate 10

1-tert-butyl-4,6-dihydrospiro[indazole-5,4'-piperidin]-7 (1H)-one, shown below, was prepared as follows.

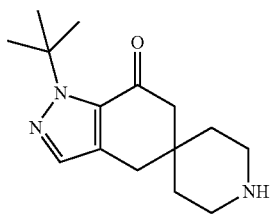 [SMILES: CC(C)(C)n1ncc2c1C(=O)CC1(CCNCC1)C2]

Step 1. Benzyl 10-((dimethylamino)methylene)-9-oxo-3-azaspiro[5.5]undec-7-ene-3-carboxylate, shown below, was prepared as follows.

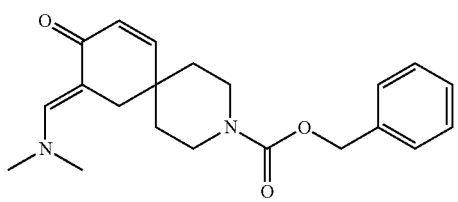 [SMILES: CN(C)/C=C1\CC2(C=CC1=O)CCN(C(=O)OCc1ccccc1)CC2]

9-oxo-3-aza-spiro[5.5]undec-7-ene-3-carboxylic acid benzyl ester (15.2 g, 51 mmol) was dissolved in 180 mL of toluene and tris(dimethylamino)methane (22.2 g, 27 mmol) was added. The reaction was heated to reflux for 5 hours and then allowed to cool to room temperature overnight. The reaction solution was concentrated in vacuo to provide the title compound (18.0 g, 100%): +APCI MS (M+H) 354.6; $^1$H NMR (400 MHz, CDCl$_3$) δ ppm 7.49 (s, 1H), 7.28-7.40 (m, 5H), 6.59 (d, J=10.16 Hz, 1H), 6.01 (d, J=9.97 Hz, 1H), 5.13 (s, 2H), 3.52-3.66 (m, 2H), 3.39-3.52 (m, 2H), 3.07 (s, 6H), 2.74 (s, 2H), 1.58-1.73 (m, 2H), 1.41-1.58 (m, 2H).

Step 2. Benzyl 1-tert-butyl-1,4-dihydrospiro[indazole-5, 4'-piperidine]-1'-carboxylate, shown below, was prepared as follows.

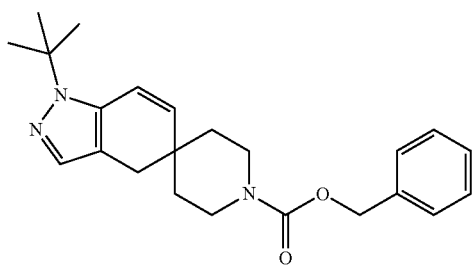 [SMILES: CC(C)(C)n1ncc2c1C=CC1(CCN(C(=O)OCc3ccccc3)CC1)C2]

Benzyl 10-((dimethylamino)methylene)-9-oxo-3-azaspiro[5.5]undec-7-ene-3-carboxylate (59.2 g, 167 mmol) was dissolved in 835 mL of ethanol. To the reaction solution was added acetic acid (20 mL, 345 mmol) and tert-butyl-hydrazine hydrochloride (29.1 g, 234 mmol). The reaction was heated to reflux for 1 hour. The reaction solution was cooled to room temperature and then concentrated in vacuo to give an orange oil which was purified by flash chromatography using 20-40% ethyl acetate in heptane as eluent to afford the title compound as a pale yellow solid (50 g, 79%): +ESI MS (M+H) 380.5; $^1$H NMR (400 MHz, CDCl$_3$) δ ppm 7.26-7.40 (m, 5H) 7.17 (s, 1H) 6.66 (d, J=9.95 Hz, 1H) 5.77 (d, J=10.15 Hz, 1H) 5.12 (s, 2H) 3.38-3.64 (m, 4H) 2.58 (s, 2H) 1.60 (s, 12H) 1.50 (br. s., 1H).

Step 3. Benzyl 6-bromo-1-tert-butyl-7-hydroxy-1,4,6,7-tetrahydrospiro[indazole-5,4'-piperidine]-1'-carboxylate, shown below, was prepared as follows.

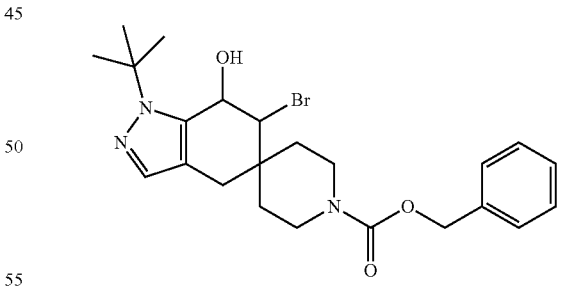

Benzyl 1-tert-butyl-1,4-dihydrospiro[indazole-5,4'-piperidine]-1'-carboxylate (50 g, 132 mmol) was dissolved in 1 L of tetrahydrofuran. To the reaction was added N-bromo-succinimide (24.6 g, 138 mmol) and 250 mL of water. The reaction was stirred for 1 hour at room temperature. The reaction was partitioned between ethyl acetate and water. The phases were separated and the organic phase was washed an additional 2 times with water and once with saturated, aqueous sodium chloride. The organic phase was dried over magnesium sulfate, concentrated in vacuo, and crystallized from ether to afford the title compound as a cream-colored solid (60.7 g, 97%): +ESI MS (M+H) 476.5; $^1$H NMR (400 MHz, CDCl$_3$) δ ppm 7.28-7.36 (m, 5H), 7.27 (s, 1H), 5.23 (t, J=4.68 Hz, 1H), 5.12 (s, 2H), 4.24 (d, J=4.49 Hz, 1H), 3.87 (br. s., 2H), 3.12 (br. s., 2H), 2.79 (d, J=16.00 Hz, 2H), 2.59 (d, J=15.80 Hz, 2H), 1.95 (br. s., 1H), 1.66 (s, 11H), 1.58 (br. s., 1H).

Step 4. Benzyl 6-bromo-1-tert-butyl-7-oxo-1,4,6,7-tetrahydrospiro[indazole-5,4'-piperidine]-1'-carboxylate, shown below, was prepared as follows.

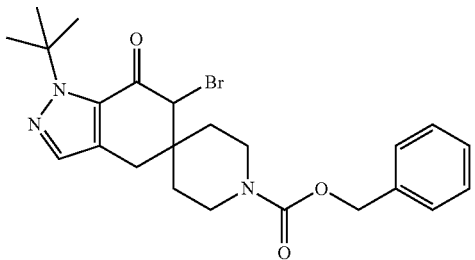 [SMILES: CC(C)(C)n1ncc2c1C(=O)C(Br)C1(CCN(C(=O)OCc3ccccc3)CC1)C2]

Benzyl 6-bromo-1-tert-butyl-7-hydroxy-1,4,6,7-tetrahydrospiro[indazole-5,4'-piperidine]-1'-carboxylate (57.9 g, 122 mmol) was dissolved in 1 L acetone and then cooled to 0° C. in an ice bath. To the solution was added 122 mL of Jones Reagent (Fillion, E. *Tetrahedron Letters* 2004, 46, 1091-1094). The ice bath was removed and the reaction was allowed to warm to room temperature where it was stirred for 45 minutes. Saturated, aqueous sodium bicarbonate was added until no further gas evolution was noted and pH reached 7. The resulting mixture was filtered through a pad of Celite® rinsing with ethyl acetate. The filtrate layers were separated and the aqueous layer was back extracted with ethyl acetate. The organic extracts were combined, washed twice with water, once with saturated aqueous sodium chloride, dried over magnesium sulfate and concentrated in vacuo. The residue was crystallized from ethyl acetate/heptane to afford the title compound (50.4 g, 87%): +ESI MS (M+H) 474.5; $^1$H NMR (400 MHz, CDCl$_3$) δ ppm 7.32 (d, J=9.38 Hz, 6H), 5.11 (s, 2H), 4.24 (s, 1H), 3.58-3.84 (m, 2H), 3.16-3.41 (m, 2H), 2.67-2.91 (m, 2H), 1.80 (br. s., 1H), 1.61-1.76 (m, 11H), 1.52-1.61 (m, 1H).

Step 5. Benzyl 1-tert-butyl-7-oxo-1,4,6,7-tetrahydrospiro[indazole-5,4'-piperidine]-1'-carboxylate, shown below, was prepared as follows.

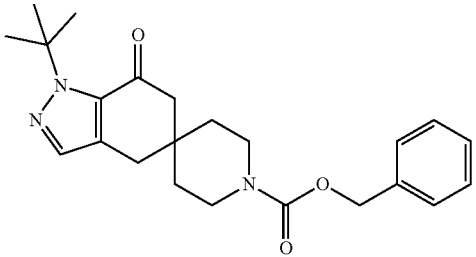 [SMILES: CC(C)(C)n1ncc2c1C(=O)CC1(CCN(C(=O)OCc3ccccc3)CC1)C2]

Benzyl 6-bromo-1-tert-butyl-7-hydroxy-1,4,6,7-tetrahydrospiro[indazole-5,4'-piperidine]-1'-carboxylate (50.4 g, 106 mmol) was dissolved in 600 mL of tetrahydrofuran, to this was added saturated, aqueous ammonium chloride (600 mL) and zinc powder (20.8 g, 319 mmol). The reaction was stirred for 30 minutes at room temperature. The reaction was filtered through Celite®, the phases were separated and the organic phase was washed with water and saturated, aqueous sodium chloride, dried over magnesium sulfate and concentrated in vacuo to give a foam. The foam was triturated once in ethyl acetate/heptane and once in ether and filtered to afford the title compound as a white solid (40.4 g, 96%): +ESI MS (M+H) 396.5; $^1$H NMR (400 MHz, CDCl$_3$) δ ppm 7.24-7.38 (m, 6H), 5.11 (s, 2H), 3.36-3.61 (m, 4H), 2.74 (s, 2H), 2.54 (s, 2H), 1.64 (s, 9H), 1.51 (br. s., 4H).

Step 6. 1-tert-butyl-4,6-dihydrospiro[indazole-5,4'-piperidin]-7(1H)-one, shown below, was prepared as follows.

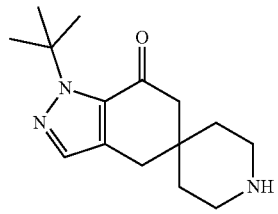 [SMILES: CC(C)(C)n1ncc2c1C(=O)CC1(CCNCC1)C2]

Benzyl 1-tert-butyl-7-oxo-1,4,6,7-tetrahydrospiro[indazole-5,4'-piperidine]-1'-carboxylate (46.6 g, 118 mmol) was dissolved in 730 mL ethanol and the solution was added to 10% palladium on carbon (9.4 g). To this was added 1-methyl-1,4-cyclohexadiene (90 mL, 769 mmol). The reaction was stirred at reflux for 2 hours. The reaction was cooled to room temperature and filtered through Celite®. The filtrate was concentrated in vacuo to give a gray solid. The solid was dissolved in 150 mL ethyl acetate, to this was added 35 mL 4 M hydrochloric acid in dioxane. A precipitate formed and was collected by filtration to afford the title compound as a white solid (34 g, 97%): +ESI MS (M+H) 262.5; $^1$H NMR (400 MHz, CD$_3$OD) δ ppm 7.34 (s, 1H) 3.12-3.25 (m, 4H) 2.90 (s, 2H) 2.66 (s, 2H) 1.67-1.85 (m, 4H) 1.62 (s, 9H).

Intermediate 11

1-(Oxetan-3-yl)-4,6-dihydrospiro[indazole-5,4'-piperidin]-7(1H)-one, shown below, was prepared as follows.

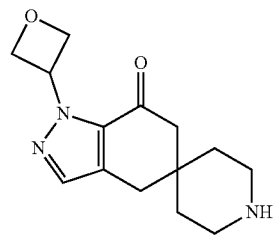 [SMILES: O=C1CC2(CCNCC2)Cc2cnn(C3COC3)c21]

Step 1. tert-Butyl 1-(2-ethoxy-2-oxoethyl)-1,4-dihydrospiro[indazole-5,4'-piperidine]-1'-carboxylate, shown below, was prepared as follows.

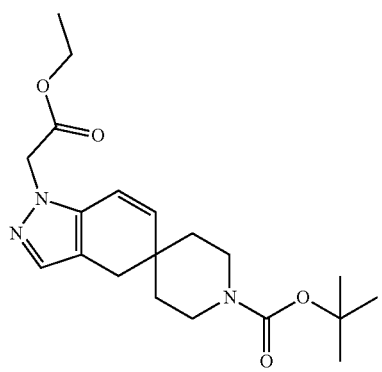 [SMILES: CCOC(=O)Cn1ncc2c1C=CC1(CCN(C(=O)OC(C)(C)C)CC1)C2]

Ethylhydrazinoacetate hydrochloride (0.92 g, 5.95 mmol) was added to a solution of benzyl 10-((dimethylamino)methylene)-9-oxo-3-azaspiro[5.5]undec-7-ene-3-carboxylate (1.25 g, 3.90 mmol), described in the preparation of Intermediate 10, in ethanol (30 mL). Stir the mixture at reflux for 1 hour. An aliquot indicated the reaction was complete by ¹HNMR. The reaction mixture was cooled to room temperature and concentrated under high vacuum to a brown oil. The oil was triturated with diethyl ether (50 mL). The precipitate was filtered and the filtrate concentrated and dried under high vacuum to yield the title compound (1.50 g, 100%) as a brown oil. +APCI MS (M+H) 376.2; ¹H NMR (400 MHz, CDCl₃) δ ppm 1.21-1.26 (m, 3H), 1.43 (s, 9H), 1.45-1.52 (m, 2H), 1.54-1.64 (m, 2H), 2.62 (s, 2H), 3.33-3.49 (m, 4H), 4.15-4.22 (m, 2H), 4.82 (s, 2H), 5.87 (d, J=9.97 Hz, 1H), 6.26 (d, J=9.97 Hz, 1H), 7.24 (s, 1H).

Step 2. Diethyl 2-(1'-(tert-butoxycarbonyl)spiro[indazole-5,4'-piperidine]-1(4H)-yl)malonate, shown below, was prepared as follows.

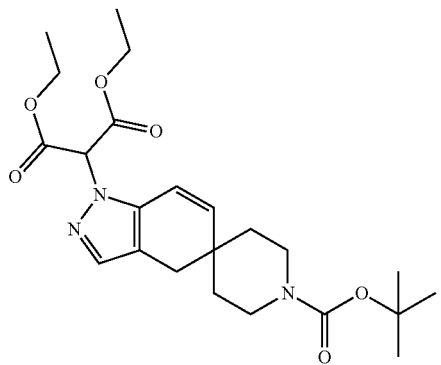 [SMILES: CCOC(=O)C(C(=O)OCC)n1ncc2c1C=CC1(CCN(C(=O)OC(C)(C)C)CC1)C2]

tert-Butyl 1-(2-ethoxy-2-oxoethyl)-1,4-dihydrospiro[indazole-5,4'-piperidine]-1'-carboxylate (1.45 g 3.86 mmol) in toluene (5 mL) was added to a suspension of sodium hydride (0.148 g, 60% dispersion in mineral oil) in diethyl carbonate (30 mL), dropwise at 80° C. over 30 minutes. The reaction was stirred at reflux for 1.5 hours. ¹H NMR indicated that starting material was consumed and that the desired product had formed. The reaction mixture was cooled to room temperature. Methanol (1 mL) was added and the solution was stirred at room temperature for 5 minutes. Water (5 mL) was added. The solution was acidified to pH~3 with 2 N aqueous, hydrochloric acid (3 mL) then was extracted with dichloromethane (3×15 mL). The combined organics were dried over magnesium sulfate, filtered, concentrated, and dried under high vacuum to yield a brown gum (1.59 g, 92%). The crude material was triturated with 1:1 diethyl ether:heptanes (50 mL). The precipitate was filtered. The filtrate was concentrated and dried under high vacuum to yield the title compound (1.25 g, 72%). +APCI MS (M+H) 348.1; ¹H NMR (400 MHz, CDCl₃) δ ppm 1.13-1.32 (m, 6H), 1.40-1.46 (m, 9H), 1.46-1.54 (m, 2H), 1.59 (d, J=13.68 Hz, 3H), 2.62 (s, 2H), 3.31-3.51 (m, 4H), 4.27 (q, J=7.23 Hz, 4H), 5.85 (d, J=9.97 Hz, 1H), 6.34 (d, J=9.97 Hz, 1H), 7.24 (s, 1H).

Step 3. tert-Butyl 1-(1,3-dihydroxypropan-2-yl)-1,4-dihydrospiro[indazole-5,4'-piperidine]-1'-carboxylate, shown below, was prepared as follows.

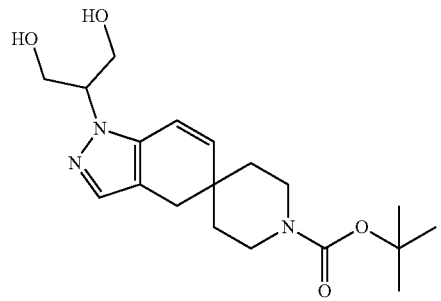 [SMILES: CC(C)(C)OC(=O)N1CCC2(C=Cc3c(cnn3C(CO)CO)C2)CC1]

Tetrahydrofuran (40 mL) was added to lithium aluminum hydride (900 mg) in a 3-neck, 125 mL roundbottom flask equipped with a nitrogen inlet and thermometer. The solution was cooled to −2° C. Diethyl 2-(1'-(tert-butoxycarbonyl)spiro[indazole-5,4'-piperidine]-1(4H)-yl)malonate (1 g) in tetrahydrofuran (5 mL) was added dropwise over 5 minutes. The temperature was never greater than −0.2° C. during the addition. The reaction was stirred at 0° C. for 3 hours then the reaction was then quenched through the sequential addition of water (1.0 mL), 15% aqueous sodium hydroxide (1.0 mL), and water (3 mL). The internal temperature was never greater than 3.2° C. during the addition. The reaction was then allowed to warm to room temperature over 15 minutes. The reaction mixture was filtered through Celite® and washed with diethyl ether (3×20 mL). The combined organics were washed with brine (5 mL) dried over sodium sulfate, filtered, concentrated, and dried under high vacuum to yield a pale yellow glass (548 mg, 67%). This material was chromatographed on 25 g of silica eluting with 2% to 8% methanol in dichloromethane with 0.1% ammonium hydroxide over 30 minutes to yield the title compound (133 mg, 16%). +APCI MS (M+H) 364.2; ¹H NMR (400 MHz, CDCl₃) δ ppm 1.45 (s, 9H), 1.51 (br. s., 2H), 1.60 (br. s., 4H), 2.62 (s, 2H), 3.32-3.53 (m, 4H), 4.05 (br. s., 4H), 4.26 (t, J=4.89 Hz, 1H), 5.89 (s, 1H), 6.40 (d, J=9.77 Hz, 1H), 7.23-7.25 (m, 1H).

Step 4. tert-Butyl 1-(oxetan-3-yl)-1,4-dihydrospiro[indazole-5,4'-piperidine]-1'-carboxylate, shown below, was prepared as follows.

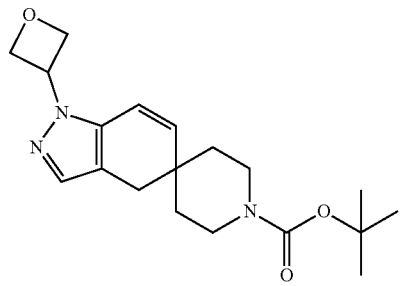 [SMILES: CC(C)(C)OC(=O)N1CCC2(C=Cc3c(cnn3C3COC3)C2)CC1]

2.5 M n-butyl lithium in hexanes (0.33 ml165 uL) was added to a solution of tert-Butyl 1-(1,3-dihydroxypropan-2-yl)-1,4-dihydrospiro[indazole-5,4'-piperidine]-1'-carboxylate (150 mg, 0.41 mmol) in tetrahydrofuran (8 mL) at −6.2° C. The temperature was never greater than −3.7° C. during the addition. The solution was stirred at −8° C. for 30 minutes. A solution of p-toluenesulfonyl chloride (79 mg) in tetrahydrofuran (2 mL) was added to the reaction mixture at −5° C. The temperature was never greater than −2° C. during the addition. The reaction was stirred at −5° C. for 1 hour then the reaction mixture was cooled to −6° C. and 2.5 M n-butyl lithium in hexanes (0.33 mL, 165 uL) was added over 2 minutes. The temperature was never greater than −3.5° C. during the addition. The cooling bath was removed and the reaction was stirred at an internal temperature of 60° C. for 16 hours. The reaction mixture was cooled to room temperature and ethyl acetate (20 mL) was added. The reaction solution was washed with water (35 mL) and the aqueous layer was extracted with ethyl acetate (15 mL). The combined organics were washed with brine (5 mL) dried over magnesium sulfate, filtered, concentrated, and dried under high vacuum to yield a yellow solid. The solid was purified by chromatography on 8 g silica eluting with 25% to 75% ethyl acetate in heptanes over 36 minutes to yield the title compound (58 mg, 40%). +ESI MS (M+H); $^1$H NMR (400 MHz, CDCl$_3$) δ ppm 1.45 (s, 9H), 1.49 (d, J=3.71 Hz, 1H), 1.55 (s, 4H), 1.59 (br. s., 1H), 2.61 (s, 2H), 3.32-3.50 (m, 4H), 5.00 (m, J=7.22, 7.22 Hz, 2H), 5.13 (t, J=6.44 Hz, 2H), 5.36-5.46 (m, 1H), 5.88 (d, J=9.95 Hz, 1H), 6.43 (d, J=9.95 Hz, 1H), 7.33 (s, 1H).

Step 5. tert-Butyl 6-bromo-7-methoxy-1-(oxetan-3-yl)-1,4,6,7-tetrahydrospiro[indazole-5,4'-piperidine]-1'-carboxylate, shown below, was prepared as follows.

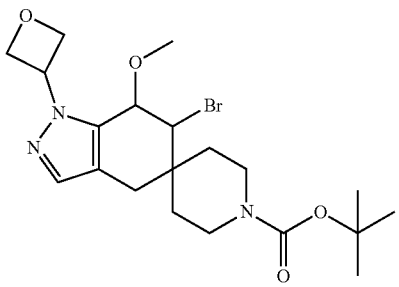 [SMILES: COC1c2c(cnn2C2COC2)CC2(CCN(C(=O)OC(C)(C)C)CC2)C1Br]

N-Bromosuccinimide (30 mg, 0.17 mmol) was added to tert-butyl 1-(oxetan-3-yl)-1,4-dihydrospiro[indazole-5,4'-piperidine]-t-carboxylate (56 mg, 0.17 mmol) in methanol (1.0 mL) at room temperature. The reaction was stirred at room temperature for 2 hours then N-bromosuccinimide (4.5 mg) was added and the reaction mixture was stirred at room temperature for 1 hour. The reaction mixture was concentrated under a stream of nitrogen to a residue. Ethyl acetate (15 mL) was added and the reaction solution was washed with 10% citric acid (3 mL), 1N sodium hydroxide (3 mL), and brine (3 mL). The organic layer was concentrated and dried under high vacuum to yield the title compound (74 mg, 100%) as a colorless solid. +APCI MS (M+H) 458.2; $^1$H NMR (400 MHz, CDCl$_3$) δ ppm 1.44 (s, 9H), 1.69 (br. s., 4H), 2.51 (d, J=15.83 Hz, 1H), 2.67 (d, J=15.83 Hz, 1H), 3.06-3.31 (m, 3H), 3.54 (s, 3H), 3.62-3.72 (m, 1H), 4.39 (s, 1H), 4.66 (s, 1H), 4.87-4.93 (m, 1H), 4.97 (t, J=6.84 Hz, 1H), 4.99-5.04 (m, 1H), 5.30 (s, 1H), 5.34-5.40 (m, 1H), 7.43 (s, 1H).

Step 6. tert-Butyl 1-(oxetan-3-yl)-7-oxo-1,4,6,7-tetrahydrospiro[indazole-5,4'-piperidine]-1'-carboxylate, shown below, was prepared as follows.

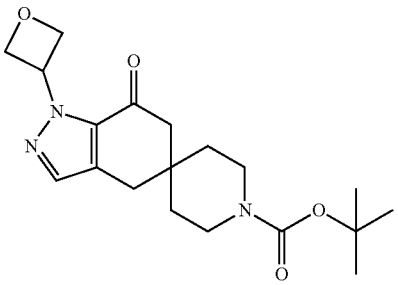 [SMILES: CC(C)(C)OC(=O)N1CCC2(CC1)CC(=O)c1c(cnn1C1COC1)C2]

1 M potassium tert-butoxide in tetrahydrofuran (0.320 mL) was added to a solution of tert-butyl 6-bromo-7-methoxy-1-(oxetan-3-yl)-1,4,6,7-tetrahydrospiro[indazole-5,4'-piperidine]-1'-carboxylate 72 mg, 0.16 mmol) in tetrahydrofuran (1.0 mL) at room temperature. The colorless solution turned yellow upon addition. The solution was stirred at room temperature for 16 hours. 1 N aqueous, hydrogen chloride (0.475 mL, 3 eq.) was added and the solution was stirred at room temperature for 1 hour. The tetrahydrofuran was concentrated under a stream of nitrogen. The aqueous phase was extracted with ethyl acetate (3×5 mL). The combined organics were washed with brine (3 mL) then the organic layer was concentrated and dried under high vacuum to give the title compound as a pale yellow solid (54 mg, 96%). −APCI MS (M−H) 360.2; $^1$H NMR (400 MHz, CD$_3$OD) δ ppm 1.38-1.45 (m, 9H), 1.46-1.56 (m, 4H), 2.57 (s, 2H), 2.82 (s, 2H), 3.33-3.53 (m, 4H), 4.94-5.06 (m, 4H), 6.08-6.21 (m, 1H), 7.53 (s, 1H).

Step 7. 1-(oxetan-3-yl)-4,6-dihydrospiro[indazole-5,4'-piperidin]-7(1H)-one, shown below, was prepared as follows.

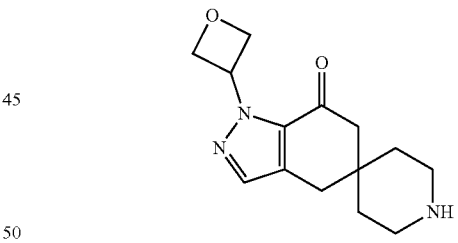

Trifluoroacetic acid (0.2 mL) was added to a solution of tert-butyl 1-(oxetan-3-yl)-7-oxo-1,4,6,7-tetrahydrospiro[indazole-5,4'-piperidine]-1'-carboxylate (50 mg, 0.14 mmol) in dichloromethane (2 mL) at 0° C. The cooling bath was removed and the reaction was stirred at room temperature for 1.5 hours. The reaction mixture was concentrated to a residue under a stream of nitrogen and dried under high vacuum for 20 minutes. The residue was triturated with diethyl ether (5 mL). The solvent was decanted and the resulting precipitate was dried under high vacuum to yield the title compound (52 mg, 100) as a pale yellow solid. +APCI MS (M+H) 262.2; $^1$H NMR (400 MHz, CD$_3$OD) δ ppm 1.65-1.86 (m, 4H), 2.63 (s, 2H), 2.89 (s, 2H), 3.14-3.27 (m, 4H), 5.02 (s, 4H), 6.07-6.21 (m, 1H), 7.53-7.60 (m, 1H).

Intermediate 12

1-Isopropyl-3-methyl-4,6-dihydrospiro[indazole-5,4'-piperidin]-7(1H)-one, shown below, was prepared as follows.

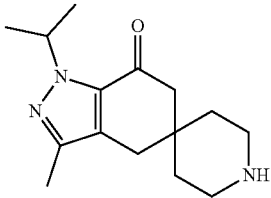 [SMILES: Cc1nn(C(C)C)c2c1CC1(CCNCC1)CC2=O]

Step 1. Benzyl 1-isopropyl-1,4-dihydrospiro[indazole-5,4'-piperidine]-1'-carboxylate, shown below, was prepared as follows.

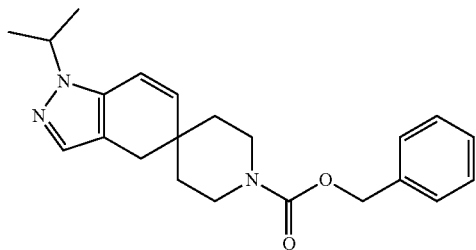 [SMILES: CC(C)n1ncc2c1C=CC1(CCN(C(=O)OCc3ccccc3)CC1)C2]

Benzyl 10-((dimethylamino)methylene)-9-oxo-3-azaspiro[5.5]undec-7-ene-3-carboxylate (6.38 g, 18 mmol), prepared as described in the preparation of Intermediate 10, was dissolved in 90 mL of ethanol. To the reaction solution was added acetic acid (2.16 g, 36 mmol) and 1-isopropylhydrazine hydrochloride (2.79 g, 25 mmol). The reaction was heated to reflux for 2 hours then the reaction solution was cooled to room temperature and concentrated in vacuo to give an orange oil which was purified by flash chromatography using 12-100% ethyl acetate in heptane as eluent to afford the title compound as a yellow gum (6.58 g, 69%): +ESI MS (M+H) 366.5; $^1$H NMR (400 MHz, CDCl$_3$) δ ppm 7.28-7.39 (m, 5H), 7.25 (s, 1H), 6.42 (d, J=9.95 Hz, 1H), 5.84 (d, J=9.95 Hz, 1H), 5.14 (s, 2H), 4.41-4.54 (m, 1H), 3.42-3.65 (m, 4H), 2.62 (s, 2H), 1.58-1.70 (m, 2H), 1.50-1.58 (m, 2H), 1.49 (d, J=6.83 Hz, 6H).

Step 2. Benzyl 3,6-dibromo-1-isopropyl-7-methoxy-1,4,6,7-tetrahydrospiro[indazole-5,4'-piperidine]-1'-carboxylate, shown below, was prepared as follows.

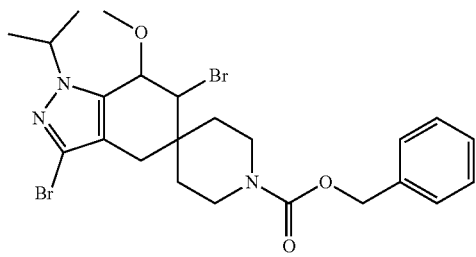 [SMILES: COC1c2c(c(Br)nn2C(C)C)CC2(CCN(C(=O)OCc3ccccc3)CC2)C1Br]

Benzyl 1-isopropyl-1,4-dihydrospiro[indazole-5,4'-piperidine]-1'-carboxylate (679 mg, 1.86 mmol) was dissolved in 15 mL methanol and treated with N-bromosuccinimide (728 mg, 4.09 mmol) and the reaction was stirred at ambient temperature for 18 hours. The methanol was removed under reduced pressure. The resultant tan foam was taken up in 50 mL ethyl acetate and washed with 0.5 M sodium hydroxide (2×50 mL) and 20 mL saturated aqueous sodium thiosulfate. The organic phase was dried over sodium sulfate, filtered and concentrated. The resultant oil was flash chromatographed (25 g silica, 10-80% ethyl acetate/heptane gradient) to yield 784 mg (76%) of the title compound as a white foam: +APCI-MS (M+H)=554.1, 556.2, 558.2: $^1$H NMR (400 MHz, CDCl$_3$) δ ppm 7.26-7.42 (m, 5H), 5.12 (s, 2H), 4.67 (d, J=1.76 Hz, 1H), 4.36 (s, 1H), 4.27 (m, 1H), 3.79 (d, J=11.90 Hz, 1H), 3.59-3.73 (m, 1H), 3.53 (s, 3H), 3.24-3.40 (m, 1H), 3.19 (ddd, J=13.61, 10.00, 3.12 Hz, 1H), 2.56 (d, J=16.19 Hz, 1H), 2.34 (d, J=16.19 Hz, 1H), 1.56-1.85 (m, 4H), 1.38-1.55 (m, 6H).

Step 3. Benzyl 3-bromo-1-isopropyl-7-oxo-1,4,6,7-tetrahydrospiro[indazole-5,4'-piperidine]-1'-carboxylate, shown below, was prepared as follows.

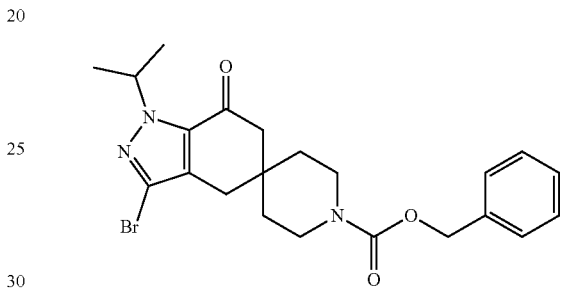

Benzyl 3,6-dibromo-1-isopropyl-7-methoxy-1,4,6,7-tetrahydrospiro[indazole-5,4'-piperidine]-1'-carboxylate (784 mg, 1.4 mmol) was dissolved in 15 mL tetrahydrofuran. Potassium t-butoxide (2.82 mL, 2 eq, 1 M tetrahydrofuran) was added and the reaction was stirred for 18 hours at ambient temperature. To the reaction was added 25 mL 2 N hydrochloric acid. The mixture was stirred for 30 minutes at ambient temperature. The mixture was diluted with 25 mL water and extracted with ethyl acetate (2×50 mL). The organic extracts were combined and dried over sodium sulfate, filtered and concentrated. The resultant oil was flash chromatographed (50 g silica, 8-66% ethyl acetate/heptane gradient) to yield 612 mg of the title compound as a white foam: +ESI MS (M+H)=462.5 $^1$H NMR (400 MHz, CDCl$_3$) δ ppm 7.25-7.38 (m, 5H), 5.24-5.42 (m, 1H), 5.12 (s, 2H), 3.49-3.66 (m, 2H), 3.46 (dd, J=7.41, 4.88 Hz, 2H), 2.63 (s, 2H), 2.52 (s, 2H), 1.48-1.65 (m, 4H), 1.44 (d, J=6.63 Hz, 6H).

Step 4. tert-Butyl 3-bromo-1-isopropyl-7-oxo-1,4,6,7-tetrahydrospiro[indazole-5,4'-piperidine]-1'-carboxylate, shown below, was prepared as follows.

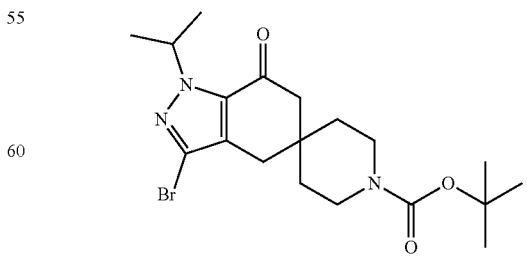

Benzyl 3-bromo-1-isopropyl-7-oxo-1,4,6,7-tetrahydrospiro[indazole-5,4'-piperidine]-1'-carboxylate (612 mg, 1.33 mmol) was dissolved in 10 mL 33% hydrobromic acid/acetic acid and the mixture was stirred for 60 minutes at ambient temperature. The solvent was evaporated and the red-orange residue taken up in 50 mL water and made basic with saturated aqueous sodium carbonate and extracted with ethyl acetate (2×50 mL). The organic phase was concentrated to 20 mL and treated with 20 mL saturated aqueous sodium bicarbonate and di-tert-butyl dicarbonate (348 mg). The biphasic mixture stirred for one hour at ambient temperature. The layers were separated and the organic phase dried over sodium sulfate, filtered and concentrated under reduced pressure. The resultant oil was flash chromatographed (10-70% ethyl acetate/heptane, 10 g silica) to yield 364 mg of the title compound. +ESI MS (M+H)=413.5; $^1$H NMR (400 MHz, CDCl$_3$) δ ppm 5.24-5.43 (m, 1H), 3.41-3.56 (m, 2H), 3.28-3.41 (m, 2H), 2.63 (s, 2H), 2.51 (s, 2H), 1.47-1.56 (m, 4H), 1.40-1.49 (m, 15H).

Step 5. tert-Butyl 1-isopropyl-3-methyl-7-oxo-1,4,6,7-tetrahydrospiro[indazole-5,4'-piperidine]-1'-carboxylate, shown below, was prepared as follows.

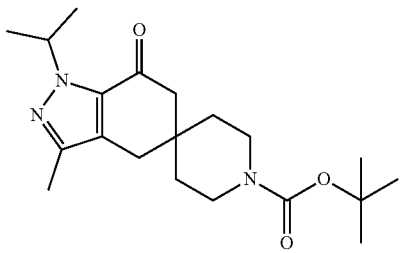 [SMILES: Cc1nn(C(C)C)c2c1CC1(CCN(C(=O)OC(C)(C)C)CC1)CC2=O]

tert-Butyl 3-bromo-1-isopropyl-7-oxo-1,4,6,7-tetrahydrospiro[indazole-5,4'-piperidine]-1'-carboxylate (440 mg, 1.03 mmol), palladium tetrakis triphenylphosphine (119 mg, 0.103 mmol), potassium carbonate (146 mg, 1.03 mmol), and water (94 mg, 5.16 mmol) were combined in dimethylformamide (2 mL) and degassed with nitrogen for 2 minutes. The reaction vial was sealed and heated in a microwave reactor for 30 minutes at 100° C. The vial was removed from the microwave reactor and then heated to 100° C. in a conventional heating block for 4 days. The reaction was concentrated in vacuo and then partitioned between water (5 mL) and ethyl acetate (5 mL). The phases were separated and the organic layer was concentrated and then chromatographed on a 40 g column eluting with 20-40% ethyl acetate in heptane gradient to give 268 mg (72%) of the title compound. +ESI MS (M+H)=362.5; $^1$H NMR (400 MHz, CDCl$_3$) δ ppm 5.20-5.53 (m, 1H), 3.32-3.54 (m, 4H), 2.62 (s, 2H), 2.50 (s, 2H), 2.23 (s, 3H), 1.53 (t, J=5.76 Hz, 4H), 1.46 (s, 9H), 1.44 (d, J=6.64 Hz, 6H).

Step 6. 1-Isopropyl-3-methyl-4,6-dihydrospiro[indazole-5,4'-piperidin]-7(1H)-one, shown below, was prepared as follows.

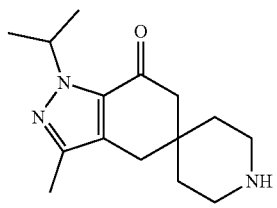 [SMILES: Cc1nn(C(C)C)c2c1CC1(CCNCC1)CC2=O]

tert-Butyl 1-isopropyl-3-methyl-7-oxo-1,4,6,7-tetrahydrospiro[indazole-5,4'-piperidine]-1'-carboxylate (375 mg, 1.04 mmol) was dissolved in 3 mL diethyl ether and treated with 4 M hydrogen chloride in dioxane (1 mL). The solution was stirred for one hour and then concentrated in vacuo to provide 300 mg of the title compound as a white foam: $^1$H NMR (400 MHz, DMSO-d$_6$) δ ppm 5.10-5.35 (m, 1H), 4.34 (br. s., 4H), 2.70 (s, 2H), 2.56 (s, 2H), 2.17 (s, 3H), 1.66 (br. s., 4H), 1.34 (d, J=6.64 Hz, 6H).

Intermediate 13

1-isopropyl-7-oxo-1,4,6,7-tetrahydrospiro[indazole-5,4'-piperidine]-3-carbonitrile, shown below, was prepared as follows.

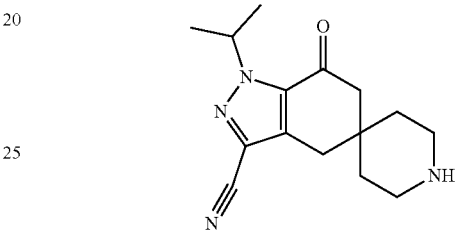

Step 1. tert-Butyl 3-cyano-1-isopropyl-7-oxo-1,4,6,7-tetrahydrospiro[indazole-5,4'-piperidine]-1'-carboxylate, shown below, was prepared as follows.

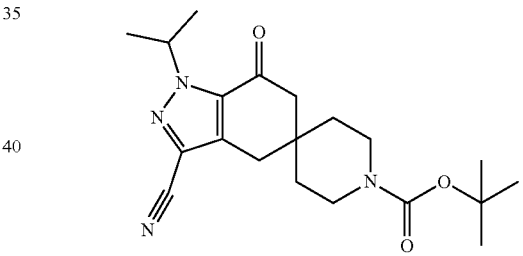

In a schlenk tube flushed with nitrogen was added tert-butyl 3-bromo-1-isopropyl-7-oxo-1,4,6,7-tetrahydrospiro [indazole-5,4'-piperidine]-1'-carboxylate (250 mg, 0.59 mmol), prepared as described in the preparation of Intermediate 12, tris(dibenzylideneacetone)dipalladium(0)-chloroform adduct (23.8 mg, 0.02 mmol), zinc dust (9.6 mg, 0.15 mmol), zinc cyanide (75.7 mg, 0.65 mmol) and 1,1'-bis (diphenylphosphino)ferrocene (26.1 mg, 0.05 mmol). Anhydrous dimethylacetamide (3.5 mL) was added and the flask was flushed with nitrogen, then capped with a Teflon® screw top. The reaction was stirred at 120° C. for 16 hours. The reaction was cooled and then filtered through a pad of Celite® washing with ethyl acetate. The filtrate was washed with water and the aqueous phase was back extracted with ethyl acetate. The combined organic phases were washed with saturated aqueous sodium chloride, dried over magnesium sulfate and concentrated in vacuo. The residue was purified by flash chromatography using 5-30% ethyl acetate in heptane gradient to give 204 mg of the title compound as a solid (93%): +ESI MS (M-Boc+H) 273.5; $^1$H NMR (400

MHz, CD₃OD) δ ppm 5.44 (m, 1H), 3.44 (m, 4H), 2.89 (s, 2H), 2.64 (s, 2H), 1.53 (m, 4H), 1.46-1.43 (m, 15H).

Step 2. 1-Isopropyl-7-oxo-1,4,6,7-tetrahydrospiro[indazole-5,4'-piperidine]-3-carbonitrile

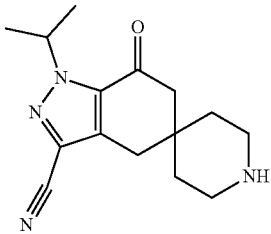 [SMILES: CC(C)n1nc(C#N)c2c1C(=O)CC1(CCNCC1)C2]

tert-Butyl 3-cyano-1-isopropyl-7-oxo-1,4,6,7-tetrahydrospiro[indazole-5,4'-piperidine]-1'-carboxylate (70 mg, 0.19 mmol) was dissolved in dichloromethane (3 mL) and trifluoroacetic acid (0.2 mL) and stirred at ambient temperature for 90 minutes. The solvent was concentrated in vacuo and the residue was co-distilled with toluene followed by ethyl acetate to give 149 mg (100%) of the title compound as a yellow solid: +ESI MS (M+H) 273.5.

Intermediate 14

1-isopropyl-6-methyl-4,6-dihydrospiro[indazole-5,4'-piperidin]-7(1H)-one, shown below, was prepared as follows.

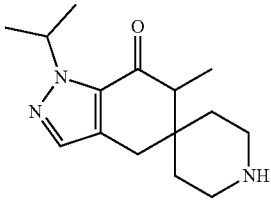 [SMILES: CC(C)n1ncc2c1C(=O)C(C)C1(CCNCC1)C2]

Step 1. Benzyl 6-bromo-7-hydroxy-1-isopropyl-1,4,6,7-tetrahydrospiro[indazole-5,4'-piperidine]-1'-carboxylate, shown below, was prepared as follows.

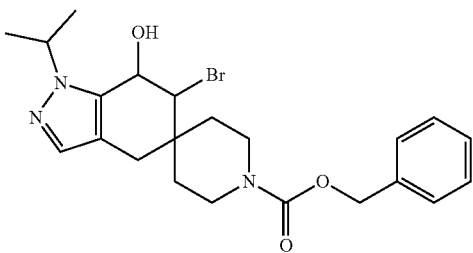 [SMILES: CC(C)n1ncc2c1C(O)C(Br)C1(CCN(C(=O)OCc3ccccc3)CC1)C2]

Benzyl 1-isopropyl-1,4-dihydrospiro[indazole-5,4'-piperidine]-1'-carboxylate (4.20 g, 11 mmol), prepared as described in the preparation of Intermediate 12, was dissolved in 130 mL of tetrahydrofuran. To the reaction was added N-bromosuccinimide (2.49 g, 14 mmol) and 30 mL of water. The reaction was stirred for 1 hour at room temperature. The reaction was partitioned between ethyl acetate and saturated, aqueous sodium chloride. The organic phase was separated then washed an additional time with saturated aqueous sodium chloride. The organic phase was dried over sodium sulfate and concentrated in vacuo to afford the title compound as an off-white foam (5.31 g, 100%): +ESI MS (M+H) 463.8.

Step 2. Benzyl 6-bromo-1-isopropyl-7-oxo-1,4,6,7-tetrahydrospiro[indazole-5,4'-piperidine]-1'-carboxylate, shown below, was prepared as follows.

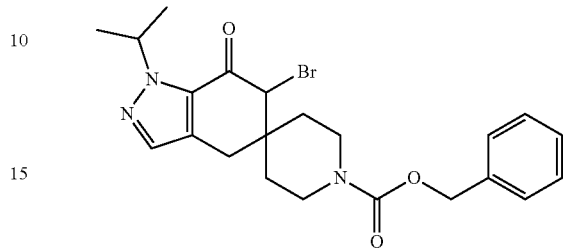

Benzyl 6-bromo-7-hydroxy-1-isopropyl-1,4,6,7-tetrahydrospiro[indazole-5,4'-piperidine]-1'-carboxylate (5.30 g, 11 mmol) was dissolved in 53 mL acetone and then cooled to 0° C. in an ice bath. To the solution was added 83 mL of Jones Reagent (Fillion, E. *Tetrahedron Letters* 2004, 46, 1091-1094). The ice bath was removed and the reaction was allowed to warm to room temperature where it was stirred for 45 minutes. The reaction was cooled to 0° C. in an ice bath and then saturated, aqueous sodium bicarbonate was added until no further gas evolution was noted. The resulting mixture was filtered through a pad of Celite® rinsing with ethyl acetate. The filtrate layers were separated and the aqueous layer was back extracted with ethyl acetate. The organic extracts were combined, washed twice with water, once with saturated, aqueous sodium chloride, dried over sodium sulfate and concentrated in vacuo to afford the title compound (5.27 g, 100%): +ESI MS (M+H) 460.4.

Step 3. Benzyl 1-isopropyl-7-oxo-1,4,6,7-tetrahydrospiro[indazole-5,4'-piperidine]-1'-carboxylate, shown below, was prepared as follows.

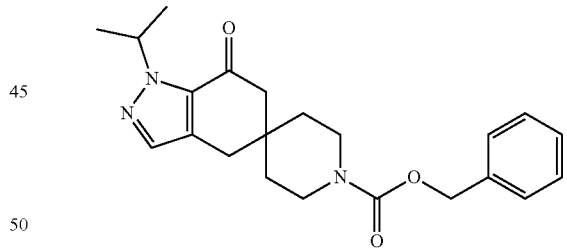

Benzyl 6-bromo-1-isopropyl-7-oxo-1,4,6,7-tetrahydrospiro[indazole-5,4'-piperidine]-1'-carboxylate (5.63 g, 12 mmol) was dissolved in 55 mL of acetic acid, to this was added zinc powder (2.40 g, 37 mmol). The reaction was stirred for 35 minutes at room temperature. The reaction was concentrated in vacuo and then partitioned between saturated, aqueous sodium bicarbonate and ethyl acetate. The phases were separated and the aqueous phase was extracted with ethyl acetate. The organic extracts were combined, washed with water, saturated, aqueous sodium chloride, dried over sodium sulfate and concentrated in vacuo to give an oil. The oil was purified by flash chromatography using 12-100% ethyl acetate in heptane as eluent to afford the title compound as an oil (2.25 g, 48%): +ESI MS(M+H) 382.4; ¹H NMR (400 MHz, CDCl₃) δ ppm 7.28-7.40 (m, 6H), 5.32-5.45 (m, 1H), 5.13 (s, 2H), 3.41-3.61 (m, 4H), 2.76 (s, 2H), 2.54 (s, 2H), 1.50-1.62 (m, 4H), 1.47 (d, J=6.63 Hz, 6H).

Step 4. Benzyl 1-isopropyl-6-methyl-7-oxo-1,4,6,7-tetrahydrospiro[indazole-5,4'-piperidine]-1'-carboxylate, shown below, was prepared as follows.

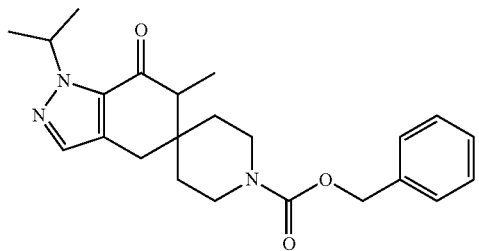 [SMILES: CC(C)n1ncc2c1C(=O)C(C)C1(CCN(C(=O)OCc3ccccc3)CC1)C2]

Benzyl 1-isopropyl-7-oxo-1,4,6,7-tetrahydrospiro[indazole-5,4'-piperidine]-1'-carboxylate (397 mg, 1.04 mmol) in tetrahydrofuran (8 mL) was cooled to −70° C. To this was added lithium bis(trimethylsilyl)amide (1.56 mL, 1.56 mmol) as a 1.0 M solution in tetradhydrofuran over a ten minute period. The resulting yellow solution was stirred for thirty minutes at −70° C. 1,3-Dimethyl-3,4,5,6-tetrahydro-2(1H)-pyrimidone (1.6 mL) was added to the reaction, stirring was continued at −70° C. for ten minutes. To the reaction was added iodomethane (746 mg, 5.2 mmol). The reaction was allowed to warm to room temperature where it was stirred for 18 hours. To the reaction was added saturated, aqueous sodium bicarbonate (2 mL), the mixture was then partitioned between water (20 mL) and ethyl acetate (150 mL). The layers were separated and the aqueous layer was extracted with ethyl acetate (150 mL). The organic layers were combined, dried over magnesium sulfate, filtered and then concentrated to give a clear oil. The oil was purified by silica gel chromatography using 10-40% ethyl acetate in heptane as eluent to afford the title compound as a white solid (351 mg, 85%): +ESI MS (M+H) 396.2; $^1$H NMR (400 MHz, DMSO-$d_6$) δ ppm 7.44 (s, 1H), 7.35 (s, 5H), 5.17-5.34 (m, 1H), 5.06 (s, 2H), 3.52-3.72 (m, 4H), 2.79 (s, 2H), 2.42-2.48 (m, 1H), 1.38-1.49 (m, 4H), 1.35 (t, J=6.74 Hz, 6H), 1.04 (d, J=7.04 Hz, 3H).

Step 5. 1-Isopropyl-6-methyl-4,6-dihydrospiro[indazole-5,4'-piperidin]-7(1H)-one, shown below, was prepared as follows.

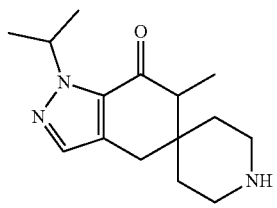 [SMILES: CC(C)n1ncc2c1C(=O)C(C)C1(CCNCC1)C2]

The title compound was prepared from benzyl 1-isopropyl-6-methyl-7-oxo-1,4,6,7-tetrahydrospiro[indazole-5,4'-piperidine]-1'-carboxylate in an analogous fashion to Intermediate 10, Step 6.

Intermediate 15

1-isopropyl-6,6-dimethyl-4,6-dihydrospiro[indazole-5,4'-piperidin]-7(1H)-one, shown below, was prepared as follows.

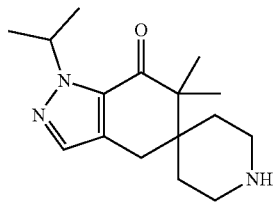

Step 1. Benzyl 1-isopropyl-6,6-dimethyl-7-oxo-1,4,6,7-tetrahydrospiro[indazole-5,4'-piperidine]-1'-carboxylate, shown below, was prepared as follows.

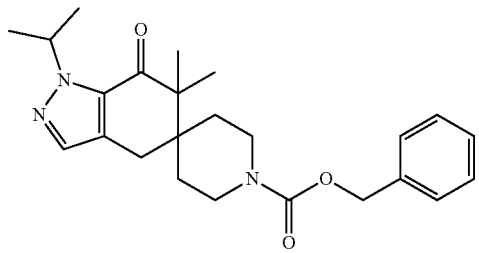 [SMILES: CC(C)n1ncc2c1C(=O)C(C)(C)C1(CCN(C(=O)OCc3ccccc3)CC1)C2]

A solution of benzyl 1-isopropyl-6-methyl-7-oxo-1,4,6,7-tetrahydrospiro[indazole-5,4'-piperidine]-1'-carboxylate (84 mg, 0.21 mmol), described in the preparation of Intermediate 14, in 1 mL tetrahydrofuran was cooled to −70° C. and then treated with lithium bis(trimethylsilyl)amide (0.318 mL, 0.318 mmol) as a 1.0 M solution in tetrahydrofuran over ten minutes. Then 1,3-Dimethyl-3,4,5,6-tetrahydro-2(1H)-pyrimidone (0.2 mL) was added to the reaction. Stirring continued for ten minutes at −70° C., then iodomethane (152 mg, 1.06 mmol) was added to the reaction. The mixture was allowed to warm to room temperature where it was held for four hours. To the reaction was added saturated, aqueous ammonium chloride (1 mL), the mixture was then partitioned between water (2 mL) and ethyl acetate (10 mL). The layers were separated and the aqueous layer was extracted with ethyl acetate (5 mL). The organic layers were combined, dried over magnesium sulfate, filtered and then concentrated to give a clear, yellow oil. The oil was purified by silica gel chromatography using 10-40% ethyl acetate in heptane as eluent to afford the title compound as a clear oil (58 mg, 67%): +ESI MS (M+H) 410.3; $^1$H NMR (400 MHz, CDCl$_3$) δ ppm 7.28-7.44 (m, 5H), 7.27 (s, 1H), 5.40 (m, 1H), 5.13 (s, 2H), 3.85-4.24 (m, 2H), 2.86-3.11 (m, 2H), 1.58-1.79 (m, 2H), 1.56 (s, 2H), 1.46 (d, J=6.64 Hz, 6H), 1.19-1.40 (m, 2H), 1.15 (s, 6H).

Step 2. 1-Isopropyl-6,6-dimethyl-4,6-dihydrospiro[indazole-5,4'-piperidin]-7(1H)-one, shown below, was prepared as follows.

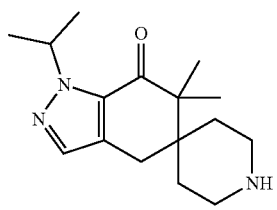 [SMILES: CC(C)n1ncc2c1C(=O)C(C)(C)C1(CCNCC1)C2]

The title compound was prepared from benzyl 1-isopropyl-6,6-dimethyl-7-oxo-1,4,6,7-tetrahydrospiro [indazole-5,4'-piperidine]-1'-carboxylate in an analogous fashion to Intermediate 10, Step 6.

Intermediate 16

3-bromo-1-tert-butyl-4,6-dihydrospiro[indazole-5,4'-piperidin]-7(1H)-one, shown below, was prepared as follows.

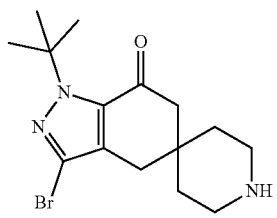 [SMILES: CC(C)(C)n1nc(Br)c2c1C(=O)CC1(CCNCC1)C2]

Step 1. tert-Butyl 1-tert-butyl-7-oxo-1,4,6,7-tetrahydrospiro[indazole-5,4'-piperidine]-1'-carboxylate, shown below, was prepared as follows.

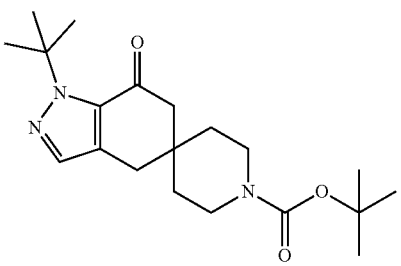 [SMILES: CC(C)(C)OC(=O)N1CCC2(CC1)CC(=O)c1c(cnn1C(C)(C)C)C2]

The hydrochloride salt of Intermediate 10 (1040 mg, 3.492 mmol), di-tert-butyl dicarbonate (800 mg, 3.67 mmol) and triethlyamine (730 mg, 7.2 mmol) were combined in dichloromethane (30 mL). The reaction solution was stirred at ambient temperature for 16 hours. To the reaction was added dichloromethane (20 mL). The reaction solution was washed with 1N aqueous hydrochloric acid (5 mL), water (5 mL), and saturated, aqueous sodium chloride (5 mL). The organic phase was dried over magnesium sulfate and concentrated to give tert-butyl 1-tert-butyl-7-oxo-1,4,6,7-tetrahydrospiro[indazole-5,4'-piperidine]-1'-carboxylate (1262 mg, 100%): −APCI MS (M−H) 360.3; $^1$H NMR (400 MHz, CDCl$_3$) δ ppm 7.30 (s, 1H), 3.29-3.56 (m, 4H), 2.77 (s, 2H), 2.56 (s, 2H), 1.67 (s, 9H), 1.48-1.56 (m, 4H), 1.46 (s, 9H).

Step 2. tert-Butyl 3-bromo-1-tert-butyl-7-oxo-1,4,6,7-tetrahydrospiro[indazole-5,4'-piperidine]-1'-carboxylate, shown below, was prepared as follows.

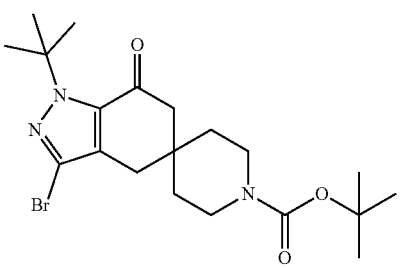 [SMILES: CC(C)(C)OC(=O)N1CCC2(CC1)CC(=O)c1c(c(Br)nn1C(C)(C)C)C2]

tert-Butyl 1-tert-butyl-7-oxo-1,4,6,7-tetrahydrospiro[indazole-5,4'-piperidine]-1'-carboxylate (1090 mg, 3.015 mmol) and sodium acetate (1050 mg, 12.80 mmol) were combined in ethanol (40 mL) and water (10 mL). To this solution was added bromine (1870 mg, 11.7 mmol). The reaction was stirred at room temperature for 4 hours. To the reaction was added ethanol (40 mL). The reaction was stirred for 16 more hours. The reaction solution was poured in water (20 mL) and extracted twice with ethyl acetate (75 mL each). The combined organic extracts were washed twice with aqueous, saturated sodium thiosulfate (25 mL each) and saturated, aqueous sodium chloride (25 mL). The organic phase was dried over magnesium sulfate and concentrated to a final volume of 20 mL to give a precipitate. The mixture was filtered and the solids collected to give the title compound as a solid (679 mg, 51%): +APCI MS (M+H-Boc) 342.1; $^1$H NMR (400 MHz, CDCl$_3$) δ ppm 3.28-3.60 (m, 4H), 2.66 (s, 2H), 2.56 (s, 2H), 1.65 (s, 9H), 1.48-1.55 (m, 4H), 1.46 (s, 9H).

Step 3. 3-Bromo-1-tert-butyl-4,6-dihydrospiro[indazole-5,4'-piperidin]-7(1H)-one, shown below, was prepared as follows.

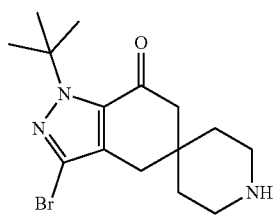 [SMILES: CC(C)(C)n1nc(Br)c2c1C(=O)CC1(CCNCC1)C2]

tert-Butyl 3-bromo-1-tert-butyl-7-oxo-1,4,6,7-tetrahydrospiro[indazole-5,4'-piperidine]-1'-carboxylate (670 mg, 1.52 mmol) and 4 M hydrogen chloride in dioxane (8 mL) were combined and stirred for 2.5 hours. To the reaction was added diethyl ether (20 mL). A precipitate formed that was filtered and the solids collected to give the title compound (573 mg, 97%): +APCI MS (M+H) 342.1; $^1$H NMR (400 MHz, CD$_3$OD) δ ppm 3.24 (t, J=5.96 Hz, 4H), 2.80 (s, 2H), 2.74 (s, 2H), 1.71-1.92 (m, 4H), 1.65 (s, 9H).

Intermediate 17

1'-Isopropyl-1'H-spiro[piperidine-4,5'-pyrano[3,2-c]pyrazol]-7'(6'H)-one, shown below, was prepared as follows.

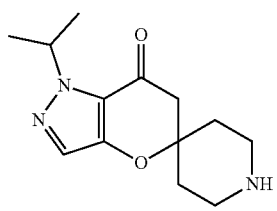 [SMILES: CC(C)n1ncc2c1C(=O)CC1(CCNCC1)O2]

Step 1. 1-(4-Hydroxy-1-(4-methoxybenzyl)-1H-pyrazol-3-yl)ethanone, shown below, was prepared as follows:

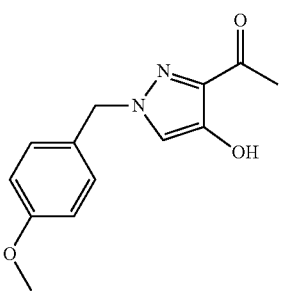 [SMILES: COc1ccc(Cn2cc(O)c(C(C)=O)n2)cc1]

To a stirred solution of (4-methoxybenzyl)hydrazine hydrochloride (13.5 g, 71.5 mmol) in water (400 mL) was added a solution of pyruvaldehyde (5.2 g, 71.5 mmol) in water (200 mL) over a 10-min period. After an additional 50 min, the reaction mixture was extracted with dichloromethane (3×300 mL), the combined extracts dried over sodium sulfate, concentrated in vacuo and the residue was used in the next transformation without further purification.

A stirred solution of the product from the above reaction (12.3 g, 59.8 mmol) and glyoxal (43 g, 299 mmol) in methanol (34 mL)/water (300 mL) was heated at 100° C. for 5 h. The reaction mixture was cooled, diluted with ethyl acetate, the organic phase dried over sodium sulfate and concentrated in vacuo. Purification of the residue was performed on an Combiflash® unit (300 g column, gradient 10-35% ethyl acetate:heptanes) afforded the title compound (6.04 g). $^1$H NMR (400 MHz, CDCl$_3$) δ ppm 8.05 (s, 1H) 7.18 (m, J=8.79 Hz, 2H), 6.93 (s, 1H), 6.87 (m, J=8.60 Hz, 2H), 5.15 (s, 2H), 3.79 (s, 3H), 2.55 (s, 3H); m/z (M+1)=247.0.

Step 2. 1-Benzyl-2'-(4-methoxybenzyl)-2'H-spiro[piperidine-4,5'-pyrano[3,2-c]pyrazol]-7'(6'H)-one, shown below, was prepared as follows.

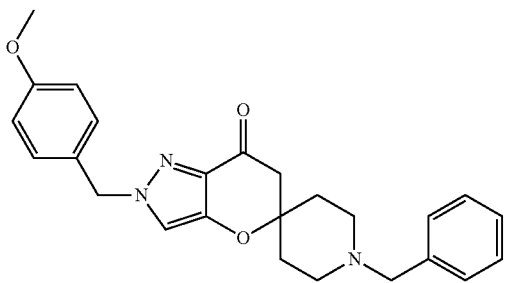 [SMILES: COc1ccc(Cn2cc3c(n2)C(=O)CC2(CCN(Cc4ccccc4)CC2)O3)cc1]

Suspended 1-(4-hydroxy-1-(4-methoxybenzyl)-1H-pyrazol-3-yl)ethanone (350 mg, 1.42 mmol) in 10 mL methanol and added N-benzyl-4-piperidone (0.25 mL, 1.42 mmol) and pyrrolidine (0.036 mL, 0.3 eq). The mixture was then heated at reflux for 18 h. The reaction was then cooled to room temperature and methanol was removed under reduced pressure. The resultant orange oil was partitioned between 50 mL ethyl acetate and 50 mL water. The aqueous phase was extracted with an additional 50 mL ethyl acetate. The organic layers were combined and dried over sodium sulfate, filtered and concentrated. The resultant oil was flash chromatographed (50-100% ethyl acetate/heptane gradient, 25 g silica) to yield 428 mg (72%) of 1-benzyl-2'-(4-methoxybenzyl)-2'H-spiro[piperidine-4,5'-pyrano[3,2-c]pyrazol]-7'(6'H)-one as a pale yellow solid. $^1$H NMR (400 MHz, CDCl$_3$) δ ppm 7.25-7.37 (m, 6H), 6.95 (s, 1H), 6.81-6.92 (m, 2H), 5.20 (s, 2H), 3.79 (s, 3H), 3.49 (s, 2H), 2.63 (s, 2H), 2.57 (d, J=11.3 Hz, 2H), 2.25-2.44 (m, 2H), 2.02 (d, J=12.5 Hz, 2H), 1.62-1.77 (m, 2H); m/z (M+1)=418.5.

Step 3. 1-Benzyl-1'H-spiro[piperidine-4,5'-pyrano[3,2-c]pyrazol]-7'(6'H)-one, shown below, was prepared as follows.

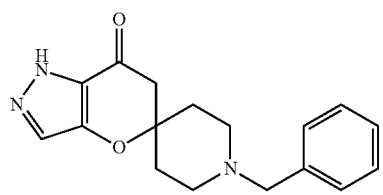 [SMILES: O=C1CC2(CCN(Cc3ccccc3)CC2)Oc2cn[nH]c21]

Dissolved 1-benzyl-2'-(4-methoxybenzyl)-2'H-spiro[piperidine-4,5'-pyrano[3,2-c]pyrazol]-7'(6'H)-one (428 mg, 1.02 mmol) in 20 mL 1,2-dichloroethane and treated with 10 mL trifluoroacetic acid. The resultant mixture was heated for 18 h at 90° C. The reaction was cooled to ambient temperature and concentrated to dryness under reduced pressure. The resultant residue was taken up in 50 mL saturated aqueous sodium bicarbonate and extracted with 2×50 mL ethyl acetate. The organic extracts were combined and dried over sodium sulfate, filtered and concentrated under reduced pressure. The resultant oil was flash chromatographed (25 g silica, stepgradient 5 column volumes 50% ethyl acetate/heptane, 10 CV 100% ethyl acetate) to yield 278 mg (91%) of 1-benzyl-1'H-spiro[piperidine-4,5'-pyrano[3,2-c]pyrazol]-7'(6'H)-one as a pale yellow solid. $^1$H NMR (400 MHz, CD$_3$OD) δ ppm 7.27 (m, 6H), 3.55 (s, 2H), 2.64 (m, 4H), 2.45 (td, J=11.7, 2.5 Hz, 2H), 2.06 (d, J=12.1 Hz, 2H), 1.74 (m, 2H); m/z (M+1)=298.5.

Step 4. 1-Benzyl-t-isopropyl-1'H-spiro[piperidine-4,5'-pyrano[3,2-c]pyrazol]-7'(6'H)-one, shown below, was prepared as follows.

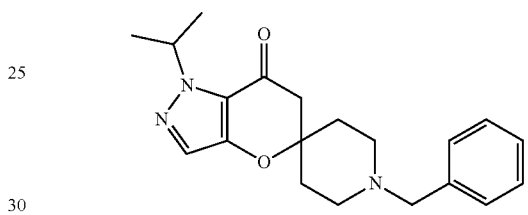

1-Benzyl-1'H-spiro[piperidine-4,5'-pyrano[3,2-c]pyrazol]-7'(6'H)-one (204 mg, 0.67 mmol) was dissolved in 10 mL tetrahydrofuran. 2-propanol (0.11 mL, 1.37 mmol) and polymer supported triphenylphosphine (0.5 g, 3 mmol/g loading) were added followed by addition of DBAD (322 mg, 1.37 mmol) and stirred at ambient temperature for 5 days. Filtered off poymer supported triphenyl phosphine and washed filtercake with 100 mL ethyl acetate. The filtrate was concentrated and the resultant yellow oil was treated with 10 mL 4N HCl/dioxane. The mixture was stirred 1 h at ambient temperature. The volatiles were removed under reduced pressure. The resultant sludge was partitioned between 50 mL sat aq. sodium bicarbonate and 50 mL ethyl acetate. The organic phase was dried over sodium sulfate, filtered and concentrated under reduced pressure. The resultant oil was flash chromatographed (30-100% ethyl acetate/heptane gradient, 10 g silica) to yield 90 mg (35%) of 1-benzyl-1'-isopropyl-1'H-spiro[piperidine-4,5'-pyrano[3,2-c]pyrazol]-7'(6'H)-one as a pale yellow solid. $^1$H NMR (400 MHz, CDCl$_3$) δ ppm 7.30 (m, 3H), 7.24 (m, 2H), 7.18 (s, 1H), 5.14 (spt, 1H), 3.52 (s, 2H), 2.60 (m, 4H), 2.41 (td, J=11.6, 2.5 Hz, 2H), 2.06 (d, J=12.5 Hz, 2H), 1.71 (m, 2H), 1.44 (m, 6H): m/z (M+1)=340.5.

Step 5. 1'-Isopropyl-1'H-spiro[piperidine-4,5'-pyrano[3,2-c]pyrazol]-7'(6'H)-one, shown below, was prepared as follows.

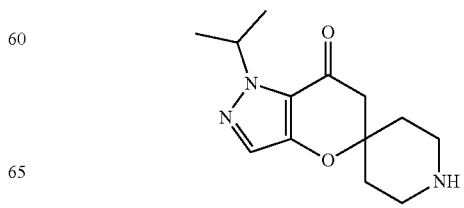

1-Benzyl-1'-isopropyl-1'H-spiro[piperidine-4,5'-pyrano[3,2-c]pyrazol]-7'(6'H)-one (81 mg, 0.22 mmol) was dissolved in 10 mL 1,2-dichloroethane. Added 1-chloroethyl chloroformate (60 mL, 0.54 mmol) was added and the mixture was stirred 1 h at reflux then cooled to room temperature. The volatiles were removed under reduced pressure and the residue taken up in 10 mL methanol and heated at reflux for 1 h. The mixture was cooled to ambient temperature and the volatiles were removed under reduced pressure. The residue was taken up in 50 mL saturated aqueous sodium bicarbonate and extracted 2×30 mL ethyl acetate. The combined organic extracts were dried over sodium sulfate, filtered and concentrated to yield 46 mg (86%) of 1'-isopropyl-1'H-spiro[piperidine-4,5'-pyrano[3,2-c]pyrazol]-7'(6'H)-one as a white solid. $^1$H NMR (400 MHz, CD$_3$OD) δ ppm 7.20 (s, 1H), 5.13 (spt, 1H), 2.93 (m, 2H), 2.80 (dt, J=12.8, 4.0 Hz, 2H), 2.64 (s, 2H), 2.02 (m, 2H), 1.63 (m, 2H), 1.40 (m, 6H); m/z (M+1)=250.2

Example 1

4-((4-(1-Tert-butyl-7-oxo-1,4,6,7-tetrahydrospiro[indazole-5,4'-piperidine]-1'-ylcarbonyl)phenoxy)methyl)benzoic acid, shown below, was prepared as follows.

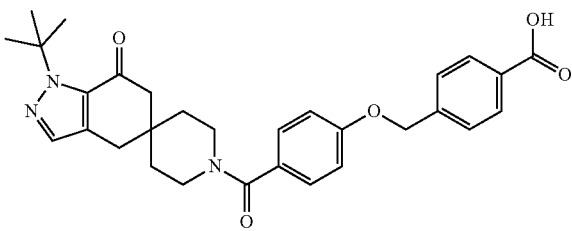 [SMILES: CC(C)(C)n1ncc2c1C(=O)CC1(CCN(C(=O)c3ccc(OCc4ccc(C(=O)O)cc4)cc3)CC1)C2]

Step 1. Methyl 4-((4-(1-tert-butyl-7-oxo-1,4,6,7-tetrahydrospiro[indazole-5,4'-piperidine]-1'-ylcarbonyl)phenoxy)methyl)benzoate, shown below was prepared as follows.

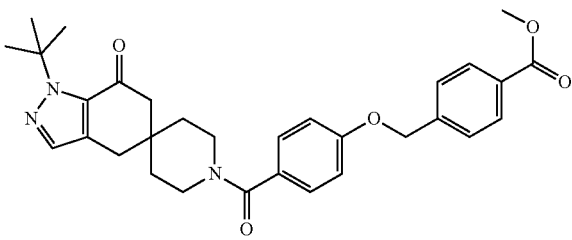 [SMILES: COC(=O)c1ccc(COc2ccc(C(=O)N3CCC4(CC3)CC(=O)c3c(cnn3C(C)(C)C)C4)cc2)cc1]

A solution of 4-(4-(methoxycarbonyl)benzyloxy)benzoic acid (25 mg, 0.087 mmol), 1-tert-butyl-4,6-dihydrospiro[indazole-5,4'-piperidin]-7(1H)-one (26 mg, 0.087 mmol), diisopropylethylamine (53 µL, 0.30 mmol), 1,2,3-benzotriazole-1-ol, monohydrate (14 mg, 0.087 mmol), 4-dimethylaminopyridine (1.1 mg, 0.01 mmol) and 1-ethyl-3-(3-dimethylaminopropyl)carbodiimide (19 mg, 0.96 mmol) in dichloromethane (0.2 mL) was heated at 30° C. for 18 hr. The reaction mixture was partitioned between ethyl acetate/aqueous 0.3N hydrochloric acid, the organic phase was dried over sodium sulfate, concentrated in vacuo and purified by preparative HPLC to afford methyl 4-((4-(1-tert-butyl-7-oxo-1,4,6,7-tetrahydrospiro[indazole-5,4'-piperidine]-1'-ylcarbonyl)phenoxy)methyl) benzoate. HPLC column: Waters Atlantis C18 4.6×50 mm, 5 um, solvent: acetonitrile:water (0.05% TFA); flow rate 2 mL/min; gradient (% organic) start=5%, end=95%, gradient time=4 min, retention time=3.68 min; m/z=530 (M+1).

Step 2. To a stirred solution of methyl 4-((4-(1-tert-butyl-7-oxo-1,4,6,7-tetrahydrospiro[indazole-5,4'-piperidine]-1'-ylcarbonyl)phenoxy)methyl)benzoate (39 mg, 0.07 mmol) in tetrahydrofuran (0.75 mL) was added aqueous lithium hydroxide (0.22 mL, 0.22 mmol). After 18 hr, 0.3 mL of 1N aqueous hydrochloric acid, and 0.2 mL of saturated aqueous sodium chloride were added. The resulting mixture was extracted with 2-methyltetrahydrofuran (3×4 mL), the combined organic layers dried over sodium sulfate and concentrated in vacuo to afford a gum (46 mg). Purification by preparative HPLC afforded the title compound (26 mg). HPLC column: Waters Atlantis C18 4.6×50 mm, 5 um, solvent: acetonitrile:water (0.05% TFA); flow rate 2 mL/min; gradient (% organic) start=5%, end=95%, gradient time=4 min, retention time=3.19 min; m/z=516 (M+1).

Example 2

3-(4-(1-Isopropyl-7-oxo-1,4,6,7-tetrahydrospiro[indazole-5,4'-piperidine]-1'-ylcarbonyl)-6-methoxypyridin-2-yl)benzoic acid, shown below, was prepared as follows.

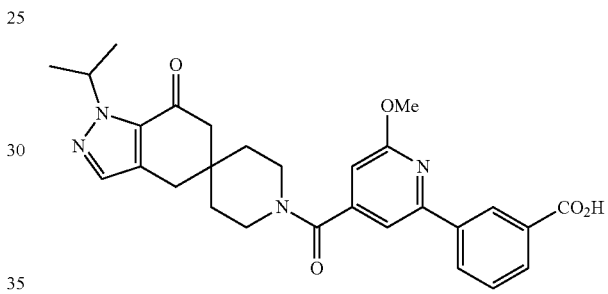

Step 1. Tert-butyl 3-(4-(1-isopropyl-7-oxo-1,4,6,7-tetrahydrospiro[indazole-5,4'-piperidine]-1'-ylcarbonyl)-6-methoxypyridin-2-yl)benzoate, shown below, was prepared as follows.

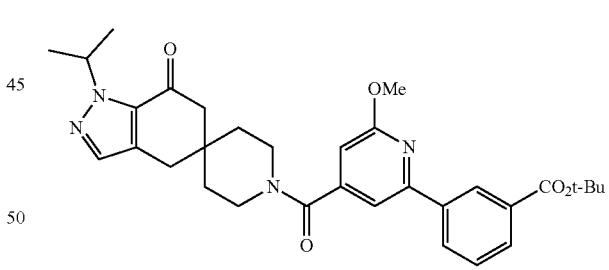

A solution of 2-(4-(tert-butoxycarbonyl)phenyl)-6-methoxyisonicotinic acid (500 mg, 1.52 mmol) and 1,1-carbonyldiimidazole (271 mg, 1.67 mmol) in tetrahydrofuran (30 mL) was stirred at reflux for 1 hr. After cooling to room temperature 1-isopropyl-4,6-dihydrospiro[indazole-5,4'-piperidin]-7(1H)-one (539 mg, 1.68 mmol) and triethylamine (0.32 mL, 2.28 mmol) were added sequentially and the resulting slurry was heated at reflux temperature for 1 hr. After cooling, the reaction mixture was diluted into ethyl acetate, washed with 1N aqueous hydrochloric acid, saturated aqueous sodium chloride, dried over sodium sulfate to afford tert-butyl 3-(4-(1-isopropyl-7-oxo-1,4,6,7-tetrahydrospiro[indazole-5,4'-piperidine]-1'-ylcarbonyl)-6-methoxypyridin-2-yl)benzoate (850 mg) as a white foam.

This material was taken onto the next step without further purification. ¹H NMR (400 MHz, CDCl₃) δ ppm 8.60 (t, J=1.66 Hz, 1H), 8.20 (dt, J=8.05, 1.44 Hz, 1H), 8.01 (dt, J=7.80, 1.37 Hz, 1H), 7.50 (t, J=7.80 Hz, 1H), 7.36 (s, 1H), 7.33 (d, J=0.98 Hz, 1H), 6.64 (d, 1H), 5.35 (spt, J=6.44 Hz, 1H), 4.04 (s, 3H), 3.71-3.84 (m, 2H), 3.36-3.42 (m, 2H), 2.79 (d, J=2.34 Hz, 2H), 2.58 (s, 2H), 1.66-1.72 (m, 2H), 1.61 (s, 9H), 1.56 (s, 2H), 1.40-1.48 (m, 6H); m/z (M+1)= 559.2.

Step 2. A solution of tert-butyl 3-(4-(1-isopropyl-7-oxo-1,4,6,7-tetrahydrospiro[indazole-5,4'-piperidine]1'-ylcarbonyl)-6-methoxypyridin-2-yl)benzoate (850 mg, 1.52 mmol) in dichloromethane (40 mL) and trifluoroacetic acid (13 mL) was stirred for 18 hr. The solvents were removed in vacuo and the residue was purified by flash chromatography (40 g silica gel column, eluting with a gradient of 20-100% ethyl acetate:heptanes (0.5% acetic acid) to afford the title compound as a white solid (568 mg). ¹H NMR (400 MHz, CD₃OD) δ ppm 8.72 (t, J=1.66 Hz, 1H), 8.31 (dt, J=8.15, 1.39 Hz, 1H), 8.06 (dt, J=7.80, 1.27 Hz, 1H), 7.57 (t, J=7.80 Hz, 1H), 7.48 (d, J=0.98 Hz, 1H), 7.40 (s, 1H), 6.74 (d, 1H), 5.36 (spt, J=6.76 Hz, 1H), 4.05 (s, 3H), 3.82-3.91 (m, 1H), 3.65-3.74 (m, 1H), 3.44 (t, J=5.76 Hz, 2H), 3.24 (s, 0H), 2.87 (d, J=1.37 Hz, 2H), 2.63 (d, J=2.93 Hz, 2H), 1.63-1.71 (m, 2H), 1.52-1.60 (m, 2H), 1.41 (d, J=6.24 Hz, 3H), 1.38 (d, J=6.24 Hz, 3H); m/z (M+1)=503.2

Example 3

3-(4-(1-isopropyl-7-oxo-1,4,6,7-tetrahydrospiro[indazole-5,4'-piperidine]-1'-ylcarbonyl)-6-oxo-1,6-dihydropyridin-2-yl)benzoic acid, shown below, was prepared as follows.

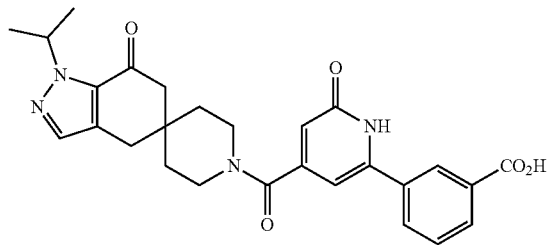 [SMILES: CC(C)n1ncc2c1C(=O)CC1(CCN(C(=O)c3cc(-c4cccc(C(=O)O)c4)[nH]c(=O)c3)CC1)C2]

A mixture of 3-(4-(1-isopropyl-7-oxo-1,4,6,7-tetrahydrospiro[indazole-5,4'-piperidine]-1'-ylcarbonyl)-6-methoxypyridin-2-yl)benzoic acid (30 mg, 0.06 mmol), potassium iodide (30 mg, 0.18 mmol) in acetic acid (1 mL) was stirred at 120° C. for 7 hr. The reaction mixture was filtered, concentrated in vacuo and purified by preparative HPLC to afford the title compound (12 mg). HPLC column: Waters Atlantis C18 4.6×50 mm, 5 um, solvent: acetonitrile:water (0.05% TFA); flow rate 2 mL/min; gradient (% organic) start=5%, end=95%, gradient time=4 min, retention time=2.32 min; m/z=489.1451 (M+1).

The compounds listed in Table 1 below were prepared using procedures analogous to those described above for the synthesis of the compounds of Examples 1-3 using the appropriate starting materials which are available commercially, prepared using preparations well-known to those skilled in the art, or prepared in a manner analogous to routes described above for other intermediates. The compounds listed below were isolated initially as the free base and may be converted to a pharmaceutically acceptable salt for testing.

TABLE 1

| Ex. | R¹ | —C(O)—A¹—L—A² | Analytical Data |
|---|---|---|---|
| 4 | t-butyl | | MS (MH + 1) 516.3, ¹H NMR (CD₃OD, 400 MHz): 8.70 (s, 1H), 8.27 (d, 1H), 8.03 (d, 1H), 7.46 (t, 1H), 7.45 (d, 1H), 7.31 (s, 1H), 7.16 (d, 1H), 3.40-3.75 (br.s, 4H), 3.05 (s, 3H), 2.86 (s, 2H), 2.60 (s, 2H), 1.61 (s, 13H). |
| 5 | isopropyl | | MS (MH + 1) 558.3; ¹H NMR (CDCl₃, 400 MHz): 8.36 (s, 1H), 8.27 (d, 1H), 7.49 (t, 1H), 7.37 (s, 2H), 7.05 (d, 1H), 3.56 (h, 1H), 3.61 (m, 4H), 3.07 (s, 3H), 2.58 (s, 2H), 1.48 (m, 4H), 1.44 (d, 6H). |

TABLE 1-continued

| Ex. | R¹ | —C(O)—A¹—L—A² | Analytical Data |
|---|---|---|---|
| 6 | t-butyl | [4'-acyl-biphenyl-3-carboxylic acid substituent] | MS (MH + 1) 486.24; ¹H NMR (400 MHz, CDCl$_3$) 8.30 (s, 1H), 8.21 (d, 1H), 7.79 (d, 1H), 7.65 (d, 2H), 7.55 (t, 1H), 7.50 (d, 2H), 7.31 (s, 1H), 3.62 (br, 1H), 3.48 (br, 2H), 2.82 (s, 2H), 2.62 (s, 2H), 1.80-1.48 (m, 13H), 0.86 (br, 1H). |
| 7 | isopropyl | [4'-acyl-biphenyl-3-carboxylic acid substituent] | MS (MH + 1) 472.26; ¹H NMR (400 MHz, CDCl$_3$) 8.31 (s, 1H), 8.09 (d, 1H), 7.79 (d, 1H), 7.65 (d, 2H), 7.53 (t, 1H), 7.50 (d, 2H), 7.38 (s, 1H), 5.37-5.35 (m, 1H), 3.82 (br, 1H), 3.47 (br, 2H), 2.81 (s, 2H), 2.60 (s, 2H), 1.70-1.55 (m, 5H), 1.45 (d, 6H). |
| 8 | isopropyl | [6-(methylamino)pyridine-phenyl-carboxylic acid substituent] | MS (MH + 1) 502.27; ¹H NMR (CD$_3$OD, 400 MHz) δ ppm 8.15 (d, 2H), 8.07 (d, 2H), 7.47 (d, 1H), 7.40 (s, 1H), 7.19 (d, 1H), 5.35 (h, 1H), 3.50 (br. s, 4H), 3.05 (s, 3H), 2.86 (s, 2H), 2.62 (s, 2H), 1.60 (br. s, 4H), 1.40 (d, 6H). |
| 9 | isopropyl | [6-methoxypyridine-phenyl-carboxylic acid substituent] | MS (MH + 1) 503.5; ¹H NMR (400 MHz, CDCl$_3$) δ ppm 1.39-1.48 (m, 6 H), 1.53 (bs, 2H), 1.70 (br. s., 2H), 2.59 (s, 2 H), 2.80 (s, 2H), 3.40 (br. s., 2 H), 3.71-3.88 (m, 2H), 4.06 (s, 3 H) 5.31-5.42 (m, 1 H) 6.68 (s, 1 H) 7.38 (s, 2 H) 8.15 (m, 4 H). |
| 10 | t-butyl | [6-methoxypyridine-phenyl-carboxylic acid substituent] | MS (MH + 1) 517.6; ¹H NMR (400 MHz, CDCl$_3$) δ ppm 1.50-1.57 (m, 2H), 1.66 (s, 9 H), 1.67-1.74 (m, 2H), 2.64 (s, 2 H) 2.83 (s, 2 H), 3.39-3.38 (m, 2H), 3.72-3.91 (m, 4H), 4.07 (s, 3 H) 6.71 (d, J = 0.98 Hz, 1 H) 7.32 (s, 1 H) 7.39 (d, J = 0.98 Hz, 1 H) 8.05-8.26 (m, 4 H) |

TABLE 1-continued
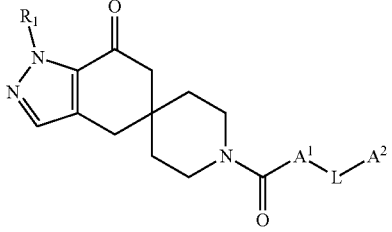
| Ex. | R¹ | —C(O)—A¹—L—A² | Analytical Data |
|---|---|---|---|
| 11 | t-butyl | 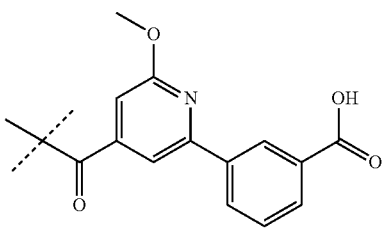 | MS (M + H) 517.6; 1H NMR (400 MHz, CDCl₃) δ ppm 1.49-1.57 (m, 2H), 1.66 (s, 9 H), 1.68-1.75 (m, 2H), 2.64 (s, 2 H), 2.84 (s, 2 H), 3.43 (bs, 2H), 3.72-3.92 (m, 2H), 4.08 (s, 3 H), 6.68 (d, J = 0.98 Hz, 1 H), 7.32 (s, 1 H), 7.45 (d, J = 0.98 Hz, 1 H), 7.59 (t, 1 H), 8.16 (d, J = 7.82 Hz, 1 H), 8.34 (d, J = 7.82 Hz, 1 H), 8.76 (s, 1 H). |
| 12 | t-butyl | 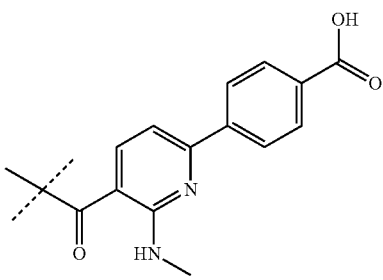 | MS (MH + 1) 406.5; ¹H NMR (400 MHz, CDCl₃) δ ppm 8.00 (s, 1 H) 7.79 (s, 1 H) 7.32-7.47 (m, 3 H) 5.30-5.41 (m, 1 H) 4.07 (s, 3 H) 3.61 (br. s., 4 H) 2.79 (s, 2 H) 2.58 (s, 2 H) 1.61 (br. s., 2 H) 1.53 (br. s., 2 H) 1.43 (d, J = 6.84 Hz, 6 H) |
| 13 | t-butyl | 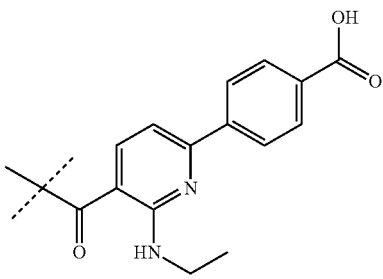 | MS (MH + 1) 516.28; ¹H NMR (CDCl₃, 400 MHz): 8.16 (m, 4H), 7.38 (br.s, 2H), 7.05 (d, 1H), 5.37 (h, 1H), 3.48 (m 6H), 2.60 (s, 2H), 2.16 (br.s, 4H), 1.45 (d, 6H), 1.23 (app. br.s, 3H). |
| 14 | isopropyl | 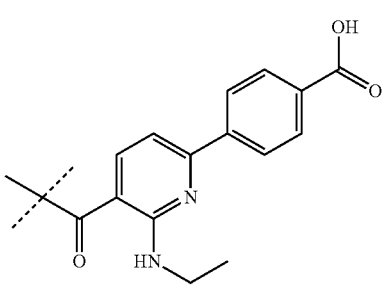 | MS (MH + 1) 511, ¹H NMR (CDCl₃, 400 MHz) δ ppm 8.16 (m, 4H), 7.38 (br.s, 2H), 7.05 (d, 1H), 5.37 (h, 1H), 3.48 (m 6H), 2.60 (s, 2H), 2.16 (br.s, 4H), 1.45 (d, 5H), 1.23 (app. br.s, 3H). |

TABLE 1-continued

| Ex. | R¹ | —C(O)—A¹—L—A² | Analytical Data |
|---|---|---|---|
| 15 | isopropyl | 3-(1H-indol-2-yl carbonyl)-phenyl with benzoic acid (meta-COOH) | MS (MH + 1) 511; ¹H NMR (400 MHz, DMSO-d₆) δ ppm 13.04 (br. s., 1 H), 11.77 (s, 1 H), 8.16 (s, 1 H), 7.93 (d, J = 7.8 Hz, 1 H), 7.89 (d, J = 7.8 Hz, 1 H), 7.60 (t, J = 7.7 Hz, 1 H), 7.40-7.48 (m, 2 H), 7.27 (t, J = 7.7 Hz, 1 H), 7.14 (d, J = 7.2 Hz, 1 H), 6.74 (d, J = 1.2 Hz, 1 H), 5.24 (spt, J = 6.6 Hz, 1 H), 3.75 (br. s., 2 H), 3.65 (br. s., 2 H), 2.79 (s, 2 H), 2.58 (s. 2 H), 1.50 (br. s., 4H), 1.33 (d, J = 6.6 Hz, 6 H). |
| 16 | isopropyl | 4-(1H-indol-2-yl carbonyl)-phenyl with benzoic acid (para-COOH) | MS (MH + 1) 511; ¹H NMR (400 MHz, DMSO-d₆) δ ppm 12.75-13.11 (m, 1 H), 11.78 (s, 1 H), 8.03 (d, J = 8.4 Hz, 2 H), 7.76 (d, J = 8.2 Hz, 2 H), 7.40-7.50 (m, 2 H), 7.27 (t, J = 7.7 Hz, 1 H), 7.17 (d, J = 7.0 Hz, 1 H), 6.79 (d, J = 1.2 Hz, 1 H), 5.25 (spt, J = 6.5 Hz, 1 H), 3.76 (br. s., 2H), 3.66 (br. s., 2 H), 2.79 (s, 2H), 2.59 (s, 2 H), 1.44-1.58 (m, 4 H), 1.33 (d, J = 6.6 Hz, 6 H). |
| 17 | t-butyl | 3-(1H-indol-2-yl carbonyl)-phenyl with benzoic acid (meta-COOH) | MS (MH + 1) 525; ¹H NMR (400 MHz, DMSO-d₆) ᵈ ppm 11.76 (s, 1 H), 8.16 (s, 1 H), 7.93 (d, J = 7.8 Hz, 1 H), 7.88 (d, J = 7.4 Hz, 1 H), 7.59 (t, J = 7.7 Hz, 1 H), 7.43 (d, J = 8.2 Hz, 1 H), 7.36 (s, 1 H), 7.27 (t, J = 7.7 Hz, 1 H), 7.14 (d, J = 7.2 Hz, 1 H), 6.74 (s, 1 H), 3.78 (d, J = 12.9 Hz, 2H), 3.63 (br. s., 2 H), 2.81 (s, 2 H), 2.60 (s, 2 H), 1.55 (s. 9 H), 1.49 (br. s., 4 H) |
| 18 | t-butyl | 4-(1H-indol-2-yl carbonyl)-phenyl with benzoic acid (para-COOH) | MS (MH + 1); ¹H NMR (400 MHz, DMSO-d₆) δ ppm 11.77 (s, 1 H), 8.03 (d, J = 8.2 Hz, 2 H), 7.76 (d, J = 8.2 Hz, 2 H), 7.45 (d, J = 8.2 Hz, 1 H), 7.37 (s, 1 H), 7.27 (t, J = 7.7 Hz, 1 H), 7.16 (d, J = 7.2 Hz, 1 H), 6.79 (d, J = 1.0 Hz, 1 H), 3.78 (br. s., 2 H), 3.64 (br. s., 2 H), 2.82 (s, 2 H), 2.61 (s, 2 H), 1.55 (s, 9H), 1.49 (br. s., 4 H). |

TABLE 1-continued

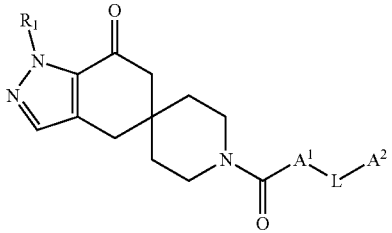

| Ex. | R¹ | —C(O)—A¹—L—A² | Analytical Data |
|---|---|---|---|
| 19 | t-butyl | 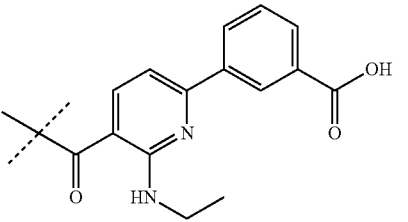 | MS (MH + 1) 530.31; ¹H NMR (CD₃OD, 400 MHz) δ ppm 8.64 (s, 1H), 8.25 (d, 1H), 8.02 (d, 1H), 7.80 (br. s, NH), 7.50 (m, 2H), 7.30 (s, 1H), 7.10 (d, 1H). |
| 20 | isopropyl | 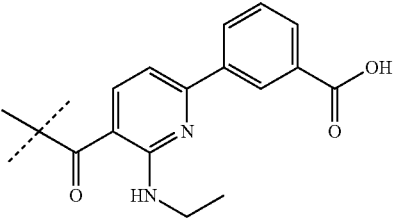 | MS (MH + 1) 516.28; ¹H NMR (DMSO-d₆, 400 MHz) δ ppm 8.15 (d, 2H), 7.97 (d, 2H), 7.41 (d, 1H), 7.36 (s, 1H), 7.20 (d, 1H), 6.23 (br.s, NH), 3.87 (br.s, 4H), 2.92 (s, 3H), 2.78 (s, 2H), 2.58 (s, 2H), 1.54 (s, 9H), 1.46 (br.s, 4H). |
| 21 | t-butyl | 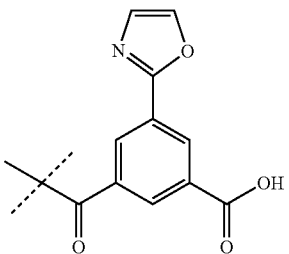 | MS (MH + 1) 477; LC/MS retention time 2.83 minutes on a Waters Atlantis dC18 4.6 × 50 mm, 5 μm gradient elution (5% to 95%) with water: acetonitrile (0.05% TFA), 4 minute gradient and 5 minute hold time |
| 22 | isopropyl | 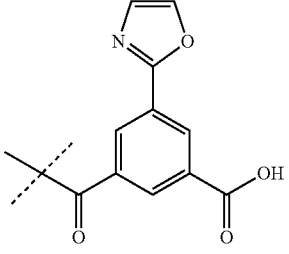 | MS (MH + 1) 463; LC/MS retention time 2.57 minutes on a Waters Atlantis dC18 4.6 × 50 mm, 5 μm gradient elution (5% to 95%) with water: acetonitrile (0.05% TFA), 4 minute gradient and 5 minute hold time |
| 23 | isopropyl | 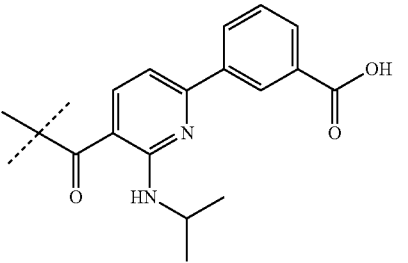 | MS (MH + 1) 530.29; ¹H NMR (CDCl₃, 400 MHz) δ ppm 8.72 (s, 1H), 8.33 (d, 1H), 8.12 (d, 1H), 7.52 (t, 1H), 7.36 (d, 2H), 7.05 (d, 1H), 5.67 (br. s, 1H), 5.36 (h, 1H), 4.43 (m, 1H), 3.62 (m, 4H), 3.09 (s, 1H), 2.81 (s, 2H), 2.59 (s, 2H), 1.61 (m, 4H), 1.45 (d, 6H), 1.30 (d, 6H) |

TABLE 1-continued

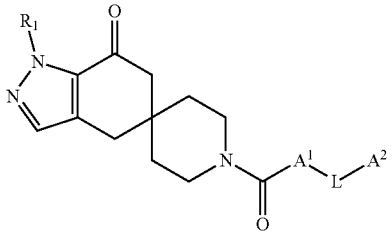

| Ex. | R¹ | —C(O)—A¹—L—A² | Analytical Data |
|---|---|---|---|
| 24 | t-butyl | 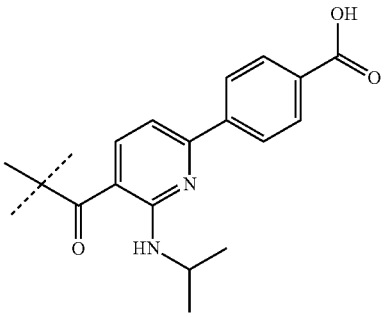 | MS (MH + 1) 544.3; ¹H NMR (CDCl$_3$, 400 MHz) δ ppm 8.57 (s, 1H), 8.36 (d, 1H), 7.36-7.54 (m, 2H), 7.31 (s, 1H), 7.04 (d, 1H), 4.22 (br. s, 1H), 3.65 (br.s, 4H), 2.83 (s, 2H), 2.62 (s, 2H), 1.65 (s, 13 H), 1.32 (d, 6H) |
| 25 | isopropyl | 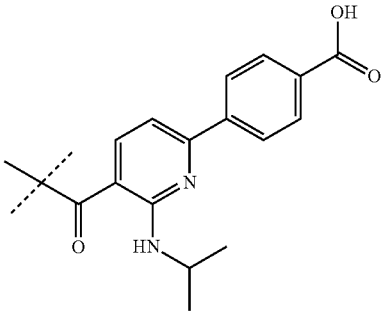 | MS (MH + 1) 530.29; ¹H NMR (CDCl$_3$, 400 MHz) δ ppm 8.10-8.18 (dd, 4H), 7.38 (m, 2H), 7.04 (d, 1H), 5.39 (h, 1H), 4.36 (br. s, 1H), 3.51 (br. s, 4H), 2.81 (s, 2H), 2.59 (s, 2H), 1.70 (m, 4H), 1.45 (d, 6H), 1.29 (d, 6H) |
| 26 | isopropyl | 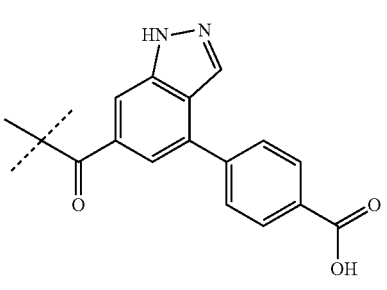 | MS (MH + 1) 512.3; ¹H NMR (400 MHz, DMSO-d$_6$) δ ppm 8.24 (s, 1 H), 8.07 (m, 2 H), 7.86 (m, 2 H), 7.57 (s, 1 H), 7.43 (s, 1 H), 7.25 (d, J = 0.98 Hz, 1 H), 5.24 (t, J = 6.63 Hz, 1 H), 3.71 (br. s., 2 H), 3.59 (br. s., 2H), 2.78 (br. s., 2 H), 2.60 (s, 2 H), 1.46 (br. s., 4 H), 1.32 (d). |
| 27 | isopropyl | 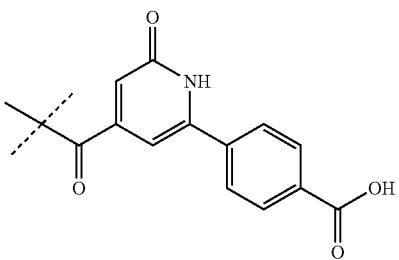 | MS (MH + 1) 489.15; LC/MS retention time 2.29 minutes on a Waters Atlantis dC18 4.6 × 50 mm, 5 Im gradient elution (5% to 95%) with water: acetonitrile (0.05% TFA), 4 minute gradient and 5 minute hold time |

TABLE 1-continued

| Ex. | R¹ | —C(O)—A¹—L—A² | Analytical Data |
|---|---|---|---|
| 28 | isopropyl | [structure: 7-azaindole with phenyl-COOH] | MS (MH + 1) 512.2; ¹H NMR (400 MHz, CD₃OD) δ ppm 8.54 (d, J = 6.06 Hz, 1 H), 8.48 (t, J = 1.66 Hz, 1 H), 8.25 (dt, J = 7.77, 1.39 Hz, 1 H), 8.10 (dt, J = 8.11, 1.42 Hz, 1 H), 7.70-7.80 (m, 2 H), 7.41 (s, 1 H), 7.17 (s, 1 H), 5.32-5.42 (m, 1 H), 3.85 (br. s., 4 H), 2.89 (s, 2 H), 2.64 (s, 2 H), 1.66 (br. s., 4 H) 1.41(d). |
| 29 | isopropyl | [structure: 7-azaindole with phenyl-COOH] | MS (MH + 1) 512.3; ¹H NMR (400 MHz, DMSO-d₆) δ ppm 8.37 (d, J = 4.88 Hz, 1 H) 8.07 (m, 2 H) 7.87 (m, 2 H) 7.43 (s, 1 H) 7.26 (d, J = 4.88 Hz, 1 H) 6.79 (d, J = 2.15 Hz, 1 H) 5.23 (d, J = 6.44 Hz, 1 H) 3.69 (s, 4 H) 2.78 (s, 2 H) 2.59 (s, 2 H) 1.50 (br. s., 4 H) 1.32 (d). |
| 30 | isopropyl | [structure: azaindole with phenyl-COOH] | MS (MH + 1) 512; ¹H NMR (400 MHz, CD₃OD) δ ppm 8.46 (d, J = 6.8 Hz, 1 H), 8.33-8.37 (m, 2 H), 8.05-8.10 (m, 2 H), 7.99 (dd, J = 6.7, 0.7 Hz, 1 H), 7.43 (s, 1 H), 7.34 (d, J = 0.8 Hz, 1 H), 5.38 (spt, J = 6.5 Hz, 1 H), 3.75-3.94 (m, 4 H), 2.91 (s, 2 H), 2.66 (s, 2 H), 1.68 (br. s., 4 H), 1.43 (s, 6 H). |
| 31 | isopropyl | [structure: indole with phenyl-CH₂-COOH and OMe] | MS (MH + 1) 555.3; LC/MS retention time 3.09 minutes. Column: Waters Atlantis dC18 4.6 × 50 mm, 5 um Modifier: TFA 0.05% Gradient: 95% H20/5% MeCN linear to 5% H20/95% MeCN over 4.0 min, HOLD at 5% H20/95% MeCN to 5.0 min. Flow: 2.0 mL/min. |

TABLE 1-continued

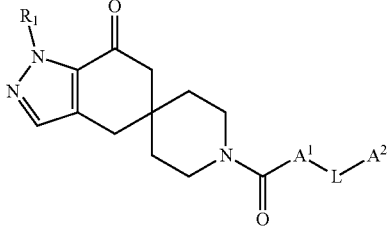

| Ex. | R¹ | —C(O)—A¹—L—A² | Analytical Data |
|---|---|---|---|
| 32 | isopropyl | 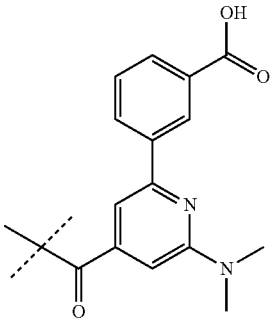 | MS (MH + 1) 516.3; LC/MS retention time 2.77 minutes. Column: Waters Atlantis dC18 4.6 × 50 mm, 5 um Modifier: TFA 0.05% Gradient: 95% H20/5% MeCN linear to 5% H20/95% MeCN over 4.0 min, HOLD at 5% H20/95% MeCN to 5.0 min. Flow: 2.0 mL/min. |
| 33 | isopropyl | 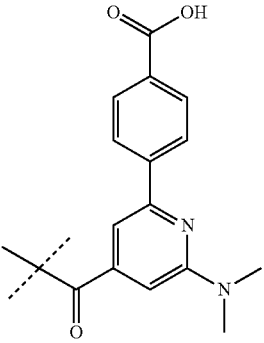 | MS (MH + 1) 516; ¹H NMR (400 MHz, CD₃OD) δ ppm 8.18 (d, J = 8.4 Hz, 2 H), 7.97 (d, J = 8.4 Hz, 2H), 7.42 (s, 1 H), 7.15 (d, J = 0.8 Hz, 1 H), 7.07 (s, 1 H), 5.38 (spt, J = 6.7 Hz, 1 H), 3.83-3.91 (m, 1 H), 3.69-3.76 (m, 1 H), 3.45-3.52 (m, 2 H), 3.33-3.36 (m, 6 H), 2.90 (s, 2 H), 2.66 (d, J = 2.7 Hz, 2 H), 1.68-1.74 (m, 2 H), 1.58-1.64 (m, 2 H), 1.42 (t, J = 6.3 Hz, 6 H). |
| 34 | isopropyl | 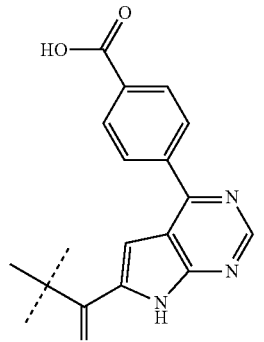 | MS (MH + 1) 513.3; LC/MS retention time 2.4 minutes. Column: Waters Atlantis dC18 4.6 × 50 mm, 5 um Modifier: TFA 0.05% Gradient: 95% H20/5% MeCN linear to 5% H20/95% MeCN over 4.0 min, HOLD at 5% H20/95% MeCN to 5.0 min. Flow: 2.0 mL/min. |

TABLE 1-continued

| Ex. | R¹ | —C(O)—A¹—L—A² | Analytical Data |
|---|---|---|---|
| 35 | isopropyl | (3-carboxyphenyl at 4-position of 1H-pyrrolo[3,2-c]pyridine, 2-acyl linkage) | MS (MH + 1) 512.2; LC/MS retention time 2.2 minutes. Column: Waters Atlantis dC18 4.6 × 50 mm, 5 um Modifier: TFA 0.05% Gradient: 95% H20/5% MeCN linear to 5% H20/95% MeCN over 4.0 min, HOLD at 5% H20/95% MeCN to 5.0 min. Flow: 2.0 mL/min. |
| 36 | isopropyl | (3-carboxyphenyl at 4-position of 7H-pyrrolo[2,3-d]pyrimidine, 6-acyl linkage) | MS (MH + 1) 513.3; LC/MS retention time 2.41 minutes. Column: Waters Atlantis dC18 4.6 × 50 mm, 5 um Modifier: TFA 0.05% Gradient: 95% H20/5% MeCN linear to 5% H20/95% MeCN over 4.0 min, HOLD at 5% H20/95% MeCN to 5.0 min. Flow: 2.0 mL/min. |
| 37 | isopropyl | (4-carboxyphenyl at 4-position of 1H-indole, 6-acyl linkage) | MS (MH + 1) 511.2; LC/MS retention time 2.82 minutes. Column: Waters Atlantis dC18 4.6 × 50 mm, 5 um Modifier: TFA 0.05% Gradient: 95% H20/5% MeCN linear to 5% H20/95% MeCN over 4.0 min, HOLD at 5% H20/95% MeCN to 5.0 min. Flow: 2.0 mL/min. |
| 38 | isopropyl | (4-carboxyphenyl at 4-position of 1H-pyrrolo[3,2-c]pyridine, 2-acyl linkage) | MS (MH + 1) 512.24; LC/MS retention time 2.21 minutes. Column: Waters Atlantis dC18 4.6 × 50 mm, 5 um Modifier: TFA 0.05% Gradient: 95% H20/5% MeCN linear to 5% H20/95% MeCN over 4.0 min, HOLD at 5% H20/95% MeCN to 5.0 min. Flow: 2.0 mL/min. |

TABLE 1-continued

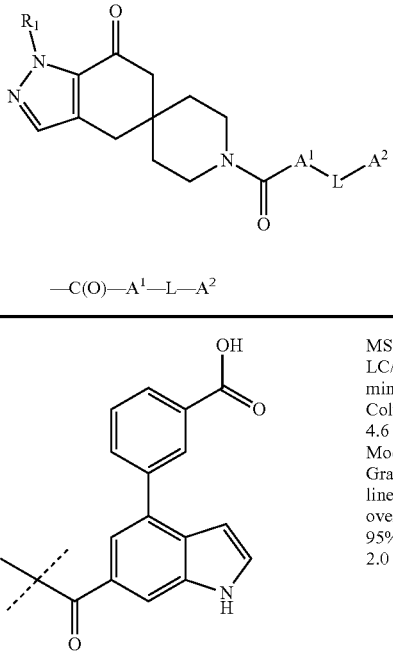

| Ex. | R¹ | —C(O)—A¹—L—A² | Analytical Data |
|---|---|---|---|
| 39 | isopropyl | 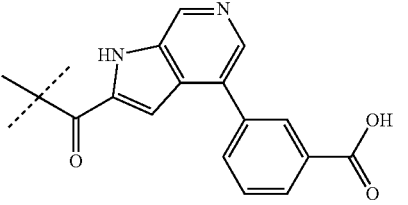 | MS (MH + 1) 511.3; LC/MS retention time 2.87 minutes. Column: Waters Atlantis dC18 4.6 × 50 mm, 5 um Modifier: TFA 0.05% Gradient: 95% H20/5% MeCN linear to 5% H20/95% MeCN over 4.0 min, HOLD at 5% H20/ 95% MeCN to 5.0 min. Flow: 2.0 mL/min. |
| 40 | isopropyl | 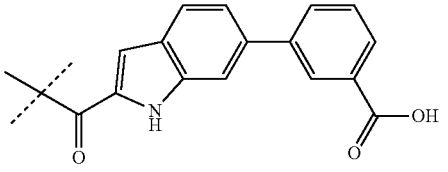 | MS (MH + 1) 512.28; LC/MS retention time 2.27 minutes. Column: Waters Atlantis dC18 4.6 × 50 mm, 5 um Modifier: TFA 0.05% Gradient: 95% H20/5% MeCN linear to 5% H20/95% MeCN over 4.0 min, HOLD at 5% H20/ 95% MeCN to 5.0 min. Flow: 2.0 mL/min. |
| 41 | isopropyl | | MS (MH + 1) 511.2; LC/MS retention time 3.19 minutes. Column: Waters Atlantis dC18 4.6 × 50 mm, 5 um Modifier: TFA 0.05% Gradient: 95% H20/5% MeCN linear to 5% H20/95% MeCN over 4.0 min, HOLD at 5% H20/ 95% MeCN to 5.0 min. Flow: 2.0 mL/min. |
| 42 | isopropyl | 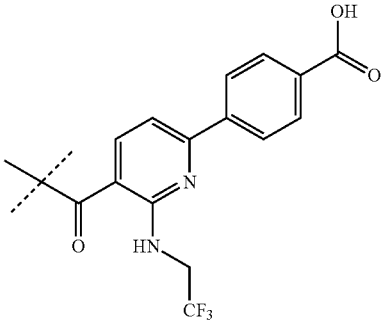 | MS (MH + 1) 570.27; LC/MS retention time 3.11; minutes. Column: Waters Atlantis dC18 4.6 × 50 mm, 5 um Modifier: TFA 0.05% Gradient: 95% H20/5% MeCN linear to 5% H20/95% MeCN over 4.0 min, HOLD at 5% H20/ 95% MeCN to 5.0 min. Flow: 2.0 mL/min. |

TABLE 1-continued

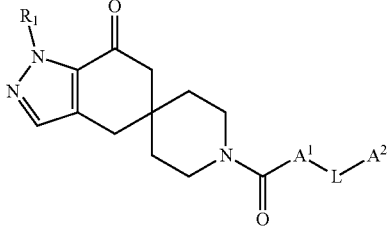

| Ex. | R¹ | —C(O)—A¹—L—A² | Analytical Data |
|---|---|---|---|
| 43 | isopropyl | 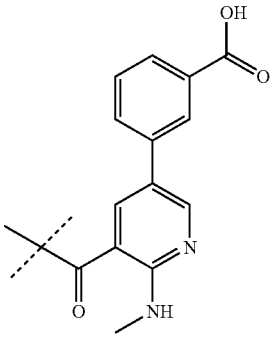 | MS (MH + 1) 502; LC/MS retention time 2.06 minutes. Column: Waters Sunfire C18 4.6 × 50 mm, 5 um Modifier: TFA 0.05% Gradient: 95% H20/5% MeCN linear to 5% H20/95% MeCN over 4.0 min, HOLD at 5% H20/95% MeCN to 5.0 min. Flow: 2.0 mL/min. |
| 44 | isopropyl | 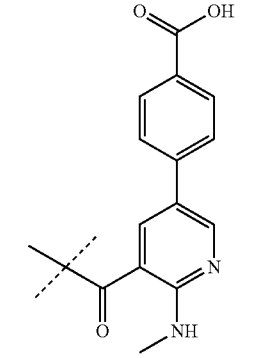 | MS (MH + 1) 502; LC/MS retention time 2.09 minutes. Column: Waters Sunfire C18 4.6 × 50 mm, 5 um Modifier: TFA 0.05% Gradient: 95% H20/5% MeCN linear to 5% H20/95% MeCN over 4.0 min, HOLD at 5% H20/95% MeCN to 5.0 min. Flow: 2.0 mL/min. |
| 45 | isopropyl | 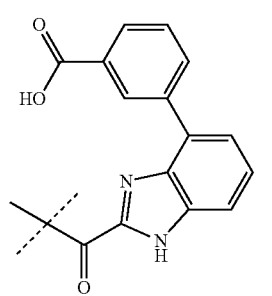 | MS (MH + 1) 516; ¹H NMR (CD₃OD + 1 drop DCM, 400 MHz): 8.70 (s, 1H), 8.14 (d, 1H), 8.03 (d, 1H), 7.59 (m, 2H), 7.50 (m, 1H), 7.42 (d, 1H), 7.41 (s, 1H), 5.41 (m, 1h), 4.45 (m, 1H), 4.28 (m, 1H), 3.89 (m, 1H), 3.73 (m, 1h), 2.89 (dd, 2H), 2.63 (s, 2H), 1.79 to 1.62 (m,4H), 1.42 (d, 6H). |
| 46 | isopropyl | 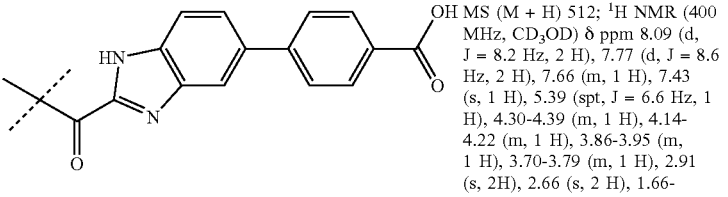 | MS (M + H) 512; ¹H NMR (400 MHz, CD₃OD) δ ppm 8.09 (d, J = 8.2 Hz, 2 H), 7.77 (d, J = 8.6 Hz, 2 H), 7.66 (m, 1 H), 7.43 (s, 1 H), 5.39 (spt, J = 6.6 Hz, 1 H), 4.30-4.39 (m, 1 H), 4.14-4.22 (m, 1 H), 3.86-3.95 (m, 1 H), 3.70-3.79 (m, 1 H), 2.91 (s, 2H), 2.66 (s, 2 H), 1.66-1.74 (m, 4 H), 1.42 (d, J = 6.8 Hz, 6 H) |

TABLE 1-continued

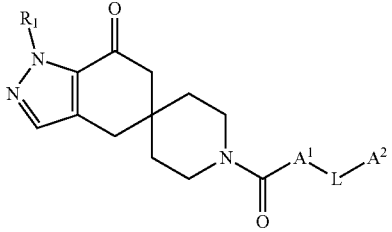

| Ex. | R[1] | —C(O)—A[1]—L—A[2] | Analytical Data |
|---|---|---|---|
| 47 | isopropyl | 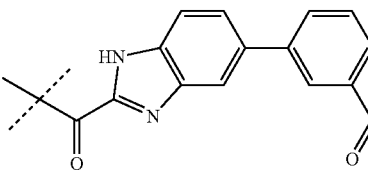 | MS (M + H) 512; $^1$H NMR (400 MHz, CD$_3$OD) δ ppm 8.30 (t, J = 1.7 Hz, 1 H), 7.99 (d, J = 7.8 Hz, 1 H), 7.87 (d, J = 7.8 Hz, 1 H), 7.59-7.66 (m, 1 H), 7.54 (t, J = 7.8 Hz, 1 H), 7.41 (s, 1 H), 5.38 (spt, J = 6.6 Hz, 1 H), 4.30-4.40 (m, 1 H), 4.13-4.23 (m, 1 H), 3.85-3.95 (m, 1 H), 3.69-3.79 (m, 1 H), 2.90 (s, 2H), 2.65 (s, 2 H), 1.63-1.77 (m, 4 H), 1.42 (dd, J = 6.6, 1.8 Hz, 6 H) |
| 48 | isopropyl | 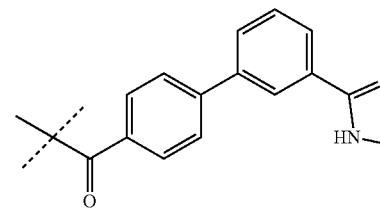 | MS (MH + 1) 496; $^1$H NMR (CDCl$_3$, 400 MHz): 8.31 (s, 1H), 8.02 (d, 1H), 7.78 (m, 3H), 7.65 (m, 1H), 7.50 (m, 2H), 7.41 (s, 1H), 5.37 (m, 1H), 3.86 (br.s, 1H), 3.72 (br.s, 1H), 2.88 (s, 2H), 2.50 (s, 2H), 1.60 (m, 4H), 1.40 (d, 6H) |
| 49 | t-butyl | 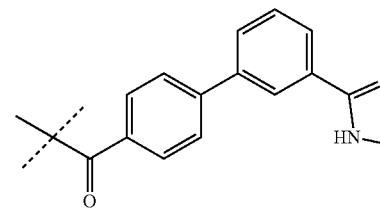 | MS (MH + 1) 510.25; $^1$H NMR (CDCl$_3$, 400 MHz): 8.32 (s, 1H), 8.00 (s, 1H), 7.80 (m, 3H), 7.60 (t, 1H), 7.54 (d, 2H), 7.32 (s, 1H), 3.90 (br.s, 1H), 3.70 (br.s, 1H), 3.50 (br.s, 2H), 2.85 (s, 2H), 2.65 (s, 2H), 1.56 (m, 13 H). |

Pharmacological Data

Biological Protocols

The utility of the compounds of present invention, in the treatment of diseases (such as are detailed herein) in animals, particularly mammals (e.g., humans) may be demonstrated by the activity thereof in conventional assays known to one of ordinary skill in the art, including the in vitro and in vivo assays described below. Such assays also provide a means whereby the activities of the compound of the present invention can be compared with the activities of other known compounds.

Direct Inhibition of the Activities of ACC1 and ACC2

The ACC inhibitory activity of the compound of the present invention was demonstrated by methods based on standard procedures. For example direct inhibition of ACC activity, for the compound of Formula (1) was determined using preparations of recombinant human ACC1 (rhACC1) and recombinant human ACC2 (rhACC2). Representative sequences of the recombinant human ACC1 and ACC2 that can be used in the assay are provided in FIG. 1 (SEQ ID NO. 1) and FIG. 2 (SEQ. ID NO. 2), respectively.

[1] Preparation of rhACC1. Two liters of SF9 cells, infected with recombinant baculovirus containing full length human ACC1 cDNA, were suspended in ice-cold lysis buffer (25 mM Tris, pH 7.5; 150 mM NaCl; 10% glycerol; 5 mM imidazole (EMD Bioscience; Gibbstown, N.J.); 2 mM TCEP (BioVectra; Charlottetown, Canada); Benzonase nuclease (10000 U/100 g cell paste; Novagen; Madison, Wis.); EDTA-free protease inhibitor cocktail (1 tab/50 mL; Roche Diagnostics; Mannheim, Germany). Cells were lysed by 3 cycles of freeze-thaw and centrifuged at 40,000×g for 40 minutes (4° C.). Supernatant was directly loaded onto a HisTrap FF crude column (GE Healthcare; Piscataway, N.J.) and eluted with an imidazole gradient up to 0.5 M over 20 column volumes (CV). ACC1-containing fractions were pooled and diluted 1:5 with 25 mM Tris, pH 7.5, 2 mM TCEP, 10% glycerol and direct loaded onto a CaptoQ (GE Healthcare) column and eluted with an NaCl gradient up to 1 M over 20 CV's. Phosphate groups were removed from purified ACC1 by incubation with lambda phosphatase (100 U/10 μM target protein; New England Biolabs; Beverly, Mass.) for 14 hours at 4° C.; okadaic acid was added (1 μM final concentration; Roche Diagnostics) to inhibit the phosphatase. Purified ACC1 was exchanged into 25 mM Tris, pH 7.5, 2 mM TCEP, 10% glycerol, 0.5 M NaCl by 6 hour dialysis at 4° C. Aliquots were prepared and frozen at −80° C.

[2] Measurement of rhACC1 inhibition. hACC1 was assayed in a Costar #3676 (Costar, Cambridge, Mass.) 384-well plate using the Transcreener ADP detection FP assay kit (Bellbrook Labs, Madison, Wis.) using the manufacturer's recommended conditions for a 50 µM ATP reaction. The final conditions for the assay were 50 mM HEPES, pH 7.2, 10 mM $MgCl_2$, 7.5 mM tripotassium citrate, 2 mM DTT, 0.1 mg/mL BSA, 30 µM acetyl-CoA, 50 µM ATP, and 10 mM $KHCO_3$. Typically, a 10 µl reaction was run for 120 min at 25° C., and 10 µl of Transcreener stop and detect buffer was added and the combination incubated at room temp for an additional 1 hour. The data was acquired on a Envision Fluorescence reader (Perkinelmer) using a 620 excitation Cy5 FP general dual mirror, 620 excitation Cy5 FP filter, 688 emission (S) and a 688 (P) emission filter.

[3] Preparation of rhACC2. Human ACC2 inhibition was measured using purified recombinant human ACC2 (hrACC2). Briefly, a full length Cytomax clone of ACC2 was purchased from Cambridge Bioscience Limited and was sequenced and subcloned into PCDNA5 FRT TO-TOPO (Invitrogen, Carlsbad, Calif.). The ACC2 was expressed in CHO cells by tetracycline induction and harvested in 5 liters of DMEM/F12 with glutamine, biotin, hygromycin and blasticidin with 1 µg/mL tetracycline (Invitrogen, Carlsbad, Calif.). The conditioned medium containing ACC2 was then applied to a Softlink Soft Release Avidin column (Promega, Madison, Wis.) and eluted with 5 mM biotin. 4 mgs of ACC2 were eluted at a concentration of 0.05 mg/mL (determined by A280) with an estimated purity of 95% (determined by A280). The purified ACC2 was dialyzed in 50 mM Tris, 200 mM NaCl, 4 mM DTT, 2 mM EDTA, and 5% glycerol. The pooled protein was frozen and stored at −80° C., with no loss of activity upon thawing. For measurement of ACC2 activity and assessment of ACC2 inhibition, test compounds were dissolved in DMSO and added to the rhACC2 enzyme as a 5× stock with a final DMSO concentration of 1%.

[4] Measurement of human ACC2 inhibition. hACC2 was assayed in a Costar #3676 (Costar, Cambridge, Mass.) 384-well plate using the Transcreener ADP detection FP assay kit (Bellbrook Labs, Madison, Wis.) using the manufacturer's recommended conditions for a 50 uM ATP reaction. The final conditions for the assay were 50 mM HEPES, pH 7.2, 5 mM $MgCl_2$, 5 mM tripotassium citrate, 2 mM DTT, 0.1 mg/mL BSA, 30 µM acetyl-CoA, 50 µM ATP, and 8 mM $KHCO_3$. Typically, a 10 µl reaction was run for 50 min at 25° C., and 10 µl of Transcreener stop and detect buffer was added and the combination incubated at room temp for an additional 1 hour. The data was acquired on an Envision Fluorescence reader (Perkinelmer) using a 620 excitation Cy5 FP general dual mirror, 620 excitation Cy5 FP filter, 688 emission (S) and a 688 (P) emission filter.

The results using the recombinant hACC1 and recombinant hACC2 Transcreener assays described above are summarized in the table below for the Compounds of Formula (I) exemplified in the Examples above. All of the examples in both assays were run with a minimum of n=3.

| Example | hACC1 (nM) | hACC2 (nM) |
| --- | --- | --- |
| 1 | 176 | 184 |
| 2 | 59.6 | 84.1 |
| 3 | 5400 | 2260 |
| 4 | 116 | 53 |
| 5 | 163 | 114 |
| 6 | 260 | 115 |
| 7 | 113 | 74.2 |
| 8 | 156 | 175 |
| 9 | 30.9 | 29.7 |
| 10 | 30.1 | 35.5 |
| 11 | 180 | 268 |
| 12 | 152 | 94.5 |
| 13 | 221 | 143 |
| 14 | 139 | 76.1 |
| 15 | 6.11 | 7.88 |
| 16 | 9.75 | 11.6 |
| 17 | 15.6 | 21.6 |
| 18 | 4.5 | 14.6 |
| 19 | 837 | 487 |
| 20 | 355 | 300 |
| 21 | 627 | 507 |
| 22 | 1010 | 685 |
| 23 | 1370 | 420 |
| 24 | 3140 | 557 |
| 25 | 600 | 202 |
| 26 | 20.4 | 7.49 |
| 27 | 2910 | 1140 |
| 28 | 6.70 | 5.35 |
| 29 | 13.7 | 6.16 |
| 30 | 16.1 | 18.8 |
| 31 | 23.1 | 54.8 |
| 32 | 31.8 | 12.5 |
| 33 | 16.3 | 8.7 |
| 34 | 55.8 | 42.6 |
| 35 | 32.6 | 12.5 |
| 36 | 44.4 | 29.3 |
| 37 | 6.6 | 3.2 |
| 38 | 33.5 | 19.9 |
| 39 | 29.1 | 29.8 |
| 40 | 10.2 | 6.1 |
| 41 | 8.6 | 15.2 |
| 42 | 39.9 | 30.4 |
| 43 | 98.4 | 133 |
| 44 | 34.4 | 35.9 |
| 45 | 4.9 | 10.0 |
| 46 | 11.6 | 15.7 |
| 47 | 32.5 | 25.7 |
| 48 | 59.5 | 28.0 |
| 49 | 54.7 | 24.7 |

Acute In Vivo Assessment of ACC Inhibition in Experimental Animals

The ACC inhibitory activity of the compounds of the present invention can be confirmed in vivo by evaluation of their ability to reduce malonyl-CoA levels in liver and muscle tissue from treated animals.

Measurement of malonyl-CoA production inhibition in experimental animals. In this method, male Sprague-Dawley Rats, maintained on standard chow and water ad libitum (225-275 g), were randomized prior to the study. Animals were either fed, or fasted for 18 hours prior to the beginning of the experiment. Two hours into the light cycle the animals were orally dosed with a volume of 5 mL/kg, (0.5% methyl cellulose; vehicle) or with the appropriate compound (prepared in vehicle). Fed vehicle controls were included to determine baseline tissue malonyl-CoA levels while fasted animals were included to determine the effect fasting had on malonyl-CoA levels. One hour after compound administration the animals were asphyxiated with $CO_2$ and the tissues were removed. Specifically, blood was collected by cardiac puncture and placed into BD Microtainer tubes containing EDTA (BD Biosciences, NJ), mixed, and placed on ice. Plasma was used to determine drug exposure. Liver and quadriceps were removed, immediately freeze-clamped, wrapped in foil and stored in liquid nitrogen.

Tissues were pulverized under liquid $N_2$ to ensure uniformity in sampling. Malonyl-CoA was extracted from the tissue (150-200 mg) with 5 volumes 10% tricarboxylic acid in Lysing Matrix A (MP Biomedicals, PN 6910) in a FastPrep FP120 (Thermo Scientific, speed=5.5; for 45 seconds). The supernatant containing malonyl-CoA was removed from the cell debris after centrifugation at 15000×g for 30 minutes (Eppendorf Centrifuge 5402). Samples were stably frozen at −80 C until analysis is completed.

Analysis of malonyl CoA levels in liver and muscle tissue can be evaluated using the following methodology.

The method utilizes the following materials: Malonyl-CoA tetralithium salt and malonyl-$^{13}C_3$-CoA trilithium salt which were purchased from Isotec (Miamisburg, Ohio, USA), sodium perchlorate (Sigma, cat no. 410241), trichloroacetic acid (ACROS, cat no. 42145), phosphoric acid (J.T. Baker, cat no. 0260-01), ammonium formate (Fluka, cat no. 17843), methanol (HPLC grade, J.T. Baker, cat no. 9093-33), and water (HPLC grade, J.T. Baker, 4218-03) were used to make the necessary mobile phases. Strata-X on-line solid phase extraction columns, 25 µm, 20 mm×2.0 mm I.D (cat no. 00M-S033-B0-CB) were obtained from Phenomenex (Torrance, Calif., USA). SunFire C18 reversed-phase columns, 3.5 µm, 100 mm×3.0 mm I.D. (cat no. 186002543) were purchased from Waters Corporation (Milford, Mass., USA).

This method may be performed utilizing the following equipment. Two-dimensional chromatography using an Agilent 1100 binary pump, an Agilent 1100 quaternary pump and two Valco Chem inert 6-port two position valves. Samples were introduced via a LEAP HTC PAL auto sampler with Peltier cooled stack maintained at 10° C. and a 204 sampling loop. The needle wash solutions for the autosampler are 10% trichloroacetic acid in water (w/v) for Wash 1 and 90:10 methanol:water for Wash 2. The analytical column (Sunfire) was maintained at 35° C. using a Micro-Tech Scientific Micro-LC Column Oven. The eluent was analyzed on an ABI Sciex API3000 triple quadrupole mass spectrometer with Turbo Ion Spray.

Two-dimensional chromatography was performed in parallel using distinct gradient elution conditions for on-line solid phase extraction and reversed-phase chromatography. The general design of the method was such that the first dimension was utilized for sample clean-up and capture of the analyte of interest followed by a brief coupling of both dimensions for elution from the first dimension onto the second dimension. The dimensions were subsequently uncoupled allowing for gradient elution of the analyte from the second dimension for quantification while simultaneously preparing the first dimension for the next sample in the sequence. When both dimensions were briefly coupled together, the flow of the mobile phase in the first dimension was reversed for analyte elution on to the second dimension, allowing for optimal peak width, peak shape, and elution time.

The first dimension of the HPLC system utilized the Phenomenex strata-X on-line solid phase extraction column and the mobile phase consisted of 100 mM sodium perchlorate/0.1% (v/v) phosphoric acid for solvent A and methanol for solvent B.

The second dimension of the HPLC system utilized the Waters SunFire C18 reversed-phase column and the mobile phase consisted of 100 mM ammonium formate for solvent A and methanol for solvent B. The initial condition of the gradient was maintained for 2 minutes and during this time the analyte was transferred to the analytical column. It was important that the initial condition was at a sufficient strength to elute the analyte from the on-line SPE column while retaining it on the analytical. Afterwards, the gradient rose linearly to 74.5% A in 4.5 minutes before a wash and re-equilibration step.

Mass spectrometry when coupled with HPLC can be a highly selective and sensitive method for quantitatively measuring analytes in complex matrices but is still subject to interferences and suppression. By coupling a two dimensional HPLC to the mass spectrometer, these interferences were significantly reduced. Additionally, by utilizing the Multiple Reaction Monitoring (MRM) feature of the triple quadrupole mass spectrometer, the signal-to-noise ratio was significantly improved.

For this assay, the mass spectrometer was operated in positive ion mode with a TurbolonSpray voltage of 2250V. The nebulizing gas was heated to 450° C. The Declustering Potential (DP), Focusing Potential (FP), and Collision Energy (CE) were set to 60, 340, and 42 V, respectively. Quadrupole 1 (Q1) resolution was set to unit resolution with Quadrupole 3 (Q3) set to low. The CAD gas was set to 8. The MRM transitions monitored were for malonyl CoA: 854.1→347.0 m/z (L. Gao et al. (2007) J. Chromatogr. B 853, 303-313); and for malonyl-$^{13}C_3$-CoA: 857.1→350.0 m/z with dwell times of 200 ms. The eluent was diverted to the mass spectrometer near the expected elution time for the analyte, otherwise it was diverted to waste to help preserve the source and improve robustness of the instrumentation. The resulting chromatograms were integrated using Analyst software (Applied Biosystems). Tissue concentrations for malonyl CoA were calculated from a standard curve prepared in a 10% solution of trichloroacetic acid in water.

Samples comprising the standard curve for the quantification of malonyl-CoA in tissue extracts were prepared in 10% (w/v) trichloroacetic acid (TCA) and ranged from 0.01 to 1 pmol/µL. Malonyl-$^{13}C_3$-CoA (final concentration of 0.4 pmol/µL) was added to each standard curve component and sample as an internal standard.

Six intra-assay quality controls were prepared; three from a pooled extract prepared from fasted animals and three from a pool made from fed animals. These were run as independent samples spiked with 0, 0.1 or 0.3 pmol/µL $^{12}C$-malonyl-CoA as well as malonyl-$^{13}C_3$-CoA (0.4 pmol/µL). Each intra-assay quality control contained 85% of aqueous tissue extract with the remaining portion contributed by internal standard (0.4 pmol/µL) and $^{12}C$-malonyl-CoA. Inter assay controls were included in each run; they consist of one fasted and one fed pooled sample of quadriceps and/or one fasted and one fed pooled sample of liver. All such controls are spiked with malonyl-$^{13}C_3$-CoA (0.4 pmol/µL).

What is claimed is:

1. A method for treating a diabetes-related disease in a human comprising the step of administering to the human in need of such treatment a therapeutically effective amount of a compound of Formula (I)

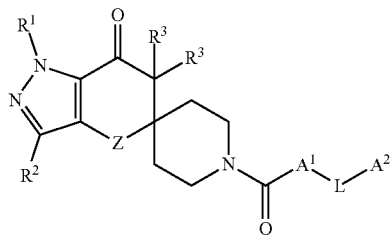

or a pharmaceutically acceptable salt thereof, wherein
$R^1$ is $(C_1-C_6)$alkyl, $(C_3-C_7)$cycloalkyl, tetrahydrofuranyl or oxetanyl, wherein said $(C_1-C_6)$alkyl is optionally substituted with 1 to 3 substituents independently selected from $(C_1-C_3)$alkoxy, hydroxy, fluoro, phenyl, tetrahydrofuranyl or oxetanyl;
$R^2$ is hydrogen, halo, $(C_1-C_3)$alkyl, or cyano;
$R^3$ are each independently hydrogen or $(C_1-C_3)$alkyl;
L is a direct bond or a $(C_1-C_6)$alkylene wherein one carbon of the $(C_1-C_6)$alkylene is optionally replaced by —C(O)—, —C(O)NH—, —NHC(O)—, —O—, —S—, NH or N$(C_1-C_3)$alkyl;
Z is $CH_2$ or O;
$A^1$ and $A^2$ are each independently $(C_6-C_{10})$aryl, 5 to 12 membered heteroaryl or 8 to 12 membered fused heterocyclicaryl; wherein said $(C_6-C_{10})$aryl, 5 to 12 membered heteroaryl or 8 to 12 membered fused heterocyclicaryl are each optionally substituted with one to three substituents independently selected from $(C_1-C_3)$alkyl, $(C_1-C_3)$alkoxy, halo, amino, $(C_1-C_3)$alkylamino, di$(C_1-C_3)$alkylamino, hydroxy, cyano and amido wherein the alkyl portion of the $(C_1-C_3)$alkyl, $(C_1-C_3)$alkoxy, $(C_1-C_3)$alkylamino and di$(C_1-C_3)$alkylamino are optionally substituted with one to five fluoro; and wherein one of $A^1$ or $A^2$ is substituted by $CO_2R^4$, $(C_1-C_6)CO_2R^4$, tetrazolyl or $(C_1-C_6)$tetrazolyl; and
$R^4$ is $(C_1-C_8)$alkyl, $(C_3-C_8)$cycloalkyl or $(C_1-C_6)$alkyl-$(C_3-C_8)$cycloalkyl.

2. The method of claim 1, wherein the diabetes-related disease is selected from nonalcoholic fatty liver disease, hepatic insulin resistance, hyperglycemia, metabolic syndrome, impaired glucose tolerance, diabetic neuropathy, diabetic nephropathy, diabetic retinopathy, obesity, dyslipidemia, hypertension, hyperinsulinemia, and insulin resistance syndrome.

3. The method of claim 1, wherein the diabetes-related disease is selected from nonalcoholic fatty liver disease, hepatic insulin resistance, hyperglycemia, and obesity.

4. The method of claim 1, wherein the diabetes-related disease is nonalcoholic fatty liver disease.

5. The method of claim 1, further comprising the step of administering a second pharmaceutical agent, wherein the second agent is an anti-diabetic agent selected from the group consisting of metformin, acetohexamide, chlorpropamide, diabinese, glibenclamide, glipizide, glyburide, glimepiride, gliclazide, glipentide, gliquidone, glisolamide, tolazamide, tolbutamide, tendamistat, trestatin, acarbose, adiposine, camiglibose, emiglitate, miglitol, voglibose, pradimicin-Q, salbostatin, balaglitazone, ciglitazone, darglitazone, englitazone, isaglitazone, pioglitazone, rosiglitazone, troglitazone, exendin-3, exendin-4, trodusquemine, reservatrol, hyrtiosal extract, sitagliptin, vildagliptin, alogliptin and saxagliptin.

6. The method of claim 1, wherein the compound of Formula (I) is where $R^1$ is isopropyl or t-butyl; and where $R^2$ is hydrogen; or a pharmaceutically acceptable salt thereof.

7. The method of claim 1, wherein the compound of Formula (I) is where $A^1$ is phenyl, pyridinyl, indazolyl, indolyl, benzoimidazolyl, pyrrolopyridinyl or pyrrolopyrimidinyl; each optionally substituted with one methyl, methoxy, methylamino or dimethylamino; or a pharmaceutically acceptable salt thereof.

8. The method of claim 1, wherein the compound of Formula (I) is where $A^1$ is phenyl, indolyl or benzoimidazolyl optionally substituted with methyl, or pyridinyl optionally substituted with methylamino or dimethylamino; or a pharmaceutically acceptable salt thereof.

* * * * *